(12) United States Patent
Flynn et al.

(10) Patent No.: US 9,193,719 B2
(45) Date of Patent: Nov. 24, 2015

(54) 1,2,4-TRIAZOL-5-ONES AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Daniel L. Flynn, Lawrence, KS (US); Gary E. L. Brandt, Alameda, CA (US); Michael D. Kaufman, Lawrence, KS (US); Hanumaiah Telikepalli, Lawrence, KS (US); Timothy Malcolm Caldwell, Fishers, IN (US); Thiwanka Samarakoon, Quincy, MA (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/214,160

(22) Filed: Mar. 14, 2014

(65) Prior Publication Data
US 2014/0296252 A1    Oct. 2, 2014

Related U.S. Application Data

(60) Provisional application No. 61/792,662, filed on Mar. 15, 2013.

(51) Int. Cl.
| | | |
|---|---|---|
| *A61K 31/506* | (2006.01) | |
| *C07D 417/14* | (2006.01) | |
| *C07D 401/14* | (2006.01) | |
| *C07D 405/14* | (2006.01) | |
| *C07D 413/14* | (2006.01) | |
| *A61K 31/444* | (2006.01) | |

(52) U.S. Cl.
CPC ............ *C07D 417/14* (2013.01); *C07D 401/14* (2013.01); *C07D 405/14* (2013.01); *C07D 413/14* (2013.01); *A61K 31/444* (2013.01); *A61K 31/506* (2013.01)

(58) Field of Classification Search
CPC .. C07D 401/14; C07D 405/14; C07D 413/14; C07D 417/14; A61K 31/444; A61K 31/506
See application file for complete search history.

(56) References Cited

FOREIGN PATENT DOCUMENTS

WO       WO 9636633 A1 *  11/1996

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*
A. Dewar et al., 4 Cell Cycle, 851-853 (2005).*
A.L. Dewar et al., 105 Blood 3127-3122 (2005).*
H. Ohno et al., 5 Molecular Cancer Therapeutics, 2634-2643 (2006).*
S. M. Pyonteck et al., 19 Nature Medicine, 1264-1272 (2013).*
C.J. Burns et al., 21 Expert Opinion on Therapeutic Patents, 147-165 (2011).*
N. Gupta et al., 185 Journal of Immunology, 2261-2272 (2010).*
M.C. Heinrich et al., 96 Blood, 929-932 (2000).*
S. Attoub et al., 62 Cancer Research, 4879-4883 (2002).*
B.P. Rubin et al., 61 Cancer Research, 8118-8121 (2001).*
R.D. Carvajal et al., 305 Journal of the American Medical Association, 2327-2334 (2011).*
A. Yasuda et al., 5 Molecular Cancer, 1-10 (2006).*
G. Di Lorenzo et al., 30 European Journal of Surgical Oncology, 987-992 (2004).*
A.Z. Al-Muhsen et al., 34 Clinical and Experimental Allergy, 911-917 (2004).*
M. Boissan. 67 Journal of Leukocyte Biology, 135-148 (2000).*
L. Reber et al., 533 European Journal of Pharmacology, 327-340 (2006).*
D.S. El Agamy et al, 690 European Journal of Pharmacology, 1-3 (2012).*
W.G. Roberts et al., 65 Cancer Research, 957-966 (2005).*
J. Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
S. Fogarty et al., 1804 Biochimica et Biophysica Acta, 581-591 (2010).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
P.A. LeWitt, 359 New England Journal of Medicine, 2468-2473 (2008).*
S. Judge et al., 111 Pharmacology & Therapeutics, 224-259 (2006).*
V. Brinkmann et al., 9 Nature Reviews | Drug Discovery, 883-897 (2010).*
J.D. Mitchell et al., 369 The Lancet, 2031-2041 (2007).*
Kinase Inhibitors, Methods in Molecular Biology 795 (B. Kuster ed., 2012).*
K. Henriksen et al., 18 Osteoporosis International, 681-685 (2006).*
C. Minkin, 34 Calcified Tissue International, 285-290 (1982).*

* cited by examiner

*Primary Examiner* — Alexander R Pagano
(74) *Attorney, Agent, or Firm* — Cooley LLP

(57) ABSTRACT

Described are compounds of Formula I

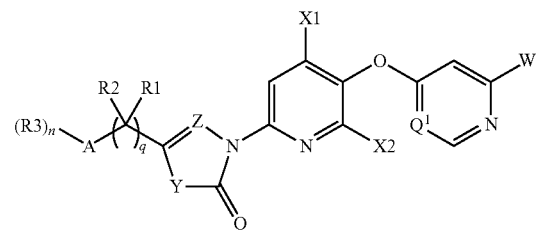

Formula I which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

36 Claims, No Drawings

1,2,4-TRIAZOL-5-ONES AND ANALOGS EXHIBITING ANTI-CANCER AND ANTI-PROLIFERATIVE ACTIVITIES

PRIORITY

This application claims the benefit of U.S. Provisional Application No. 61/792,662, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_061_01US_SeqList_ST25.txt, date recorded: Mar. 15, 2014, file size 18 kilobytes).

FIELD OF THE INVENTION

Disclosed are compounds which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

BACKGROUND OF THE INVENTION

Autoimmune diseases, including autoimmune arthritis, represent significant human diseases of high morbidity and prevalence. Rheumatoid arthritis affects ~0.6% of the world population (Firestein, G. S., Nature (2003) 423: 356). While the adaptive immune response, involving generation of autoantibodies which react with tissue antigen, is involved in the etiology and initial propagation of these diseases (Edwards, J. C. et al, New England Journal of Medicine (2004) 350: 2572; Genovese, M. C. et al, New England Journal of Medicine (2005) 353: 1114), the chronic manifestations of tissue and joint damage are mediated in large part by cellular events mediated by the innate immune response (Firestein, G. S., Nature (2003) 423: 356; Paniagua, R. T. et al, Arthritis Research & Therapy (2010) 12: R32). Contributing cell types from the innate immune response which mediate chronic tissue damage include fibroblast-like synoviocytes, macrophages, mast cells, and osteoclasts.

Kinases represent a protein family that play critical roles in mammalian cell function, including cell proliferation, survival, motility, response to growth factors, and secretion of cytokines and other proinflammatory, proangiogenic, and immunomodulatory substances. Thus, elucidation of kinases which mediate these events in fibroblast-like synoviocytes, macrophages, mast cells, and osteoclasts represents a rational approach to new therapies for the treatment of autoimmune diseases.

Imatinib is a marketed kinase inhibitor for the treatment of the cancer chronic myelogenous leukemia (CML, Druker, B. J. et al, New England Journal of Medicine (2001) 344: 1031) and for the treatment of gastrointestinal stromal tumors (GIST, Demetri, G. D., et al, New England Journal of Medicine (2002) 347: 472). Imatinib has also shown benefit in cancer patients co-presenting with autoimmune diseases such as rheumatoid arthritis (Ihara, M. K. et al, Clinical Rheumatology (2003) 22: 362; Eklund, K. K. and Joensuu, H., Ann Medicine (2003) 35: 362; Ames, P. R. et al, Journal of Rheumatology (2008) 35: 1682). The kinases inhibited by imatinib which confer its efficacy in the treatment of CML and GIST are BCR-ABL kinase and c-KIT kinase, respectively. Beyond these two kinases, other kinases inhibited by imatinib include c-FMS, PDGFR-alpha, and PDGFR-beta (Dewer, A. L. et al, Blood (2005) 105: 3127; Fabian, M. A. et al, Nature Biotechnology (2005) 23: 329.

Recent research disclosures have identified c-FMS kinase to be associated with activation of synovial macrophages, PDGFR kinase to be associated with activation of fibroblast-like synoviocytes, and c-KIT kinase to be associated with activation of mast cells (Paniagua, R. T., et al Journal of Clinical Investigation (2006) 116: 2633). c-FMS kinase has also been associated with the proliferation and differentiation of monocytes into macrophages and osteoclasts, which are recruited to mediate joint damage in rheumatoid arthritis (Paniagua, R. T. et al, Arthritis Research & Therapy (2010) 12: R32; Yao, Z. et al, Journal of Biological Chemistry (2006) 281: 11846; Patel, S, and Player, M. R. Current Topics in Medicinal Chemistry (2009) 9: 599; Pixley, F. J. et al, Trends in Cell Biology (2004) 14: 628).

In recent years, the importance of the tumor microenvironment in cancer motility, invasion, and metastasis has become more clearly defined. Specifically, the role of tumor-associated macrophages (TAMs) in tumor progression has been studied. These host (stromal) macrophages are recruited to tumor sites or to pre-metastatic niches to modify the tumor environment and render that environment more conducive to tumor motility, invasion and metastasis. These TAMs are known to express c-FMS receptor tyrosine kinase (also known as CSF-1R) on their surfaces and to rely on signaling through this kinase by binding to the activating ligands CSF-1 (also known as macrophage colony stimulating factor, or MCSF) and interleukin-34 (IL-34). Activation of this c-FMS/MCSF (CSF1-R/CSF-1) signaling axis stimulates monocyte proliferation, differentiation into tumor associated macrophages, and promotion of macrophage cell survival. By stimulating the TAM component of the tumor microenvironment, c-FMS kinase activation is associated with tumor cell migration, invasion, and metastasis (J. Condeelis and J. W. Pollard, Cell (2006) 124: 263; S. Patel and M. R. Player, Current Topics in Medicinal Chemistry (2009) 9: 599). Ablation of CSF-1, the ligand for c-FMS kinase, in mice reduced tumor progression and significantly reduced metastasis in a murine model of breast cancer; whereas overexpression of CSF-1 accelerated metastasis in this model (E. Y. Lin et al, Journal of Experimental Medicine (2001) 193: 727). Furthermore, an interaction between tumor cells and macrophages has been described, wherein macrophage secretion of the tumor growth factor EGF and tumor cell secretion of CSF-1 establish a paracrine loop that promotes tumor migration and invasiveness. This paracrine loop was blocked by administration of an antibody to the c-FMS kinase (J. Wyckoff et al, Cancer Research (2004) 64: 7022). Correlative clinical data have also shown that overexpression of CSF-1 in tumors is a predictor of poor prognosis (R. D. Leek and A. L. Harris, Journal of Mammary Gland Biology Neoplasia (2002) 7: 177; E. Y. Lin et al, Journal of Mammary Gland Biology Neoplasia (2002) 7: 147). c-FMS kinase activation is also required for osteoclast differentiation and activation. Its involvement in mediating bone metastases of various cancers, including breast and prostate cancers, has been reported (S. Patel and M. R. Player, Current Topics in Medicinal Chemistry (2009) 9: 599). High plasma concentrations of CSF-1 have been reported in bone metastatic prostate cancer, implicating activation of osteoclast c-FMS kinase in prostate cancer bone metastases (H. Ide, et al, Human Cell (2008) 21:1). c-FMS inhibitors have been reported to reduce radiographic bone lesions when evaluated in models of metastatic bone disease (C. L. Manthey, et al, Molecular Cancer Therapy (2009) 8: 3151; H. Ohno et al, Mol. Cancer. Therapy (2006) 5: 2634). MCSF-mediated activation of both LYVE-1+ and LYVE1− macrophages also mediates pathological angiogenesis and lymphangiogenesis in murine models of cancer, and blockade of c-FMS signaling resulted in suppression of tumor angiogenesis/lymphangiogenesis (Y. Kubota et al., Journal of Experimental Medicine (2009) 206: 1089). Administration of a CSF-1R inhibitor blocked the recruitment of bone marrow derived TAMs and also bone marrow derived monocytic myeloid-derived suppressor cells (MDSCs) to tumor sites; this blockade led to a significant decrease in tumor angiogenesis and when combined with anti-VEGFR-2 therapy synergistically suppressed tumor growth (S. J. Priceman, et al. Blood (2010) 115: 1461). Irradiation of glioblastoma tumors in mice was shown to cause a temporary decrease in tumor size only to be followed by a rebound tumor vasculogenesis mediated by the recruitment of bone marrow derived monocytes expressing CD11b and F4/80 surface antigens (M. Kioi et al, Journal of Clinical Investigation (2010) 120: 694). CD11b+ and F4/80+ monocytes are also known to express functional c-FMS receptors. Hence, blockade of tumor infiltrating c-FMS+ bone marrow derived monocytes by the use of c-FMS kinase inhibitors offers the potential to prevent tumor rebound vasculogenesis and glioblastoma tumor progression. CSF-1R blockade has also been shown to reverse immunotolerance mechanisms in an immunocompetent murine breast cancer model and promote the appearance of anti-tumor immune programs by upregulating CD8+ T-cell-mediated tumor suppression. Restoration of an anti-tumor immune program was mechanistically linked to c-FMS inhibitor blockade of TAM-mediated Programmed Death Ligand-1 (PDL-1) immunotolerance (D. G. DeNardo, et al. Cancer Discovery (2011) 1: OF52).

Hence, small molecule inhibitors of c-FMS kinase, c-KIT kinase, or PDGFR kinases provide a rational approach to new therapies for the treatment of autoimmune diseases, and to particularly block the chronic tissue destruction mediated by the innate immune system. Inhibition of c-FMS kinase also provides a rational approach to new therapies for the treatment of cancers, especially for the treatment of cancer invasiveness, cancer angiogenesis or vasculogenesis, cancer metastasis, cancer immunotolerance, and for the treatment of cancers prone to bone metastases.

There is a need to provide kinase inhibitors which selectively inhibit kinases causative of the chronic tissue destruction in autoimmune disease (c-FMS, c-KIT, PDGFR), without inhibiting other kinases targeted by marketed cancer therapeutics (ABL, BCR-ABL, KDR, SRC, LCK, LYN, FGFR and other kinases). The present invention discloses novel inhibitors that inhibit c-FMS, c-KIT, and/or PDGFR kinases for the treatment of autoimmune diseases which also exhibit selectivity by not potently inhibiting other kinases including ABL, BCR-ABL, KDR, SRC, LCK, LYN, FGFR, MET and other kinases. The inhibitors of the present invention also find utility in the treatment of other mammalian diseases, including human diseases, mediated by c-FMS, c-KIT, or PDGFR kinases.

Such diseases include, without limitation, cancers, autoimmune diseases, and bone resorptive diseases.

SUMMARY OF THE INVENTION

In one aspect, compounds of the Formula I are described:

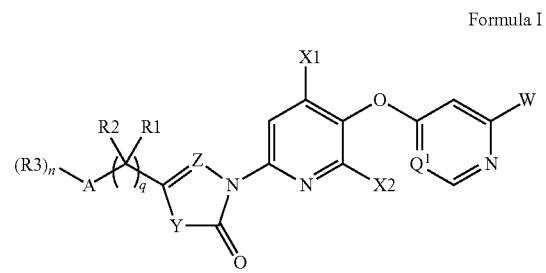

Formula I and pharmaceutically acceptable salts, enantiomers, stereoisomers, or tautomers thereof, wherein A is selected from the group consisting of C1-C6 alkyl, branched C3-C8alkyl, fluoroC1-C6alkyl wherein the alkyl is fully or partially fluorinated, C3-C8carbocyclyl, phenyl, 4-8 membered heterocyclic ring and heteroaryl, wherein each A moiety may be further substituted with one, two, or three R3 moieties;

W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties;

Q1 is CH or N;

X1 and X2 are individually and independently hydrogen or C1-C6 alkyl;

Y is NR4 or O;

Z is N or CR11;

each R1 and R2 is individually and independently hydrogen, C1-C6 alkyl, deutero-C1-C6 alkyl wherein the alkyl chain is partially or completely deuterated, fluoroC1-C6alkyl wherein the alkyl is fully or partially fluorinated, hydroxyl, C1-C6 alkoxy, fluoroC1-C6alkoxy wherein the alkyl group is fully or partially fluorinated, or halogen;

each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

R4 is hydrogen, C1-C6 alkyl, deutero-C1-C6 alkyl wherein the alkyl chain is partially or completely deuterated, or branched C3-C8 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl;

each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkylene is optionally substituted with C1-C4 alkyl;

each R7 is independently and individually selected from the group consisting of

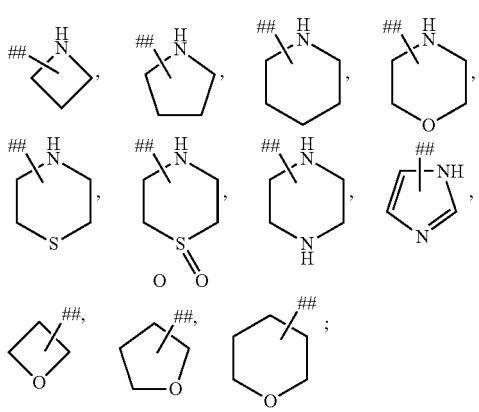

and wherein the symbol (##) is the point of attachment to respective W, R5 or R6 moieties containing a R7 moiety;

each R7 is optionally substituted with —(R10)$_p$;

each R8 and R9 is individually and independently hydrogen, C1-C6 alkyl, fluoro-C1-C6 alkyl wherein the alkyl chain is partially or completely fluorinated, or branched C3-C8 alkyl;

each R10 is individually and independently C1-C6 alkyl, —(CH$_2$)$_m$—CN, —(CH$_2$)$_m$—OR3, —(CH$_2$)$_m$—NR8(R9), or —(CH$_2$)$_m$—C(O)—R6, wherein each alkyl or alkylene is optionally substituted with one or two C1-C6 alkyl;

wherein each alkylene is optionally substituted with C1-C4 alkyl;

R11 is hydrogen, C1-C6 alkyl, deutero-C1-C6 alkyl wherein the alkyl chain is partially or completely deuterated, or branched C3-C8 alkyl;

each m is individually and independently 0, 1, 2, or 3;
each n is individually and independently 0, 1, 2, or 3;
each p is 0, 1, 2, or 3;
each q is 0, 1, or 2.

In one embodiment of Formula I, Y is NR4 or O.
In one embodiment of Formula I, Y is NR4.
In one embodiment of Formula I, Y is O.
In one embodiment of Formula I, Z is N or CR11.
In one embodiment of Formula I, Z is N.
In one embodiment of Formula I, Z is CR11.
In one embodiment of Formula I, W is C5-C6heteroaryl optionally substituted by one, two, or three R5.
In one embodiment of Formula I, W is —NHC(O)R6, —NHC(O)R7, or —NHC(O)N(R8)R9.
In one embodiment of Formula I, W is —NHC(O)R6.
In one embodiment of Formula I, W is —NHC(O)R7.
In one embodiment of Formula I, W is —NHC(O)N(R8)R9.
In one embodiment of Formula I, W is —C(O)N(R8)R9.
In one embodiment of Formula I, W is phenyl optionally substituted by one, two, or three R5.
In one embodiment of Formula I, X1 and X2 are individually and independently hydrogen or C1-C6 alkyl.
In one embodiment of Formula I, X1 and X2 are hydrogen.
In one embodiment of Formula I, one of X1 and X2 is hydrogen and the other is C1-C6alkyl.
In one embodiment of Formula I, A is taken from the group consisting of C1-C6 alkyl, branched C3-C8alkyl, fluoroC1-C6alkyl wherein the alkyl is fully or partially fluorinated, C3-C8-carbocyclyl, phenyl, a 4-8 membered heterocyclic ring and heteroaryl; and wherein each A moiety may be further substituted with one, two, or three R3 moieties.

In one embodiment of Formula I, each R1 and R2 is individually and independently hydrogen, C1-C6 alkyl, deutero-C1-C6 alkyl wherein the alkyl chain is partially or completely deuterated, fluoroC1-C6alkyl wherein the alkyl is fully or partially fluorinated, hydroxyl, C1-C6 alkoxy, fluoroC1-C6alkoxy wherein the alkyl group is fully or partially fluorinated, or halogen.

In one embodiment of Formula I, each R1 is hydrogen.
In one embodiment of Formula I, each R1 and R2 is hydrogen.
In one embodiment of Formula I, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula I, q is 0, 1, or 2.
In one embodiment of Formula I, q is 0.
In one embodiment of Formula I, q is 1.
In one embodiment of Formula I, q is 2.
In one embodiment of Formula I, n is 0, 1, or 2.
In one embodiment of Formula I, n is 0.
In one embodiment of Formula I, n is 1.
In one embodiment of Formula I, n is 2.
In one embodiment of Formula I, n is 3.

In one embodiment, the compound of Formula I is a compound of Formula Ia wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof.

Formula Ia

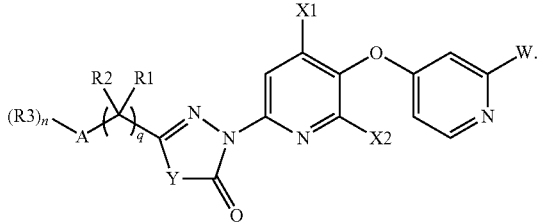

In one embodiment of Formula Ia, W is C5-C6heteroaryl optionally substituted by one, two, or three R5.
In one embodiment of Formula Ia, W is pyrazolyl, imidazolyl, isoxazolyl, oxazolyl, thiazolyl, triazolyl, or pyridinyl and wherein each W is optionally substituted by one, two, or three R5.
In one embodiment of Formula Ia, W is pyrazolyl optionally substituted by one, two, or three R5.
In one embodiment of Formula Ia, W is imidazolyl optionally substituted by one, two, or three R5.
In one embodiment of Formula Ia, W is isoxazolyl optionally substituted by one or two R5.
In one embodiment of Formula Ia, W is oxazolyl optionally substituted by one or two R5.
In one embodiment of Formula Ia, W is thiazolyl optionally substituted by one or two R5.
In one embodiment of Formula Ia, W is triazolyl optionally substituted by one or two R5.
In one embodiment of Formula Ia, W is pyridinyl optionally substituted by one, two, or three R5.

In one embodiment of Formula Ia, W is —NHC(O)R6, —NHC(O)R7, or —NHC(O)N(R8)R9.

In one embodiment of Formula Ia, W is —NHC(O)R6.

In one embodiment of Formula Ia, W is —NHC(O)R7.

In one embodiment of Formula Ia, W is —NHC(O)N(R8)R9.

In one embodiment of Formula Ia, W is —C(O)N(R8)R9.

In one embodiment of Formula Ia, W is phenyl optionally substituted by one, two, or three R5.

In one embodiment of Formula Ia, X1 and X2 are individually and independently hydrogen or C1-C6 alkyl.

In one embodiment of Formula Ia, X1 and X2 are hydrogen.

In one embodiment of Formula Ia, one of X1 and X2 is hydrogen and the other is C1-C6alkyl.

In one embodiment of Formula Ia, Y is NR4 and R4 is hydrogen, C1-C6 alkyl, deutero-C1-C6 alkyl wherein the alkyl chain is partially or completely deuterated, or branched C3-C8 alkyl.

In one embodiment of Formula Ia, Y is NR4 and R4 is hydrogen or C1-C6 alkyl.

In one embodiment of Formula Ia, Y is NR4 and R4 is hydrogen.

In one embodiment of Formula Ia, Y is NR4 and R4 is C1-C6 alkyl.

In one embodiment of Formula Ia, Y is O.

In one embodiment of Formula Ia, A is taken from the group consisting of C1-C6 alkyl, branched C3-C8alkyl, fluoroC1-C6alkyl wherein the alkyl is fully or partially fluorinated, C3-C8carbocyclyl, phenyl, a 4-8 membered heterocyclic ring and heteroaryl; and wherein each A moiety may be further substituted with one, two, or three R3 moieties.

In one embodiment of Formula Ia, A is taken from the group consisting of C1-C6 alkyl, branched C3-C8alkyl, C3-C8carbocyclyl, phenyl and a 4-8 membered heterocyclic ring; and wherein each A moiety may be further substituted with one, two, or three R3 moieties.

In one embodiment of Formula Ia, A is branched C3-C8alkyl, optionally further substituted with one, two, or three R3 moieties.

In one embodiment of Formula Ia, A is C3-C8carbocyclyl, optionally further substituted with one, two, or three R3 moieties.

In one embodiment of Formula Ia, A is phenyl, optionally further substituted with one, two, or three R3 moieties.

In one embodiment of Formula Ia, A is a 4-8 membered heterocyclic ring, optionally further substituted with one, two, or three R3 moieties.

In one embodiment of Formula Ia, each R1 and R2 is individually and independently hydrogen, C1-C6 alkyl, deutero-C1-C6 alkyl wherein the alkyl chain is partially or completely deuterated, fluoroC1-C6alkyl wherein the alkyl is fully or partially fluorinated, hydroxyl, C1-C6 alkoxy, fluoroC1-C6alkoxy wherein the alkyl group is fully or partially fluorinated, or halogen.

In one embodiment of Formula Ia, each R1 is hydrogen.

In one embodiment of Formula Ia, each R1 and R2 is hydrogen.

In one embodiment of Formula Ia, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ia, q is 0, 1, or 2.

In one embodiment of Formula Ia, q is 0.

In one embodiment of Formula Ia, q is 1.

In one embodiment of Formula Ia, q is 2.

In one embodiment of Formula Ia, n is 0, 1, or 2.

In one embodiment of Formula Ia, n is 0.

In one embodiment of Formula Ia, n is 1.

In one embodiment of Formula Ia, n is 2.

In one embodiment of Formula Ia, n is 3.

In one embodiment, the compound of Formula I is a compound of Formula Ib wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof.

Formula Ib

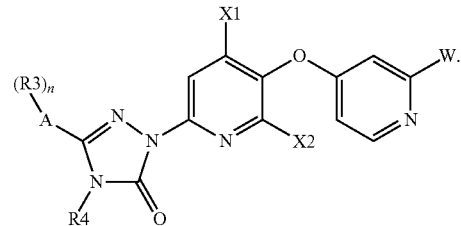

In one embodiment of Formula Ib, W is C5-C6heteroaryl optionally substituted by one, two, or three R5.

In one embodiment of Formula Ib, W is pyrazolyl, imidazolyl, isoxazolyl, oxazolyl, thiazolyl, triazolyl, or pyridinyl and wherein each W is optionally substituted by one, two, or three R5.

In one embodiment of Formula Ib, W is pyrazolyl optionally substituted by one, two, or three R5.

In one embodiment of Formula Ib, W is imidazolyl optionally substituted by one, two, or three R5.

In one embodiment of Formula Ib, W is isoxazolyl optionally substituted by one or two R5.

In one embodiment of Formula Ib, W is oxazolyl optionally substituted by one or two R5.

In one embodiment of Formula Ib, W is thiazolyl optionally substituted by one or two R5.

In one embodiment of Formula Ib, W is triazolyl optionally substituted by one or two R5.

In one embodiment of Formula Ib, W is pyridinyl optionally substituted by one, two, or three R5.

In one embodiment of Formula Ib, W is —NHC(O)R6, —NHC(O)R7, or —NHC(O)N(R8)R9.

In one embodiment of Formula Ib, W is —NHC(O)R6.

In one embodiment of Formula Ib, W is —NHC(O)R7.

In one embodiment of Formula Ib, W is —NHC(O)N(R8)R9.

In one embodiment of Formula Ib, W is —C(O)N(R8)R9.

In one embodiment of Formula Ib, W is phenyl optionally substituted by one, two, or three R5.

In one embodiment of Formula Ib, X1 and X2 are individually and independently hydrogen or C1-C6 alkyl.

In one embodiment of Formula Ib, X1 and X2 are hydrogen.

In one embodiment of Formula Ib, one of X1 and X2 is hydrogen and the other is C1-C6alkyl.

In one embodiment of Formula Ib, R4 is hydrogen, C1-C6 alkyl, deutero-C1-C6 alkyl wherein the alkyl chain is partially or completely deuterated, or branched C3-C8 alkyl.

In one embodiment of Formula Ib, R4 is hydrogen or C1-C6 alkyl.

In one embodiment of Formula Ib, R4 is hydrogen.

In one embodiment of Formula Ib, R4 is C1-C6 alkyl.

In one embodiment of Formula Ib, A is taken from the group consisting of C1-C6 alkyl, branched C3-C8alkyl, fluoroC1-C6alkyl wherein the alkyl is fully or partially fluorinated, C3-C8carbocyclyl, phenyl, a 4-8 membered heterocyclic ring and heteroaryl; and wherein each A moiety may be further substituted with one, two, or three R3 moieties.

In one embodiment of Formula Ib, A is taken from the group consisting of C1-C6 alkyl, branched C3-C8alkyl, C3-C8carbocyclyl, phenyl and a 4-8 membered heterocyclic ring; and wherein each A moiety may be further substituted with one, two, or three R3 moieties.

In one embodiment of Formula Ib, A is branched C3-C8alkyl, optionally further substituted with one, two, or three R3 moieties.

In one embodiment of Formula Ib, A is tert-butyl, optionally further substituted with one, two, or three R3 moieties.

In one embodiment of Formula Ib, A is tert-pentyl, optionally further substituted with one, two, or three R3 moieties.

In one embodiment of Formula Ib, A is neo-pentyl, optionally further substituted with one, two, or three R3 moieties.

In one embodiment of Formula Ib, A is isobutyl, optionally further substituted with one, two, or three R3 moieties.

In one embodiment of Formula Ib, A is isopropyl, optionally further substituted with one, two, or three R3 moieties.

In one embodiment of Formula Ib, A is C3-C8carbocyclyl, optionally further substituted with one, two, or three R3 moieties.

In one embodiment of Formula Ib, A is cyclopropyl, optionally further substituted with one, two, or three R3 moieties.

In one embodiment of Formula Ib, A is cyclobutyl, optionally further substituted with one, two, or three R3 moieties.

In one embodiment of Formula Ib, A is cyclopentyl, optionally further substituted with one, two, or three R3 moieties.

In one embodiment of Formula Ib, A is cyclohexyl, optionally further substituted with one, two, or three R3 moieties.

In one embodiment of Formula Ib, A is phenyl, optionally further substituted with one, two, or three R3 moieties.

In one embodiment of Formula Ib, A is a 4-8 membered heterocyclic ring, optionally further substituted with one, two, or three R3 moieties In one embodiment of Formula Ib, A is tetrahydrofuranyl, optionally further substituted with one, two, or three R3 moieties.

In one embodiment of Formula Ib, A is tetrahydropyranyl, optionally further substituted with one, two, or three R3 moieties.

In one embodiment of Formula Ib, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ib, n is 0, 1, or 2.

In one embodiment of Formula Ib, n is 0.

In one embodiment of Formula Ib, n is 1.

In one embodiment of Formula Ib, n is 2.

In one embodiment of Formula Ib, n is 3.

In one embodiment, the compound of Formula I is a compound of Formula Ic wherein: X1 and X2 are individually and independently hydrogen or C1-C6 alkyl; or a pharmaceutically acceptable salt, enantiomer, stereoisomer, or tautomer thereof Formula Ic In one embodiment of Formula Ic, X1 and X2 are hydrogen.

In one embodiment of Formula Ic, one of X1 and X2 is hydrogen and the other is C1-C6alkyl.

In one embodiment of Formula Ic, one of X1 and X2 is hydrogen and the other is methyl.

In one embodiment of Formula Ic, R3 is hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ic, R3 is hydrogen, C1-C6 alkyl, fluoro-C1-C6 alkyl wherein the alkyl chain is partially or completely fluorinated, or C1-C6 alkoxy.

In one embodiment of Formula Ic, R5 is hydrogen, C1-C6 alkyl, deutero-C1-C6 alkyl wherein the alkyl chain is partially or completely deuterated, branched C3-C8 alkyl, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl.

In one embodiment of Formula Ic, R5 is hydrogen, C1-C6 alkyl, or deutero-C1-C6 alkyl wherein the alkyl chain is partially or completely deuterated.

In one embodiment of Formula Ic, R5 is C1-C6 alkyl, or deutero-C1-C6 alkyl wherein the alkyl chain is partially or completely deuterated.

In one embodiment of Formula Ic, R5 is methyl.

In one embodiment of Formula Ic, q is 0, 1, or 2.

In one embodiment of Formula Ic, q is 0 or 1.

In one embodiment of Formula Ic, q is 0.

In one embodiment of Formula Ic, q is 1.

In one embodiment of Formula Ic, q is 2.

In one embodiment, the compound of Formula I is a compound of Formula Id wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof Formula Id

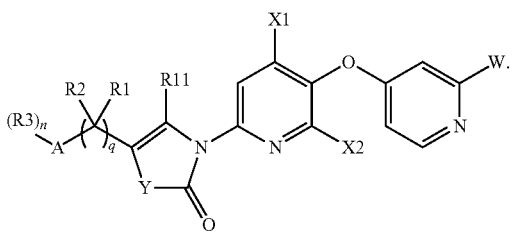

In one embodiment of Formula Id, W is C5-C6heteroaryl optionally substituted by one, two, or three R5.

In one embodiment of Formula Id, W is pyrazolyl, imidazolyl, isoxazolyl, oxazolyl, thiazolyl, triazolyl, or pyridinyl and wherein each W is optionally substituted by one, two, or three R5.

In one embodiment of Formula Id, W is pyrazolyl optionally substituted by one, two, or three R5.

In one embodiment of Formula Id, W is imidazolyl optionally substituted by one, two, or three R5.

In one embodiment of Formula Id, W is isoxazolyl optionally substituted by one or two R5.

In one embodiment of Formula Id, W is oxazolyl optionally substituted by one or two R5.

In one embodiment of Formula Id, W is thiazolyl optionally substituted by one or two R5.

In one embodiment of Formula Id, W is triazolyl optionally substituted by one or two R5.

In one embodiment of Formula Id, W is pyridinyl optionally substituted by one, two, or three R5.

In one embodiment of Formula Id, W is —NHC(O)R6, —NHC(O)R7, or —NHC(O)N(R8)R9.

In one embodiment of Formula Id, W is —NHC(O)R6.

In one embodiment of Formula Id, W is —NHC(O)R7.

In one embodiment of Formula Id, W is —NHC(O)N(R8)R9.

In one embodiment of Formula Id, W is —C(O)N(R8)R9.

In one embodiment of Formula Id, W is phenyl optionally substituted by one, two, or three R5.

In one embodiment of Formula Id, X1 and X2 are individually and independently hydrogen or C1-C6 alkyl.

In one embodiment of Formula Id, X1 and X2 are hydrogen.

In one embodiment of Formula Id, one of X1 and X2 is hydrogen and the other is C1-C6alkyl.

In one embodiment of Formula Id, Y is NR4 and R4 is hydrogen, C1-C6 alkyl, deutero-C1-C6 alkyl wherein the alkyl chain is partially or completely deuterated, or branched C3-C8 alkyl.

In one embodiment of Formula Id, Y is NR4 and R4 is hydrogen or C1-C6 alkyl.

In one embodiment of Formula Id, Y is NR4 and R4 is hydrogen.

In one embodiment of Formula Id, Y is NR4 and R4 is C1-C6 alkyl.

In one embodiment of Formula Id, Y is O.

In one embodiment of Formula Id, A is taken from the group consisting of C1-C6 alkyl, branched C3-C8alkyl, fluoroC1-C6alkyl wherein the alkyl is fully or partially fluorinated, C3-C8carbocyclyl, phenyl, a 4-8 membered heterocyclic ring and heteroaryl; and wherein each A moiety may be further substituted with one, two, or three R3 moieties.

In one embodiment of Formula Id, A is taken from the group consisting of C1-C6 alkyl, branched C3-C8alkyl, C3-C8carbocyclyl, phenyl and a 4-8 membered heterocyclic ring; and wherein each A moiety may be further substituted with one, two, or three R3 moieties.

In one embodiment of Formula Id, A is branched C3-C8alkyl, optionally further substituted with one, two, or three R3 moieties.

In one embodiment of Formula Id, A is C3-C8carbocyclyl, optionally further substituted with one, two, or three R3 moieties.

In one embodiment of Formula Id, A is phenyl, optionally further substituted with one, two, or three R3 moieties.

In one embodiment of Formula Id, A is a 4-8 membered heterocyclic ring, optionally further substituted with one, two, or three R3 moieties.

In one embodiment of Formula Id, each R1 and R2 is individually and independently hydrogen, C1-C6 alkyl, deutero-C1-C6 alkyl wherein the alkyl chain is partially or completely deuterated, fluoroC1-C6alkyl wherein the alkyl is fully or partially fluorinated, hydroxyl, C1-C6 alkoxy, fluoroC1-C6alkoxy wherein the alkyl group is fully or partially fluorinated, or halogen.

In one embodiment of Formula Id, each R1 is hydrogen.

In one embodiment of Formula Id, each R1 and R2 is hydrogen.

In one embodiment of Formula Id, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Id, R11 is hydrogen, C1-C6 alkyl, deutero-C1-C6 alkyl wherein the alkyl chain is partially or completely deuterated, or branched C3-C8 alkyl.

In one embodiment of Formula Id, R11 is hydrogen.

In one embodiment of Formula Id, q is 0, 1, or 2.

In one embodiment of Formula Id, q is 0.

In one embodiment of Formula Id, q is 1.

In one embodiment of Formula Id, q is 2.

In one embodiment of Formula Id, n is 0, 1, or 2.

In one embodiment of Formula Id, n is 0.

In one embodiment of Formula Id, n is 1.

In one embodiment of Formula Id, n is 2.

In one embodiment of Formula Id, n is 3.

In one embodiment, the compound of Formula I is a compound of Formula Ie wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof Formula Ie

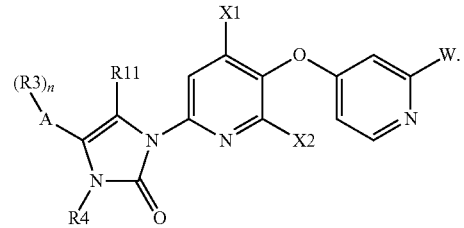

In one embodiment of Formula Ie, W is C5-C6heteroaryl optionally substituted by one, two, or three R5.

In one embodiment of Formula Ie, W is pyrazolyl, imidazolyl, isoxazolyl, oxazolyl, thiazolyl, triazolyl, or pyridinyl and wherein each W is optionally substituted by one, two, or three R5.

In one embodiment of Formula Ie, W is pyrazolyl optionally substituted by one, two, or three R5.

In one embodiment of Formula Ie, W is imidazolyl optionally substituted by one, two, or three R5.

In one embodiment of Formula Ie, W is isoxazolyl optionally substituted by one or two R5.

In one embodiment of Formula Ie, W is oxazolyl optionally substituted by one or two R5.

In one embodiment of Formula Ie, W is thiazolyl optionally substituted by one or two R5.

In one embodiment of Formula Ie, W is triazolyl optionally substituted by one or two R5.

In one embodiment of Formula Ie, W is pyridinyl optionally substituted by one, two, or three R5.

In one embodiment of Formula Ie, W is —NHC(O)R6, —NHC(O)R7, or —NHC(O)N(R8)R9.

In one embodiment of Formula Ie, W is —NHC(O)R6.

In one embodiment of Formula Ie, W is —NHC(O)R7.

In one embodiment of Formula Ie, W is —NHC(O)N(R8)R9.

In one embodiment of Formula Ie, W is —C(O)N(R8)R9.

In one embodiment of Formula Ie, W is phenyl optionally substituted by one, two, or three R5.

In one embodiment of Formula Ie, X1 and X2 are individually and independently hydrogen or C1-C6 alkyl.

In one embodiment of Formula Ie, X1 and X2 are hydrogen.

In one embodiment of Formula Ie, one of X1 and X2 is hydrogen and the other is C1-C6alkyl.

In one embodiment of Formula Ie, R4 is hydrogen, C1-C6 alkyl, deutero-C1-C6 alkyl wherein the alkyl chain is partially or completely deuterated, or branched C3-C8 alkyl.

In one embodiment of Formula Ie, R4 is hydrogen or C1-C6 alkyl.

In one embodiment of Formula Ie, R4 is hydrogen.

In one embodiment of Formula Ie, R4 is C1-C6 alkyl.

In one embodiment of Formula Ie, A is taken from the group consisting of C1-C6 alkyl, branched C3-C8alkyl, fluoroC1-C6alkyl wherein the alkyl is fully or partially fluorinated, C3-C8carbocyclyl, phenyl, a 4-8 membered heterocyclic ring and heteroaryl; and wherein each A moiety may be further substituted with one, two, or three R3 moieties.

In one embodiment of Formula Ie, A is taken from the group consisting of C1-C6 alkyl, branched C3-C8alkyl, C3-C8carbocyclyl, phenyl and a 4-8 membered heterocyclic ring; and wherein each A moiety may be further substituted with one, two, or three R3 moieties.

In one embodiment of Formula Ie, A is branched C3-C8alkyl, optionally further substituted with one, two, or three R3 moieties.

In one embodiment of Formula Ie, A is tert-butyl, optionally further substituted with one, two, or three R3 moieties.

In one embodiment of Formula Ie, A is tert-pentyl, optionally further substituted with one, two, or three R3 moieties.

In one embodiment of Formula Ie, A is neo-pentyl, optionally further substituted with one, two, or three R3 moieties.

In one embodiment of Formula Ie, A is isobutyl, optionally further substituted with one, two, or three R3 moieties.

In one embodiment of Formula Ie, A is isopropyl, optionally further substituted with one, two, or three R3 moieties.

In one embodiment of Formula Ie, A is C3-C8carbocyclyl, optionally further substituted with one, two, or three R3 moieties.

In one embodiment of Formula Ie, A is cyclopropyl, optionally further substituted with one, two, or three R3 moieties.

In one embodiment of Formula Ie, A is cyclobutyl, optionally further substituted with one, two, or three R3 moieties.

In one embodiment of Formula Ie, A is cyclopentyl, optionally further substituted with one, two, or three R3 moieties.

In one embodiment of Formula Ie, A is cyclohexyl, optionally further substituted with one, two, or three R3 moieties.

In one embodiment of Formula Ie, A is phenyl, optionally further substituted with one, two, or three R3 moieties.

In one embodiment of Formula Ie, A is a 4-8 membered heterocyclic ring, optionally further substituted with one, two, or three R3 moieties.

In one embodiment of Formula Ie, A is tetrahydrofuranyl, optionally further substituted with one, two, or three R3 moieties.

In one embodiment of Formula Ie, A is tetrahydropyranyl, optionally further substituted with one, two, or three R3 moieties.

In one embodiment of Formula Ie, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ie, R11 is hydrogen, C1-C6 alkyl, deutero-C1-C6 alkyl wherein the alkyl chain is partially or completely deuterated, or branched C3-C8 alkyl.

In one embodiment of Formula Ie, R11 is hydrogen.

In one embodiment of Formula Ie, n is 0, 1, or 2.

In one embodiment of Formula Ie, n is 0.

In one embodiment of Formula Ie, n is 1.

In one embodiment of Formula Ie, n is 2.

In one embodiment of Formula Ie, n is 3.

In one embodiment, the compound of Formula I is a compound of Formula If wherein: X1 and X2 are individually and independently hydrogen or C1-C6 alkyl; or a pharmaceutically acceptable salt, enantiomer, stereoisomer, or tautomer thereof

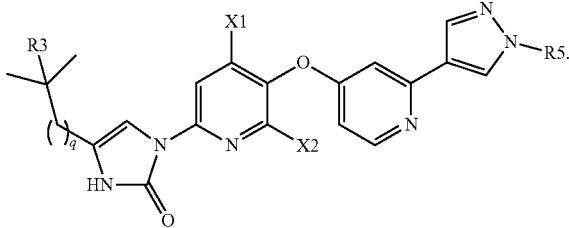

Formula If

In one embodiment of Formula If, X1 and X2 are hydrogen.

In one embodiment of Formula If, one of X1 and X2 is hydrogen and the other is C1-C6alkyl.

In one embodiment of Formula If, one of X1 and X2 is hydrogen and the other is methyl.

In one embodiment of Formula If, R3 is hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula If, R3 is hydrogen, C1-C6 alkyl, fluoro-C1-C6 alkyl wherein the alkyl chain is partially or completely fluorinated, or C1-C6 alkoxy.

In one embodiment of Formula If, R5 is hydrogen, C1-C6 alkyl, deutero-C1-C6 alkyl wherein the alkyl chain is partially or completely deuterated, branched C3-C8 alkyl, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl.

In one embodiment of Formula If, R5 is hydrogen, C1-C6 alkyl, or deutero-C1-C6 alkyl wherein the alkyl chain is partially or completely deuterated.

In one embodiment of Formula If, R5 is C1-C6 alkyl, or deutero-C1-C6 alkyl wherein the alkyl chain is partially or completely deuterated.

In one embodiment of Formula If, R5 is methyl.

In one embodiment of Formula If, q is 0, 1, or 2.

In one embodiment of Formula If, q is 0 or 1.

In one embodiment of Formula If, q is 0.

In one embodiment of Formula If, q is 1.

In one embodiment of Formula If, q is 2.

In one embodiment, the compound of Formula I is a compound of Formula Ig wherein: W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties; or a pharmaceutically acceptable salt, enantiomer, stereoisomer, or tautomer thereof.

Formula Ig

In one embodiment of Formula Ig, W is C5-C6heteroaryl optionally substituted by one, two, or three R5.

In one embodiment of Formula Ig, W is pyrazolyl, imidazolyl, isoxazolyl, oxazolyl, thiazolyl, triazolyl, or pyridinyl and wherein each W is optionally substituted by one, two, or three R5.

In one embodiment of Formula Ig, W is pyrazolyl optionally substituted by one, two, or three R5.

In one embodiment of Formula Ig, W is imidazolyl optionally substituted by one, two, or three R5.

In one embodiment of Formula Ig, W is isoxazolyl optionally substituted by one or two R5.

In one embodiment of Formula Ig, W is oxazolyl optionally substituted by one or two R5 f.

In one embodiment of Formula Ig, W is thiazolyl optionally substituted by one or two R5.

In one embodiment of Formula Ig, W is triazolyl optionally substituted by one or two R5.

In one embodiment of Formula Ig, W is pyridinyl optionally substituted by one, two, or three R5.

In one embodiment of Formula Ig, W is —NHC(O)R6, —NHC(O)R7, or —NHC(O)N(R8)R9.

In one embodiment of Formula Ig, W is —NHC(O)R6.

In one embodiment of Formula Ig, W is —NHC(O)R7.

In one embodiment of Formula Ig, W is —NHC(O)N(R8)R9.

In one embodiment of Formula Ig, W is —C(O)N(R8)R9.

In one embodiment of Formula Ig, W is phenyl optionally substituted by one, two, or three R5.

In one embodiment of Formula Ig, X1 and X2 are individually and independently hydrogen or C1-C6 alkyl.

In one embodiment of Formula Ig, X1 and X2 are hydrogen.

In one embodiment of Formula Ig, one of X1 and X2 is hydrogen and the other is C1-C6alkyl.

In one embodiment of Formula Ig, A is taken from the group consisting of C1-C6 alkyl, branched C3-C8alkyl, fluoroC1-C6alkyl wherein the alkyl is fully or partially fluorinated, C3-C8carbocyclyl, phenyl, a 4-8 membered heterocyclic ring and heteroaryl.

In one embodiment of Formula Ig, A is taken from the group consisting of C1-C6 alkyl, branched C3-C8alkyl, C3-C8carbocyclyl, phenyl and a 4-8 membered heterocyclic ring; and wherein each A moiety may be further substituted with one, two, or three R3 moieties.

In one embodiment of Formula Ig, A is branched C3-C8alkyl, optionally further substituted with one, two, or three R3 moieties.

In one embodiment of Formula Ig, A is tert-butyl, optionally further substituted with one, two, or three R3 moieties.

In one embodiment of Formula Ig, A is tert-pentyl, optionally further substituted with one, two, or three R3 moieties.

In one embodiment of Formula Ig, A is neo-pentyl, optionally further substituted with one, two, or three R3 moieties.

In one embodiment of Formula Ig, A is isobutyl, optionally further substituted with one, two, or three R3 moieties.

In one embodiment of Formula Ig, A is isopropyl, optionally further substituted with one, two, or three R3 moieties.

In one embodiment of Formula Ig, A is C3-C8carbocyclyl, optionally further substituted with one, two, or three R3 moieties.

In one embodiment of Formula Ig, A is cyclopropyl, optionally further substituted with one, two, or three R3 moieties.

In one embodiment of Formula Ig, A is cyclobutyl, optionally further substituted with one, two, or three R3 moieties.

In one embodiment of Formula Ig, A is cyclopentyl, optionally further substituted with one, two, or three R3 moieties.

In one embodiment of Formula Ig, A is cyclohexyl, optionally further substituted with one, two, or three R3 moieties.

In one embodiment of Formula Ig, A is phenyl, optionally further substituted with one, two, or three R3 moieties.

In one embodiment of Formula Ig, A is a 4-8 membered heterocyclic ring, optionally further substituted with one, two, or three R3 moieties.

In one embodiment of Formula Ig, A is tetrahydrofuranyl, optionally further substituted with one, two, or three R3 moieties.

In one embodiment of Formula Ig, A is tetrahydropyranyl, optionally further substituted with one, two, or three R3 moieties.

In one embodiment of Formula Ig, each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ig, n is 0, 1, or 2.

In one embodiment of Formula Ig, n is 0.

In one embodiment of Formula Ig, n is 1.
In one embodiment of Formula Ig, n is 2.
In one embodiment of Formula Ig, n is 3.
In one embodiment, the compound of Formula I is a compound of Formula Ih wherein: X1 and X2 are individually and independently hydrogen or C1-C6 alkyl; or a pharmaceutically acceptable salt, enantiomer, stereoisomer, or tautomer thereof Formula Ih In one embodiment of Formula Ih, X1 and X2 are hydrogen.
In one embodiment of Formula Ih, one of X1 and X2 is hydrogen and the other is C1-C6alkyl.
In one embodiment of Formula Ih, one of X1 and X2 is hydrogen and the other is methyl.
In one embodiment of Formula Ih, R3 is hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.
In one embodiment of Formula Ih, R3 is hydrogen, C1-C6 alkyl, fluoro-C1-C6 alkyl wherein the alkyl chain is partially or completely fluorinated, or C1-C6 alkoxy.
In one embodiment of Formula Ih, R5 is hydrogen, C1-C6 alkyl, deutero-C1-C6 alkyl wherein the alkyl chain is partially or completely deuterated, branched C3-C8 alkyl, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl.
In one embodiment of Formula Ih, R5 is hydrogen, C1-C6 alkyl, or deutero-C1-C6 alkyl wherein the alkyl chain is partially or completely deuterated.
In one embodiment of Formula Ih, R5 is C1-C6 alkyl, or deutero-C1-C6 alkyl wherein the alkyl chain is partially or completely deuterated.
In one embodiment of Formula Ih, R5 is methyl.
In one embodiment of Formula Ih, q is 0, 1, or 2.
In one embodiment of Formula Ih, q is 0 or 1.
In one embodiment of Formula Ih, q is 0.
In one embodiment of Formula Ih, q is 1.
In one embodiment of Formula Ih, q is 2.
In some embodiments, the invention comprises a compound selected from the group consisting of 3-(4-fluorobenzyl)-1-(6-methyl-5-((2-(1-methyl-1H-pyrazol-4-yl)pyridin-4-yl)oxy)pyridin-2-yl)-1H-1,2,4-triazol-5(4H)-one, 3-benzyl-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorobenzyl)-1-(5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-methyl-1H-pyrazol-4-yl)pyridin-4-yl)oxy)pyridin-2-yl)-1H-1,2,4-triazol-5(4H)-one, 3-isopropyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclohexyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-ethyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2'-methyl-[2,4'-bipyridin]-4-yl)oxy)pyridin-2-yl)-1H-1,2,4-triazol-5(4H)-one, 3-(tert-butyl)-1-(6-methyl-5-((6'-methyl-[2,3'-bipyridin]-4-yl)oxy)pyridin-2-yl)-1H-1,2,4-triazol-5(4H)-one, N-(4-((6-(3-(tert-butyl)-5-oxo-4,5-dihydro-1H-1,2,4-triazol-1-yl)-2-methylpyridin-3-yl)oxy)pyridin-2-yl)acetamide, 3-(tert-butyl)-1-(6-methyl-5-((2-(2-methylthiazol-5-yl)pyridin-4-yl)oxy)pyridin-2-yl)-1H-1,2,4-triazol-5(4H)-one, 3-(tert-butyl)-4-methyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(4-(1-methylpiperidin-4-yl)phenyl)pyridin-4-yl)oxy)pyridin-2-yl)-1H-1,2,4-triazol-5(4H)-one, 3-(2-methoxyethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(2-methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(methoxymethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-(2-hydroxyethyl)-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(4-methyl-1H-imidazol-1-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(tetrahydro-2H-pyran-4-yl)-1H-1,2,4-triazol-5(4H)-one, N-(4((6-(3-(tert-butyl)-5-oxo-4,5-dihydro-1H-1,2,4-triazol-1-yl)-2-methylpyridin-3-yl)oxy)pyridin-2-yl)-1-methylpiperidine-4-carboxamide, 3-isobutyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-imidazol-4-yl)pyridin-4-yl)oxy)pyridin-2-yl)-1H-1,2,4-triazol-5(4H)-one, 1-(5-((2-(1H-pyrazol-4-yl)pyridin-4-yl)oxy)-6-methylpyridin-2-yl)-3-(tert-butyl)-1H-1,2,4-triazol-5(4H)-one, 1-(6-methyl-5-((2-(1-methyl-1H-pyrazol-4-yl)pyridin-4-yl)oxy)pyridin-2-yl)-3-(tert-pentyl)-1H-1,2,4-triazol-5(4H)-one, 4-((6-(3-(tert-butyl)-5-oxo-4,5-dihydro-1H-1,2,4-triazol-1-yl)pyridin-3-yl)oxy)-N-methylpicolinamide, 1-(6-methyl-5-((2-(1-methyl-1H-pyrazol-4-yl)pyridin-4-yl)oxy)pyridin-2-yl)-3-(1-methylcyclopropyl)-1H-1,2,4-triazol-5(4H)-one, 3-(4-fluorophenyl)-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorophenyl)-1-(6-methyl-5-((2-(4-methyl-1H-imidazol-1-yl)pyridin-4-yl)oxy)pyridin-2-yl)-1H-1,2,4-triazol-5(4H)-one, 3-(4-((6-(3-(tert-butyl)-5-oxo-4,5-dihydro-1H-1,2,4-triazol-1-yl)-2-methylpyridin-3-yl)oxy)pyridin-2-yl)-1,1-dimethylurea, 3-(tert-butyl)-1-(4-methyl-5-((2-(1-methyl-1H-pyrazol-4-yl)pyridin-4-yl)oxy)pyridin-2-yl)-1H-1,2,4-triazol-5(4H)-one, N-(4-((6-(3-(4-fluorophenyl)-5-oxo-4,5-dihydro-1H-1,2,4-triazol-1-yl)-2-methylpyridin-3-yl)oxy)pyridin-2-yl)cyclopropanecarboxamide, 3-(tert-butyl)-1-(4,6-dimethyl-5-((2-(1-methyl-1H-pyrazol-4-yl)pyridin-4-yl)oxy)pyridin-2-yl)-1H-1,2,4-triazol-5(4H)-one, 3-cyclopentyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclopropyl-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-neopentyl-1H-1,2,4-triazol-5(4H)-one, 3-cyclobutyl- 1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-ethyl-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(oxazol-5-yl)pyridin-4-yl)oxy)pyridin-2-yl)-1H-1,2,4-triazol-5(4H)-one, 3-(tert-butyl)-1-(6-methyl-5-((6'-(4-methylpiperazin-1-yl)-[2,3'-bipyridin]-4-yl)oxy)pyridin-2-yl)-1H-1,2,4-triazol-5(4H)-one, 3-(tert-butyl)-1-(6-methyl-5-((2'-(4-methylpiperazin-1-yl)-[2,4'-bipyridin]-4-yl)oxy)pyridin-2-yl)-1H-1,2,4-triazol-5(4H)-one, 3-(1-hydroxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(1-(trifluoromethyl)cyclobutyl)-1H-1,2,4-triazol-5(4H)-one, N-(4-((6-(3-(2-methoxypropan-2-yl)-5-oxo-4,5-dihydro-1H-1,2,4-triazol-1-yl)-4-methylpyridin-3-yl)oxy)pyridin-2-yl)acetamide, N-(4-((6-(3-(tert-butyl)-5-oxo-4,5-dihydro-1H-1,2,4-triazol-1-yl)-2-methylpyridin-3-yl)oxy)pyridin-2-yl)cyclopropanecarboxamide, 3-(1-methoxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((6-(1-methyl-1H-pyrazol-4-yl)pyrimidin-4-yl)oxy)pyridin-2-yl)-1H-1,2,4-triazol-5(4H)-one, 4-(tert-butyl)-1-(6-methyl-5-((2-(1-methyl-1H-pyrazol-4-yl)pyridin-4-yl)oxy)pyridin-2-yl)-1H-imidazol-2(3H)-one, and 5-(tert-butyl)-3-(6-methyl-5-((2-(1-methyl-1H-pyrazol-4-yl)pyridin-4-yl)oxy)pyridin-2-yl)-1,3,4-oxadiazol-2(3H)-one.

In certain embodiments, the invention comprises a method of treating mammalian disease at least partially mediated by the kinase activity of c-FMS, PDGFR-β, or c-KIT kinases, wherein the kinase is a wildtype form, a mutant oncogenic form, an aberrant fusion protein form or a polymorph thereof, the method comprising administering to a mammal in need thereof an effective amount of a compound of Formula I.

In other embodiments, the present invention comprises a pharmaceutical composition, comprising a compound of Formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of Formula I.

In some embodiments, the invention includes a method of treating glioblastomas, breast cancers, pancreatic cancers, metastasis of primary tumor sites, or cancers that are metastatic to bone, the method comprising administering to a patient in need thereof an effective amount of a compound of Formula I.

In certain embodiments of the present methods, the compound is administered orally, parenterally, by inhalation, or subcutaneously.

In some embodiments, the invention provides the use of a compound of Formula I, or a pharmaceutically acceptable salt thereof, in the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of Formula I.

In some embodiments, the invention provides the use of a compound of Formula I, or a pharmaceutically acceptable salt thereof, in the treatment of glioblastomas, breast cancers, pancreatic cancers, metastasis of primary tumor sites, or cancers that are metastatic to bone, the method comprising administering to a patient in need thereof an effective amount of a compound of Formula I.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia.

In certain embodiments, the invention provides for the use of a compound of Formula I, or a pharmaceutically acceptable salt thereof, for the manufacture of a medicament for the treatment of glioblastomas, breast cancers, pancreatic cancers, metastasis of primary tumor sites, or cancers that are metastatic to bone.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts. Thus, the terms "compound", "compounds", "test compound" or "test compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl, 2-pentyl, 3-pentyl, 2-hexyl, and 3-hexyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH$_2$—, —CH$_2$CH$_2$—, and —CH$_2$CH$_2$CH$_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" or "carbocyclyl" as used herein refers to a monocyclic saturated carbon ring, wherein the number of ring atoms is indicated by a range of numbers. In exemplary embodiments, "cycloalkyl" or "carbocyclyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands through which the heterocyclyl ring is connected to an adjacent moiety. For example, in some embodiments, a ring N atom from the heterocyclyl is the bonding atom of the heterocylic moiety. In exemplary embodiments, "heterocyclyl" refers to a monocyclic hydrocarbon containing 4, 5, 6, 7 or 8 ring atoms (i.e., C4-C8 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, feline, horse, cow, pig, monkey, chimpanzee, baboon, or rhesus monkey.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

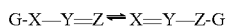

$$G\text{-}X\text{—}Y\text{=}Z \rightleftharpoons X\text{=}Y\text{—}Z\text{-}G$$

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

The compounds of Formula I, or pharmaceutically acceptable salts thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4th Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate "conc." is concentrated, "DBU" is 1,8-diazabicyclo[5.4.0]undec-7-ene, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphryl azide, "ESI" is electrospray ionization, "$Et_2O$" is diethylether, "EtOAc" is ethyl acetate, "EtOH" is ethanol, "GST" is glutathione S-transferase, "h" is hour or hours, "Hex" is hexane, "$IC_{50}$" is half maximal inhibitory concentration, "LiMHDS" is lithium bis(trimethylsilyl)amide, "MeCN" is acetonitrile, "MeOH" is methanol, "$Me_4tBuXPhos$" is di-tert-butyl(2',4',6'-triisopropyl-3,4,5,6-tetramethyl-[1,1'-biphenyl]-2-yl)phosphine, "MHz" is megahertz, "min" is minute or minutes, "MS" is mass spectrometry, "MTBE" is methyl tert-butyl ether, "NADH" is nicotinamide adenine dinucleotide, "NBS" is N-bromosuccinimide, "NMR" is nuclear magnetic resonance, "PBS" is phosphate buffered saline, "Pd/C" is palladium on carbon, "$Pd_2(dba)_3$" is tris(dibenzylideneacetone)dipalladium(0), "$Pd(PPh_3)_4$" is tetrakis(triphenylphosphine)palladium (0), "prep-HPLC" is preparative high performance liquid chromatography, "RT" is room temperature which is also known as "ambient temp," which will be understood to consist of a range of normal laboratory temperatures ranging from 15-25° C., "satd." is saturated, "TEA" is triethylamine, "TFA" is trifluoroacetic acid, "THF" is tetrahydrofuran, "Tris" is tris(hydroxymethyl)aminomethane, "Xantphos" is 4,5-bis(diphenylphosphino)-9,9-dimethylxanthene, and "X-Phos" is 2-dicyclohexylphosphino-2',4',6'-triisopropylbiphenyl.

General Chemistry

The compounds of Formula I are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula 1 is dependent upon the particular compound being synthesized, the starting compound, and the relative lability of the substituted moieties, as is well appreciated by the ordinary skilled chemist. All substituents, unless otherwise indicated, are as defined above.

The compounds of Formula I may contain —NH or —OH moieties in the W, R1, R2 and R3 positions. It will be understood by those skilled in the art that in some instances it may be advantageous to use an amine protecting group during synthesis to temporarily mask one or more —NH moieties. Said protecting group can be removed from any subsequent intermediate leading to the synthesis of the compounds of Formula I, using standard conditions that effect removal of said protecting group, said conditions of which will be familiar to those skilled in the art. When not specified in a scheme, it will be understood by those skilled in the art that the W, R1, R2 and R3 moieties represented in the schemes below may optionally contain standard amino or hydroxyl protecting groups that can be removed at any opportune time in the synthetic sequence.

Scheme 1 illustrates the preparation of Compounds 1, examples of Formula I wherein Y is NR4 and Z is N. In one embodiment, iodide 2 can react with triazolone 3 in the presence of copper(I) iodide and a suitable ligand, for example N,N-dimethylethane-1,2-diamine to afford 4. Additional conditions for the transformation of 2 to 4 include heating to about 100° C. with a carbonate base, for example potassium carbonate. Further reaction of 4 with M-W (5) in the presence of a palladium catalyst and a base, for example potassium carbonate provides compounds of formula 1. In one embodiment, to conversion of 4 to 1 is effected by reaction of 4 with reagent M-W (5), wherein M is trialkylstanyl or a boronic acid or boronate ester (when W is heteroaryl or phenyl). In another embodiment, to conversion of 4 to 1 is effected by reaction of 4 with reagent M-W (5), wherein M is H (when W is —NHC(O)R6, —NHC(O)R7, —NHC(O)N(R8)R9. Additional conditions for the transformation of 4 to 1 are dependent on the nature of the W-moiety, but generally include the use of palladium catalysts, for example $Pd(PPh_3)_4$ or $Pd_2(dba)_3$, optionally in the presence of additional ligands, for example Xantphos. General conditions to accomplish these transformation are well known to those skilled in the art and are further illustrated in the accompanying examples.

In another embodiment of Scheme 1, intermediate 4 (R4=H) can be prepared by the reaction of hydrazine 6 with reagent 8. Hydrazine 6 is efficiently prepared from iodide 2 by a two-step process commencing with the reaction with benzophenone hydrazone in the presence of $Pd(OAc)_2$, 2,2'-bis(diphenylphosphino)-1,1'-binaphthalene, and sodium tert-butoxide to provide 7. Acidic hydrolysis of 7 affords hydrazine 6.

In another embodiment of Scheme 1, compounds of formula 1 can be prepared directly from iodide 9 by reaction with M-W 5 using conditions described above. Iodide 9 is prepared from amine 10 by diazotization in the presence of an iodide source, for example potassium iodide or tetrabutylammonium iodide. Additional conditions for the conversion of 10 to 9 include treatment with tert-butyl nitrite in diiodomethane.

In another embodiment of Scheme 1, compounds of formula 1 can be prepared directly from hydrazine 12 by reaction with 8. Hydrazine 12 is prepared by the two-step sequence commencing with amine 10. Thus, diazotization of amine 10 in the resence of HF-pyridine affords fluoride 11. Treatment of 11 with hydrazine or hydrazine hydrate affords 12.

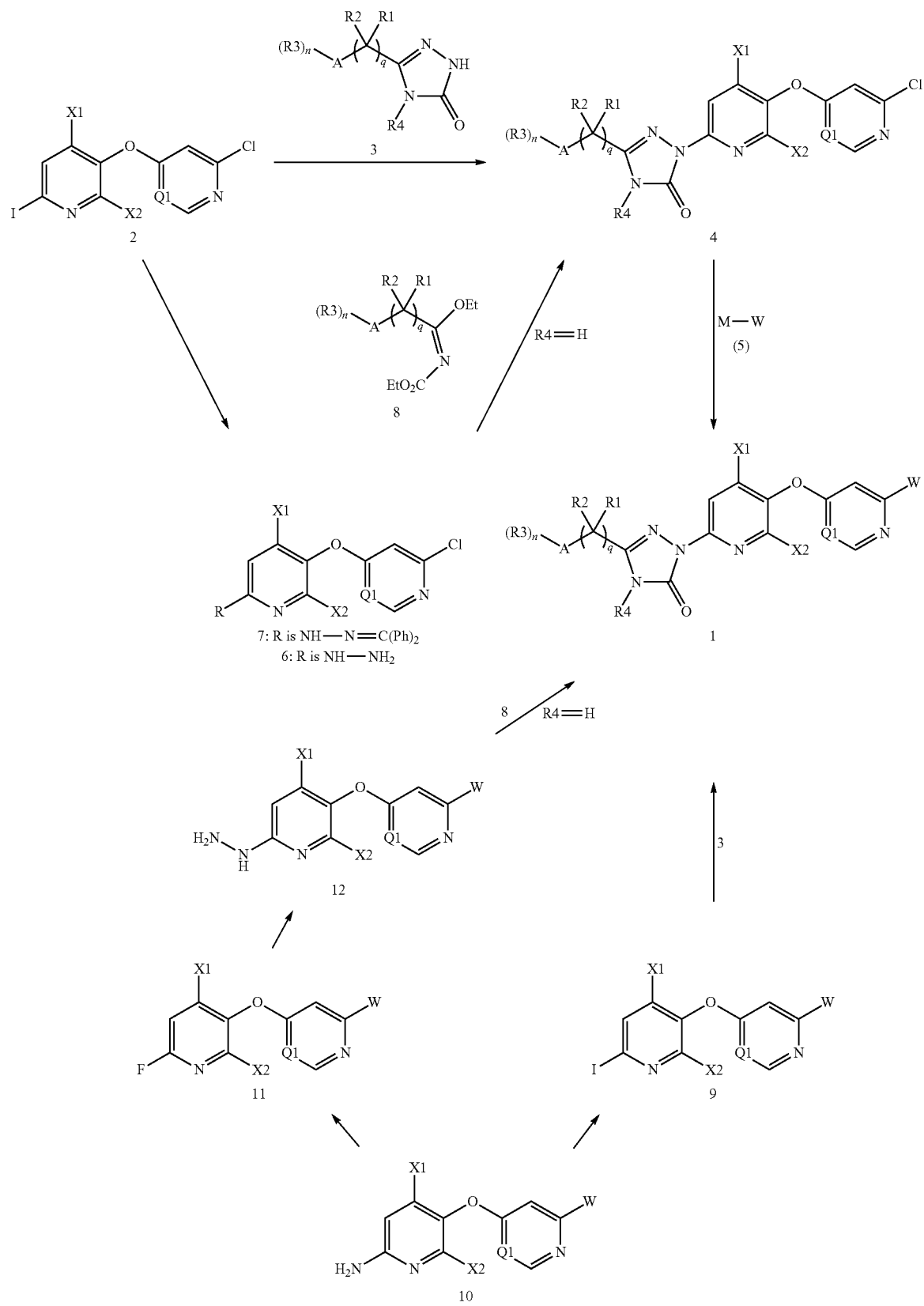

General intermediate 2 is prepared as illustrated in Scheme 2. Treatment of 3-hydroxypyridine 17 with iodine in the presence of a carbonate base affords iodide 18. Further treatment of 18 with 2,4-dichloropyridine (19, Q1 is CH) or 4,6-dichloropyrimdine (19, Q1 is N) in the presence of a base, for example potassium carbonate, provides 2.

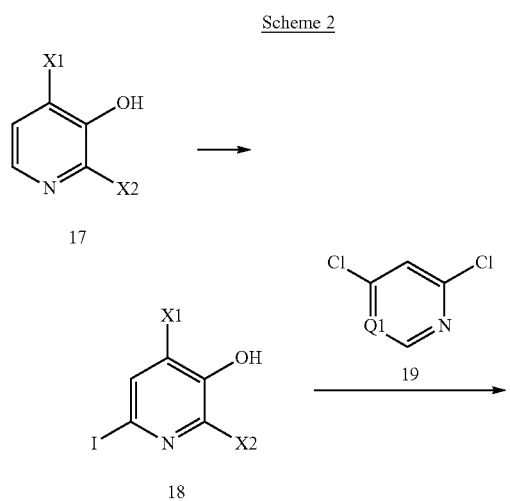

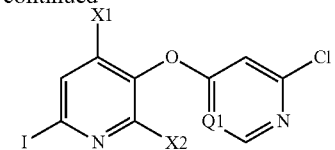

General amine 10 can be prepared as illustrated in Scheme 3 by alternate reaction sequences, the selection of which will influenced by the nature of the W-moiety. In one embodiment, intermediate 20 (Y is halogen) is reacted with 21 in the presence of a base, for example potassium carbonate to provide the nitro ether 22. Reduction of the nitro moiety of 22 provides 23. Conditions to effect the conversion of 22 to 23 are known by those skilled in the art and include the use of zinc powder in the presence of ammonium chloride in a protic solvent such as methanol. Further reaction of 23 with M-W (5) as described above provides 10. In an alternative embodiment, 22 can be reacted with M-W (5) as described above to provide 24. Reduction of the nitro moiety of 24 provides 10. In another embodiment, amines of formula 23 can be prepared directly by reaction of 25 with 19 in the presence of a base.

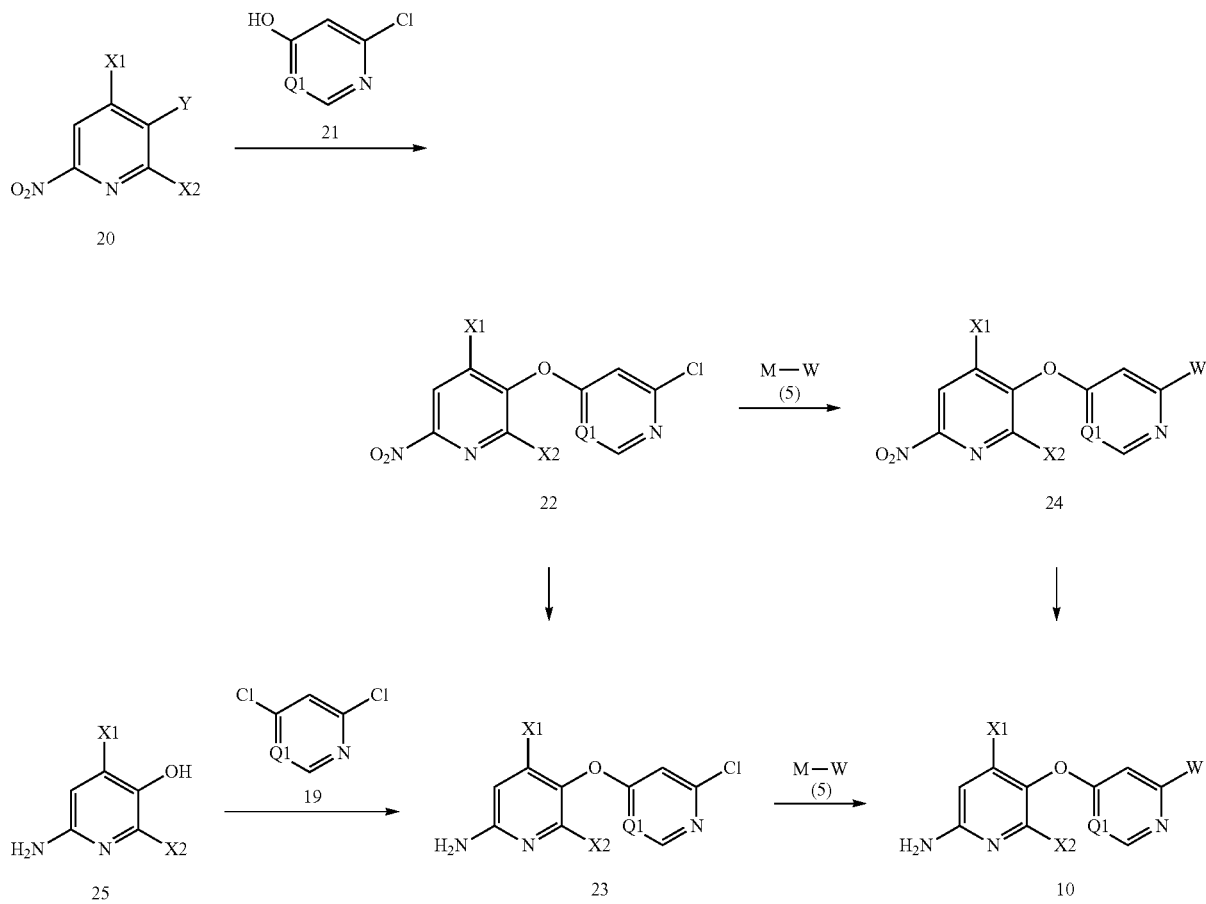

Scheme 4 illustrates the preparation of Compounds 28, examples of Formula I wherein Y is NR4 and Z is CR11. In one embodiment, following the general procedures of Scheme 1, iodide 2 can react with 26 in the presence of copper(I) iodide and a suitable ligand, for example N,N-dimethylethane-1,2-diamine to afford 27. Further reaction of 27 with M-W (5) in the presence of a palladium catalyst and a base, as described in scheme 1, provides compounds of formula 28. In an alternate embodiment, compounds of formula 28 can be prepared directly from compounds of formula 9 by reaction with 26 in the presence of copper(I) iodide and a suitable ligand.

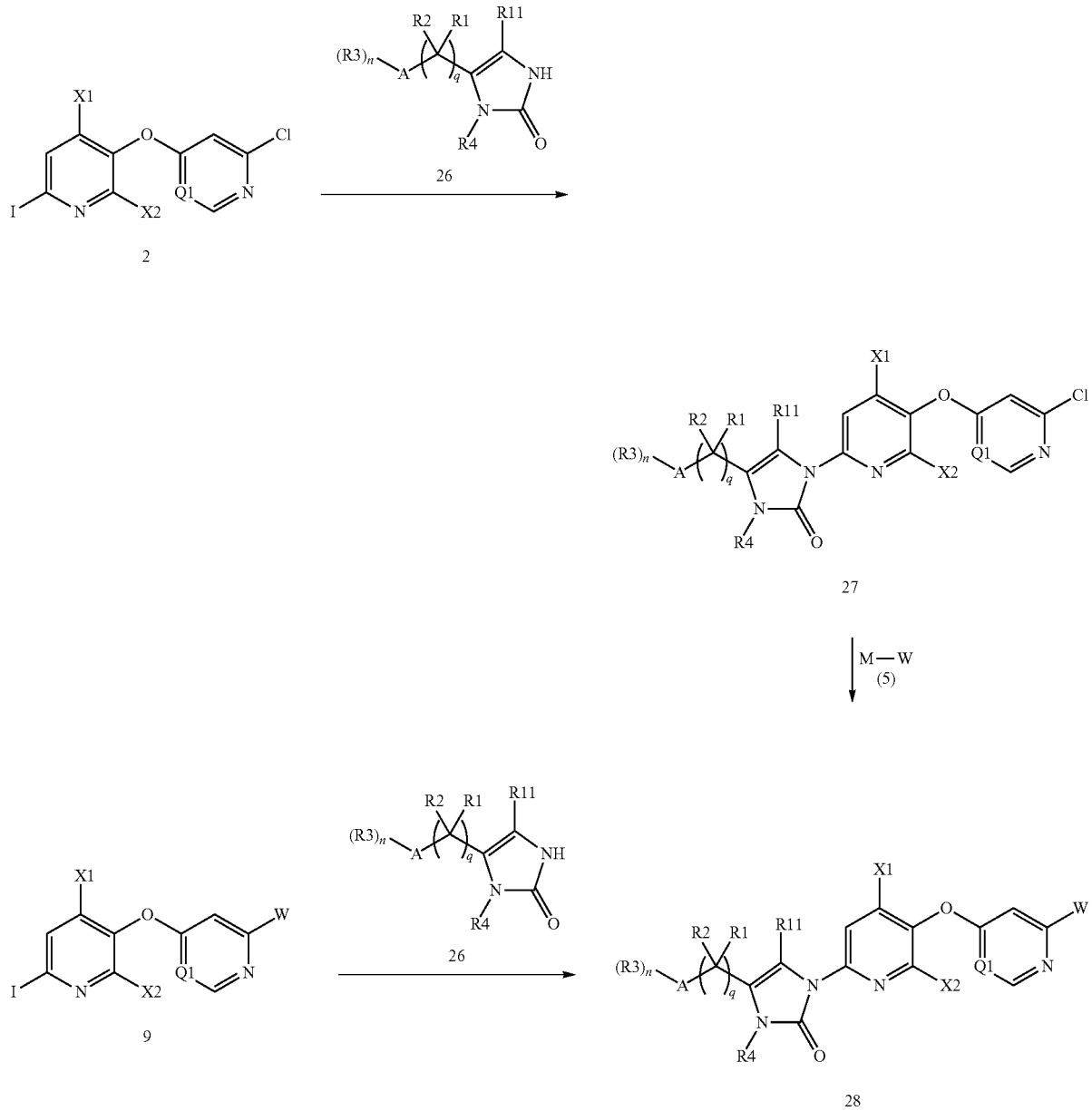

Scheme 5 illustrates the preparation of Compounds 31, examples of Formula I wherein Y is O and Z is N. Thus treatment of hydrazine 12 with acid chloride 29 provides compound 30. Those skilled in the art will appreciate that numerous equivalents for 29 may be found, including acid halides, anhydrides or "activated esters." Compound 30 may be isolated or generated and used in situ. Further reaction of 30 with triphosgene (or other suitable carbonylation reagent, such as phosgene or carbonyl diimidazole) in the presence of a base provides compounds of formula 31.

Scheme 5

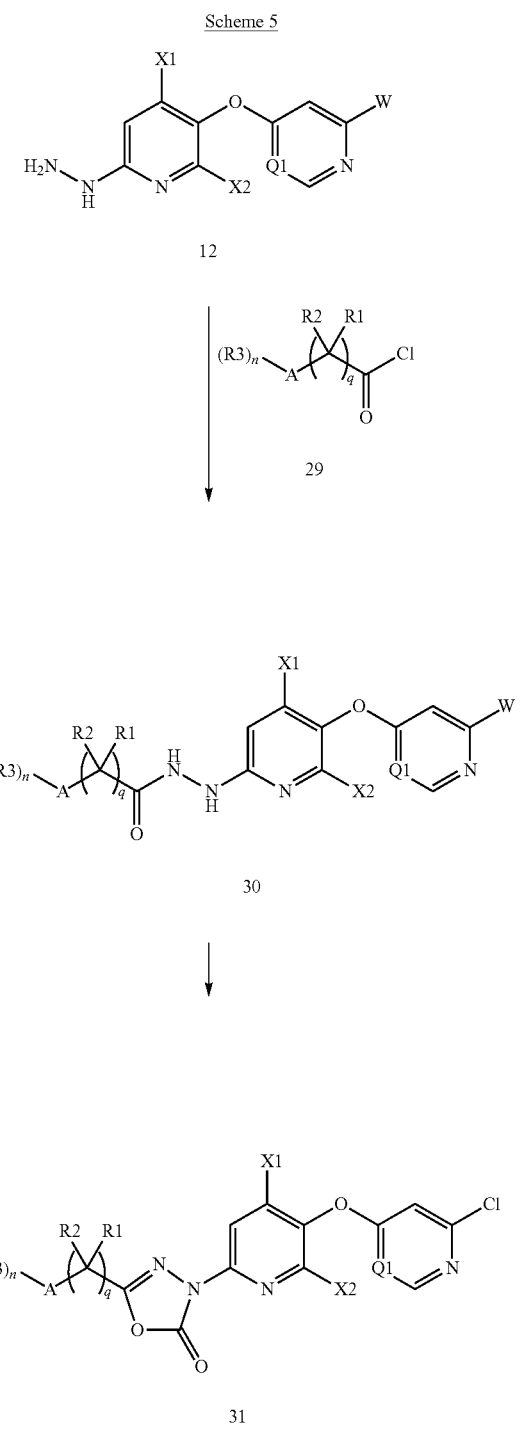

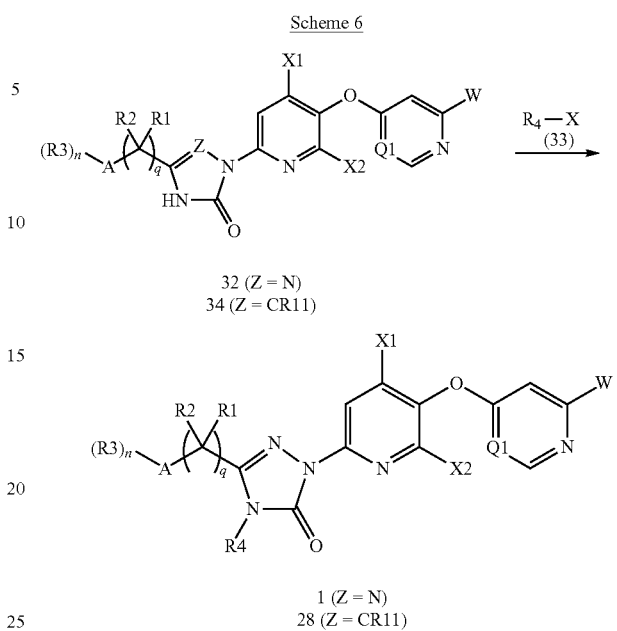

32 (Z = N)
34 (Z = CR11)

1 (Z = N)
28 (Z = CR11)

Scheme 7 illustrates a general preparation of triazolones of formula 35, examples of general reagent 3 wherein R4 is hydrogen. As indicated in scheme 7, reaction of acid chlorides 29 with semicarbazide (36) provide triazolones 35 after cyclodehydration of the intermediate 2-acylhydrazine-1 carboxamide 37. In one embodiment, the reaction is performed by treating an aqueous solution of semicarbazide with acid chloride 29 to afford 37 followed by the treatment of 37 with aqueous sodium hydroxide and the heating of the mixture to effect cyclodehydration. Those skilled in the art will appreciate that numerous equivalents for 29 may be found, including acid halides, anhydrides or "activated esters."

Scheme 7

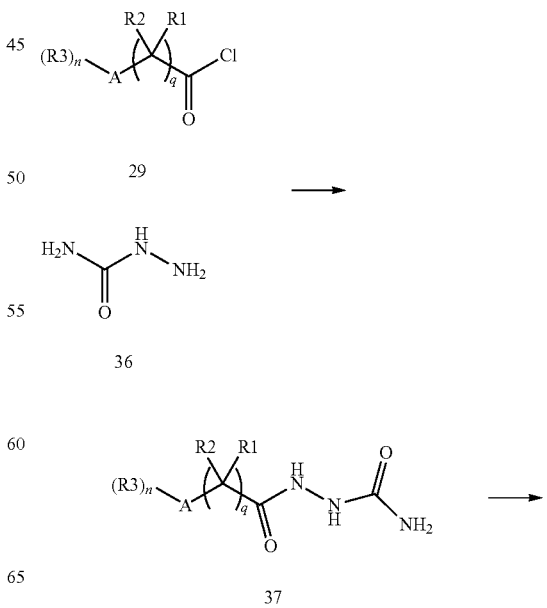

In another embodiment, Scheme 6 illustrates the preparation of compounds of Formula 1 or 28 wherein R4 is not hydrogen from compounds 32 or 34 respectively by alkylation of the NH moiety of 32 or 34 with an alkylating agent 33. Suitable conditions for the reaction include contacting alkylating agent 33 with 32 or 34 in an aprotic solvent, such as acetone, in the presence of a base, for example cesium carbonate or potassium carbonate. In one embodiment, 33 is an alkyl halide (X is halide). In another embodiment, 33 is a sulfonate ester, for example a triflate (Y=OS(O)$_2$CF$_3$).

-continued

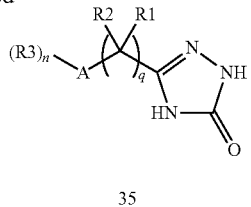

35

Using the synthetic procedures and methods described herein and methods known to those skilled in the art, the following compounds were made: 3-(4-fluorobenzyl)-1-(6-methyl-5-((2-(1-methyl-1H-pyrazol-4-yl)pyridin-4-yl)oxy)pyridin-2-yl)-1H-1,2,4-triazol-5(4H)-one, 3-benzyl-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorobenzyl)-1-(5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-methyl-1H-pyrazol-4-yl)pyridin-4-yl)oxy)pyridin-2-yl)-1H-1,2,4-triazol-5(4H)-one, 3-isopropyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclohexyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-ethyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2'-methyl-[2,4'-bipyridin]-4-yl)oxy)pyridin-2-yl)-1H-1,2,4-triazol-5(4H)-one, 3-(tert-butyl)-1-(6-methyl-5-46'-methyl-[2,3'-bipyridin]-4-yl)oxy)pyridin-2-yl)-1H-1,2,4-triazol-5(4H)-one, N-(4-((6-(3-(tert-butyl)-5-oxo-4,5-dihydro-1H-1,2,4-triazol-1-yl)-2-methylpyridin-3-yl)oxy)pyridin-2-yl) acetamide, 3-(tert-butyl)-1-(6-methyl-5-((2-(2-methylthiazol-5-yl)pyridin-4-yl)oxy)pyridin-2-yl)-1H-1,2,4-triazol-5(4H)-one, 3-(tert-butyl)-4-methyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(4-(1-methylpiperidin-4-yl)phenyl)pyridin-4-yl)oxy)pyridin-2-yl)-1H-1,2,4-triazol-5(4H)-one, 3-(2-methoxyethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(2-methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(methoxymethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-(2-hydroxyethyl)-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(4-methyl-1H-imidazol-1-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(tetrahydro-2H-pyran-4-yl)-1H-1,2,4-triazol-5(4H)-one, N-(4((6-(3-(tert-butyl)-5-oxo-4,5-dihydro-1H-1,2,4-triazol-1-yl)-2-methylpyridin-3-yl)oxy)pyridin-2-yl)-1-methylpiperidine-4-carboxamide, 3-isobutyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-imidazol-4-yl)pyridin-4-yl)oxy)pyridin-2-yl)-1H-1,2,4-triazol-5(4H)-one, 1-(5-((2-(1H-pyrazol-4-yl)pyridin-4-yl)oxy)-6-methylpyridin-2-yl)-3-(tert-butyl)-1H-1,2,4-triazol-5(4H)-one, 1-(6-methyl-5-((2-(1-methyl-1H-pyrazol-4-yl)pyridin-4-yl)oxy)pyridin-2-yl)-3-(tert-pentyl)-1H-1,2,4-triazol-5(4H)-one, 4-((6-(3-(tert-butyl)-5-oxo-4,5-dihydro-1H-1,2,4-triazol-1-yl)pyridin-3-yl)oxy)-N-methylpicolinamide, 1-(6-methyl-5-((2-(1-methyl-1H-pyrazol-4-yl)pyridin-4-yl)oxy)pyridin-2-yl)-3-(1-methylcyclopropyl)-1H-1,2,4-triazol-5(4H)-one, 3-(4-fluorophenyl)-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorophenyl)-1-(6-methyl-5-((2-(4-methyl-1H-imidazol-1-yl)pyridin-4-yl)oxy)pyridin-2-yl)-1H-1,2,4-triazol-5(4H)-one, 3-(4-((6-(3-(tert-butyl)-5-oxo-4,5-dihydro-1H-1,2,4-triazol-1-yl)-2-methylpyridin-3-yl)oxy)pyridin-2-yl)-1,1-dimethylurea, 3-(tert-butyl)-1-(4-methyl-5-((2-(1-methyl-1H-pyrazol-4-yl)pyridin-4-yl)oxy)pyridin-2-yl)-1H-1,2,4-triazol-5(4H)-one, N-(4-((6-(3-(4-fluorophenyl)-5-oxo-4,5-dihydro-1H-1,2,4-triazol-1-yl)-2-methylpyridin-3-yl)oxy)pyridin-2-yl) cyclopropanecarboxamide, 3-(tert-butyl)-1-(4,6-dimethyl-5-((2-(1-methyl-1H-pyrazol-4-yl)pyridin-4-yl)oxy)pyridin-2-yl)-1H-1,2,4-triazol-5(4H)-one, 3-cyclopentyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclopropyl-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-neopentyl-1H-1,2,4-triazol-5(4H)-one, 3-cyclobutyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-ethyl-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(oxazol-5-yl)pyridin-4-yl)oxy)pyridin-2-yl)-1H-1,2,4-triazol-5(4H)-one, 3-(tert-butyl)-1-(6-methyl-5-((6'-(4-methylpiperazin-1-yl)-[2,3'-bipyridin]-4-yl)oxy)pyridin-2-yl)-1H-1,2,4-triazol-5(4H)-one, 3-(tert-butyl)-1-(6-methyl-5-((2'-(4-methylpiperazin-1-yl)-[2,4'-bipyridin]-4-yl)oxy)pyridin-2-yl)-1H-1,2,4-triazol-5(4H)-one, 3-(1-hydroxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(1-(trifluoromethyl)cyclobutyl)-1H-1,2,4-triazol-5(4H)-one, N-(4-((6-(3-(2-methoxypropan-2-yl)-5-oxo-4,5-dihydro-1H-1,2,4-triazol-1-yl)-4-methylpyridin-3-yl)oxy)pyridin-2-yl)acetamide, N-(4-((6-(3-(tert-butyl)-5-oxo-4,5-dihydro-1H-1,2,4-triazol-1-yl)-2-methylpyridin-3-yl)oxy)pyridin-2-yl)cyclopropanecarboxamide, 3-(1-methoxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((6-(1-methyl-1H-pyrazol-4-yl)pyrimidin-4-yl)oxy)pyridin-2-yl)-1H-1,2,4-triazol-5(4H)-one, 4-(tert-butyl)-1-(6-methyl-5-((2-(1-methyl-1H-pyrazol-4-yl)pyridin-4-yl)oxy)pyridin-2-yl)-1H-imidazol-2(3H)-one, and 5-(tert-butyl)-3-(6-methyl-5-((2-(1-methyl-1H-pyrazol-4-yl)pyridin-4-yl)oxy)pyridin-2-yl)-1,3,4-oxadiazol-2(3H)-one.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

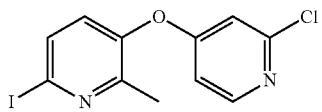 [SMILES: Cc1nc(I)ccc1Oc1ccnc(Cl)c1]

Example A1

A solution of 3-hydroxy-2-methylpyridine (20.0 g, 183 mmol) and Na$_2$CO$_3$ (38.8 g, 367 mmol) in H$_2$O (320 mL) and MeOH (200 mL) was treated with I$_2$ (46.5 g, 183 mmol) and stirred at RT for 1 h. The mixture was acidified with HCl (2 M), extracted with EtOAc (2×) and the combined organics were washed with brine, dried over Na$_2$SO$_4$ and concentrated to dryness. The material was suspended in 1:1 EtOAc/Hex, sonicated and the solid collected via filtration and dried. The filtrate was concentrated to dryness, treated with DCM, the solid collected via filtration and combined with the first solid to afford 6-iodo-2-methylpyridin-3-ol (20.5 g, 48%). MS (ESI) m/z: 236.0 (M+H$^+$).

A mixture of 6-iodo-2-methylpyridin-3-ol (6.8 g, 28.9 mmol), 2,4-dichloropyridine (8.56 g, 57.9 mmol) and K$_2$CO$_3$ (4.00 g, 28.9 mmol) in DMA (50 mL) was heated at 110° C. for 16 h under argon. The mixture was cooled to RT, treated with H$_2$O, extracted with EtOAc (2×) and the combined organics were washed with H$_2$O, then brine, dried over Na$_2$SO$_4$, concentrated to dryness and purified via silica gel chromatography (EtOAc/Hex) to afford 34(2-chloropyridin-4-yl)oxy)-6-iodo-2-methylpyridine (7.35 g, 73%) as a white solid. MS (ESI) m/z: 346.9 (M+H$^+$).

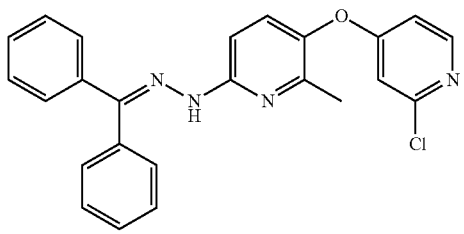 [SMILES: Cc1nc(NN=C(c2ccccc2)c2ccccc2)ccc1Oc1ccnc(Cl)c1]

Example A2

A mixture of Example A1 (10.0 g, 28.9 mmol), benzophenone hydrazone (5.46 g, 27.8 mmol), 2,2'-bis(diphenylphosphino)-1,1'-binaphthalene (1.13 g, 1.82 mmol), and sodium tert-butoxide (3.90 g, 40.6 mmol) in toluene (57.7 mL) was sonicated and sparged with Ar for 10 min. Palladium(II) acetate (0.14 g, 0.61 mmol) was added and the reaction mixture was stirred vigorously at 105° C. for 16 h. The mixture was diluted with EtOAc (50 mL) and filtered through a pad of diatomaceous earth. The filter cake was washed with EtOAc (3×10 mL) and the combined filtrates were concentrated in vacuo. The residue was purified by silica gel chromatography (EtOAc/hexanes) to afford 3-((2-chloropyridin-4-yl)oxy)-6-(2-(diphenylmethylene)hydrazinyl)-2-methylpyridine (4.3 g, 100% yield) as a white solid. $^1$H NMR (400 MHz, DMSO-d$_6$): δ 8.37 (s, 1H), 8.26 (d, J=5.8 Hz, 1H), 7.64-7.63 (m, 1H), 7.57-7.56 (m, 2H), 7.37-7.33 (m, 8H), 6.96 (d, J=2.3 Hz, 1H), 6.90 (dd, J=5.8, 2.3 Hz, 1H), 2.09 (s, 3H); MS (ESI) m/z: 415.1 (M+H$^+$).

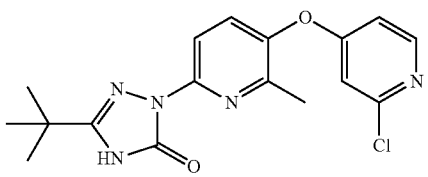 [SMILES: Cc1nc(-n2nc(C(C)(C)C)[nH]c2=O)ccc1Oc1ccnc(Cl)c1]

Example A3

Method 1: Concentrated HCl (21.31 mL, 256 mmol) was added to a solution of Example A2 (4.2 g, 10.1 mmol) in toluene (80 mL) and the reaction mixture was stirred at 110° C. for 1.5 h. The organic solvent was removed in vacuo and the remaining aqueous solution was diluted with water (50 mL), washed with toluene (2×20 mL), cooled in an ice bath, and adjusted to pH ~12 with 50% NaOH (aq). The suspension was saturated with solid NaCl and extracted with EtOAc (3×50 mL). The combined organics were dried (Na$_2$SO$_4$) and concentrated in vacuo to afford 3-((2-chloropyridin-4-yl)oxy)-6-hydrazinyl-2-methylpyridine (2.1 g, 83%) as a white solid. $^1$H NMR (400 MHz, DMSO-d$_6$): δ 8.24 (d, J=5.7 Hz, 1H), 7.50 (s, 1H), 7.30 (d, J=8.8 Hz, 1H), 6.88 (d, J=2.2 Hz, 1H), 6.85-6.84 (m, 1H), 6.63 (d, J=9.0 Hz, 1H), 4.13 (br s, 2H), 2.09 (s, 3H); MS (ESI) m/z: 251.1 (M+H$^+$).

3((2-Chloropyridin-4-yl)oxy)-6-hydrazinyl-2-methylpyridine (2.0 g, 8.0 mmol) was suspended in DCM (14 mL) at 0° C. Example B3 (2.7 g, 16.3 mmol) was added and the mixture was allowed to warm to RT and stirred for 25 min. The mixture was cooled back to 0° C. and diluted with DCM (70 mL). TEA (5.6 mL, 40.2 mmol) and a solution of bis(trichloromethyl) carbonate (1.2 g, 4.0 mmol) in DCM (10 mL) were sequentially added and the mixture was allowed to warm to RT and stirred for 30 min. Sat. NaHCO$_3$ (aq) (100 mL) was added the mixture was extracted with DCM (4×50 mL). The combined organics were dried (MgSO$_4$) and concentrated in vacuo. The residue was purified by silica gel chromatography (MeOH/DCM) to afford 3-(tert-butyl)-1-(5-((2-chloropyridin-4-yl)oxy)-6-methylpyridin-2-yl)-1H-1,2,4-triazol-5 (4H)-one (1.25 g, 43.5%) as an off white solid. $^1$H NMR (400 MHz, DMSO-d$_6$): δ 11.97 (s, 1H), 8.29 (d, J=5.8 Hz, 1H), 7.86 (d, J=8.8 Hz, 1H), 7.73 (d, J=8.8 Hz, 1H), 7.06 (d, J=2.3 Hz, 1H), 6.96 (dd, J=5.8, 2.3 Hz, 1H), 2.30 (s, 3H), 1.27 (s, 9H); MS (ESI) m/z: 360.1 (M+H$^+$).

Method 2: A suspension of Example C1 (7.00 g, 49.6 mmol), Example A1 (13.00 g, 37.5 mmol), copper iodide (0.700 g, 3.68 mmol), K$_2$CO$_3$ (10.00 g, 72.4 mmol) and N1,N2-dimethylethane-1,2-diamine (0.700 g, 7.94 mmol) in DMF (70 mL) was heated at 100° C. under argon overnight.

The solvent from the reaction mixture was evaporated under vacuum. The residue was partitioned between DCM (300 mL) and water (300 mL). The organic layer was separated and the aqueous layer extracted with DCM (2×200 mL). The combined organics were washed with brine, dried and evaporated. The residue was subjected to chromatography using (0-20% MeOH/DCM) to provide 3-(tert-butyl)-1-(5-((2-chloropyridin-4-yl)oxy)-6-methylpyridin-2-yl)-1H-1,2,4-triazol-5(4H)-one, (6.7 g, 49.6%) as a white solid. MS (ESI) m/z: 360.2 (M+H$^+$).

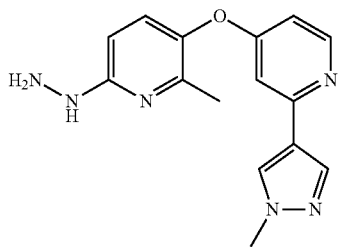 [SMILES: Cc1nc(NN)ccc1Oc1ccnc(-c2cnn(C)c2)c1]

Example A4

Example A2 (9.2 g, 22.9 mmol) and 1-methyl-4-(4,4,5,5-tetramethyl-1,3,2-dioxaborolan-2-yl)-1H-pyrazole (6.2 g, 29.8 mmol) were dissolved in dioxane (92 mL). A solution of $K_2CO_3$ (9.0 g, 65.1 mmol) in water (22.9 mL) was added and the mixture was sonicated and sparged with Ar for 10 min. Tetrakis(triphenylphosphine)-palladium(0) [Pd(PPh$_3$)$_4$] (1.4 g, 1.2 mmol) was added and the reaction mixture was stirred at 85° C. for 16 h. The mixture was partitioned between water (250 mL) and DCM (200 mL). The organic phase was collected and the aqueous phase was extracted with DCM (4×100 mL). The combined organics were dried (Na$_2$SO$_4$) and concentrated in vacuo. The residue was purified by silica gel chromatography (MeOH/DCM) to afford 6-(2-(diphenyl-methylene)hydrazinyl)-2-methyl-3-((2-(1-methyl-1H-pyrazol-4-yl)pyridin-4-yl)oxy)pyridine (9.3 g, 88%) as a light yellow solid. $^1$H NMR (400 MHz, DMSO-d$_6$): δ 8.33 (d, J=5.1 Hz, 2H), 8.24 (s, 1H), 7.94 (s, 1H), 7.58-7.57 (m, 6H), 7.38-7.36 (m, 6H), 7.12 (d, J=2.5 Hz, 1H), 6.58 (dd, J=5.7, 2.4 Hz, 1H), 3.84 (s, 3H), 2.12 (s, 3H); MS (ESI) m/z: 461.2 (M+H$^+$).

6-(2-(Diphenylmethylene)hydrazinyl)-2-methyl-3-((2-(1-methyl-1H-pyrazol-4-yl)pyridin-4-yl)oxy)pyridine (9.3 g, 20.19 mmol) was dissolved in toluene (497 mL). Concentrated HCl (134 mL, 1608 mmol) was added and the reaction mixture was stirred for 1.5 h at 110° C., allowed to cool to RT, and stirred for 10 h. The organic phase was removed and the aqueous phase was extracted with toluene (1×100 mL). The combined organics were back extracted with 1 N HCl (1×100 mL). The combined aqueous phases were adjusted to pH ~11 with 50% NaOH (aq), saturated with solid NaCl, and extracted with EtOAc (3×200 mL). The combined organics were dried (Na$_2$SO$_4$) and concentrated in vacuo to afford 6-hydrazinyl-2-methyl-3-((2-(1-methyl-1H-pyrazol-4-yl) pyridin-4-yl)oxy)pyridine (4.7 g, 79%) as a tan solid. $^1$H NMR (400 MHz, DMSO-d$_6$): δ 8.31 (d, J=5.7 Hz, 1H), 8.22 (s, 1H), 7.92 (s, 1H), 7.44 (s, 1H), 7.28 (d, J=8.8 Hz, 1H), 7.11 (d, J=2.4 Hz, 1H), 6.64 (d, J=8.8 Hz, 1H), 6.49 (dd, J=5.7, 2.4 Hz, 1H), 4.14 (s, 2H), 3.84 (s, 3H), 2.11 (s, 3H); MS (ESI) m/z: 297.1 (M+H$^+$).

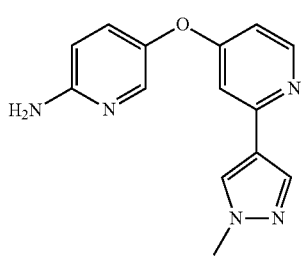 [SMILES: Cn1cc(-c2cc(Oc3ccc(N)nc3)ccn2)cn1]

Example A5

A solution of 5-bromo-2-nitropyridine (15 g, 73.9 mmol) in DMF (300 mL) was sparged with Ar, treated with Cs$_2$CO$_3$ (48.2 g, 148 mmol) and 2-chloro-4-hydroxypyridine (10.53 g, 81 mmol), sparged again with Ar and heated at 85° C. overnight. The mixture was cooled to RT, filtered through a bed of silica gel, washed thoroughly with EtOAc, and the filtrate treated with 5% LiCl and stirred overnight. The layers were separated, the aqueous layer extracted with additional EtOAc (4×) and the combined organics were dried over Na$_2$SO$_4$ and concentrated to dryness. The residue was dissolved in EtOAc, treated with 5% LiCl, stirred for 1 h, the layers separated and the aqueous layer extracted with EtOAc (3×). The combined organics were dried over Na$_2$SO$_4$, concentrated to dryness and purified via silica gel chromatography (EtOAc/Hex). The material was suspended in MTBE, sonicated and the resulting solid collected via filtration to afford 2-chloro-4-((6-nitropyridin-3-yl)oxy)pyridine (6.06 g, 33%). $^1$H NMR (400 MHz, DMSO-d$_6$): δ 8.62 (d, J=2.4, 1H), 8.43-8.39 (m, 2H), 8.06 (dd, J=8.8, 2.8 Hz, 1H), 7.36 (d, J=2.0 Hz, 1H), 7.23 (dd, J=5.6, 2.0 Hz, 1H); MS (ESI) m/z: 252.0 (M+H$^+$).

A suspension of 2-chloro-4-((6-nitropyridin-3-yl)oxy)pyridine (14.38 g, 57.1 mmol), 1-methyl-4-(4,4,5,5-tetramethyl-1,3,2-dioxaborolan-2-yl)-1H-pyrazole (13.08 g, 62.9 mmol) and Cs$_2$CO$_3$ (55.9 g, 171 mmol) in DMF (150 mL) was sparged with Ar, treated with Pd(PPh$_3$)$_4$ (6.60 g, 5.71 mmol), sparged again with Ar and heated at 90° C. overnight. The mixture was cooled to RT, the solids removed via filtration through diatomaceous earth, washed with EtOAc and the filtrate concentrated to near-dryness. The residue was treated with EtOAc, washed with 5% LiCl (1×) and the aqueous layer back-extracted with EtOAc (4×). The combined organics were dried over Na$_2$SO$_4$, concentrated to dryness and purified via silica gel chromatography (MeOH/DCM) to afford 2-(1-methyl-1H-pyrazol-4-yl)-4-((6-nitropyridin-3-yl)oxy)pyridine (12.28 g, 72%). $^1$H NMR (400 MHz, DMSO-d$_6$): δ 8.59 (d, J=2.8 Hz, 1H), 8.49 (d, J=5.6 Hz, 1H), 8.41 (d, J=8.9 Hz, 1H), 8.29 (s, 1H), 8.00 (d, J=0.7 Hz, 1H), 7.97 (dd, J=8.9, 2.8 Hz, 1H), 7.44 (d, J=2.4 Hz, 1H), 6.97 (dd, J=5.6, 2.4 Hz, 1H), 3.85 (s, 3H); MS (ESI) m/z: 298.1 (M+H$^+$).

A mixture of 2-(1-methyl-1H-pyrazol-4-yl)-4-((6-nitropyridin-3-yl)oxy)pyridine (11.88 g, 40.0 mmol) and NH$_4$Cl (22.4 g, 419 mmol) in EtOH (200 mL) and water (200 mL) was treated portion-wise with iron powder (22.4 g, 401 mmol), stirred for 0.5 h, treated with additional NH$_4$Cl (22.4 g, 419 mmol) and iron powder (22.4 g, 401 mmol) and stirred at RT for 3 h. The solids were removed via filtration through diatomaceous earth and washed with EtOAc and DCM. The filtrate was washed with water, the aqueous layer back-extracted with DCM (4×) and the combined organics were dried over Na$_2$SO$_4$, concentrated to dryness and purified via silica gel chromatography (MeOH/DCM) to afford 54(2-(1-methyl-1H-pyrazol-4-yl)pyridin-4-yl)oxy)pyridin-2-amine (6.4 g, 60%). MS (ESI) m/z: 268.1 (M+H+).

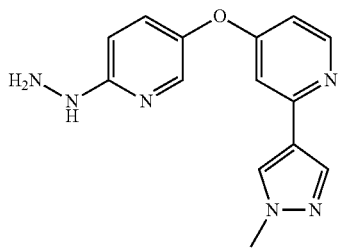 [SMILES: Cn1cc(-c2cc(Oc3ccc(NN)nc3)ccn2)cn1]

Example A6

Example A5 (1.0 g, 3.8 mmol) was added to a solution of HF-pyridine (5.6 mL, 62.0 mmol) in pyridine (5.6 mL) at 0° C. The mixture was stirred for 30 min, cooled to −10° C., and treated with sodium nitrite (0.39 g, 5.6 mmol). The mixture was allowed to warm to RT, stirred for 12 h, cooled back to 0° C., and poured into cold sat. NaHCO₃ (aq) (50 mL). The slurry was extracted with EtOAc (3×50 mL) and the combined organics were dried (Na₂SO₄) and concentrated in vacuo. The residue was purified by silica gel chromatography (MeOH/DCM) to afford 4-((6-fluoropyridin-3-yl)oxy)-2-(1-methyl-1H-pyrazol-4-yl)pyridine (0.99 g, 98%) as a white solid. MS (ESI) m/z: 271.1 (M+H⁺).

4-((6-Fluoropyridin-3-yl)oxy)-2-(1-methyl-1H-pyrazol-4-yl)pyridine (0.99 g, 3.66 mmol) was dissolved in 2-propanol (7.3 mL) in a screw-cap reaction vessel. Hydrazine hydrate (64%) (0.9 mL, 18.3 mmol) was added, the vessel was sealed, and the reaction mixture was stirred at 80° C. for 12 h. The mixture was partitioned between sat. aqueous NaHCO₃ (aq) (30 mL) and EtOAc (30 mL). The organic phase was collected and the aqueous phase was extracted with EtOAc (4×30 mL). The combined organics were dried (Na₂SO₄) and concentrated in vacuo to afford 4-((6-hydrazinylpyridin-3-yl)oxy)-2-(1-methyl-1H-pyrazol-4-yl)pyridine (0.9 g, 87%) as an off-white solid. ¹H NMR (400 MHz, DMSO-d₆): δ 9.29 (s, 1H), 8.33 (d, J=5.7 Hz, 1H), 8.23 (s, 1H), 8.00 (d, J=2.9 Hz, 1H), 7.93 (s, 1H), 7.48 (dd, J=9.0, 2.9 Hz, 1H), 7.16 (d, J=2.4 Hz, 1H), 7.12 (d, J=9.0 Hz, 1H), 6.62 (dd, J=5.7, 2.4 Hz, 1H), 4.10 (d, J=4.5 Hz, 2H), 3.84 (s, 3H); MS (ESI) m/z: 283.1 (M+H⁺).

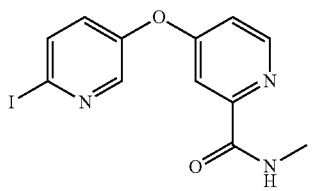 [SMILES: CNC(=O)c1cc(Oc2ccc(I)nc2)ccn1]

Example A7

DMF (25 mL) was slowly treated with SOCl₂ (125 mL) to maintain a temperature of 40-50° C. The mixture was then treated portion-wise with pyridine-2-carboxylic acid (25 g, 0.2 mol) over 0.5 h, then heated at reflux for 16 h, cooled to RT, diluted with toluene (80 mL) and concentrated to dryness (this process was repeated three times). The resulting residue was washed with toluene and dried under reduced pressure to yield 4-chloro-pyridine-2-carbonyl chloride (27.6 g, 79% yield), which was used in the next step without purification.

A 0° C. solution of 4-chloro-pyridine-2-carbonyl chloride (27.6 g, 0.16 mol) in THF (100 mL) at was treated drop-wise with a solution of MeNH₂ in EtOH, stirred at 3° C. for 4 h, then concentrated to dryness. The material was suspended in EtOAc, the solids removed via filtration and the filtrate was washed with brine (2×), dried and concentrated to yield 4-chloro-N-methylpicolinamide (16.4 g, 60%) as a yellow solid. ¹H NMR (400 MHz, DMSO-d₆) δ 8.78 (br s, 1H), 8.55 (d, J=5.2 Hz, 1H), 7.97 (d, J=2.0 Hz, 1H), 7.66 (m, 1H), 2.82 (d, J=4.8 Hz, 3H); MS (ESI) m/z: 171.0 (M+H⁺).

A solution of 2-amino-5-hydroxypyridine (0.968 g, 8.79 mmol) in DMA (15 mL) was treated with potassium tert-butoxide (0.987 g, 8.79 mmol), stirred at RT for 3 h, treated with 4-chloro-N-methylpicolinamide (1.5 g, 8.79 mmol) and stirred at RT for 2 days. The mixture was concentrated to dryness, treated with water, extracted with EtOAc (3×) and the combined organics were washed with brine, dried over Na₂SO₄, concentrated to dryness and purified via silica gel chromatography (EtOAc, MeOH/DCM) to afford 4-((6-aminopyridin-3-yl)oxy)-N-methylpicolinamide (1.3 g, 61%). ¹H NMR (400 MHz, DMSO-d₆): δ 8.75 (m, 1H), 8.46 (d, J=5.6 Hz, 1H), 7.82 (d, J=2.9 Hz, 1H), 7.34 (d, J=2.6 Hz, 1H), 7.30 (dd, J=8.9, 3.0 Hz, 1H), 7.10 (dd, J=5.6, 2.7 Hz, 1H), 6.53 (d, J=8.9 Hz, 1H), 6.07 (s, 2H), 2.77 (d, J=4.8 Hz, 3H); MS (ESI) m/z: 245.1 (M+H⁺).

A mixture of 4-((6-aminopyridin-3-yl)oxy)-N-methylpicolinamide (0.4 g, 1.64 mmol) and potassium iodide (1.36 g, 8.19 mmol) in methylene iodide (5.46 mL) was treated drop-wise with t-butylnitrite (1.95 mL, 16.4 mmol). The mixture was stirred overnight at RT, diluted with EtOAc (75 mL), and washed with 10% sodium carbonate (50 mL), 10% thiosulfate (50 mL), and brine (50 mL). The organics were dried over sodium sulfate, evaporated to dryness and purified by silica gel chromatography ((EtOAc/Hex) to afford 4-((6-iodopyridin-3-yl)oxy)-N-methylpicolinamide (0.214 g, 36.8%). ¹H NMR (400 MHz, DMSO-d₆): δ 8.78 (br d, J=5.6 Hz, 1H), 8.54 (d, J=5.6 Hz, 1H), 8.40 (d, J=3.0 Hz, 1H), 7.95 (d, J=8.6 Hz, 1H), 7.50 (dd, J=8.6, 3.1 Hz, 1H), 7.45 (d, J=2.6 Hz, 1H), 7.23 (dd, J=5.6, 2.7 Hz, 1H), 2.78 (d, J=4.9 Hz, 3H); MS (ESI) m/z: 356.0 (M+H⁺).

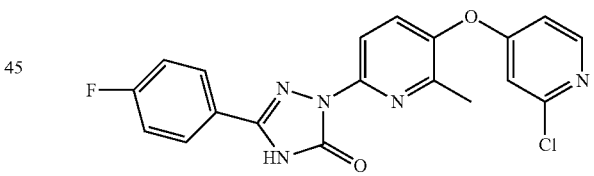

Example A8

A suspension of Example C5 (0.75 g, 4.19 mmol), Example A1 (1.400 g, 4.04 mmol), copper iodide (0.080 g, 0.420 mmol), trans 1,2-dimethylcyclohexane-1,2-diamine (0.090 g, 0.633 mmol) and K₂CO₃ (1.00 g, 7.24 mmol) in DMF (15 mL) was briefly degassed and heated at 100° C. under argon for 8 hours. The residue was partitioned between dichloromethane (50 mL) and water (50 mL). The aqueous layer was separated and extracted with DCM (2×30 mL). The combined organics were dried and concentrated to a small volume and subjected to chromatography using (0-100% EtOAc/DCM) to provide 1-(5-((2-chloropyridin-4-yl)oxy)-6-methylpyridin-2-yl)-3-(4-fluorophenyl)-1H-1,2,4-triazol-5(4H)-one (1.01 g, 63%) as a white solid. ¹H NMR (400 MHz, DMSO-d₆): δ 12.70 (s, 1H), 8.30 (d, J=5.8 Hz, 1H), 7.97-7.93 (m, 3H), 7.78 (d, J=8.8 Hz, 1H), 7.39 (m, 2H), 7.08 (d, J=2.2 Hz, 1H), 6.98 (dd, J=5.8, 2.3 Hz, 1H), 2.34 (s, 3H); MS (ESI) m/z: 398.1 (M+H⁺).

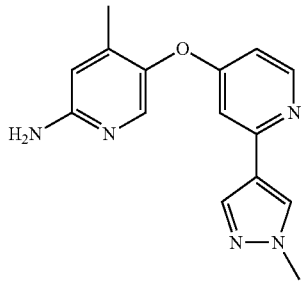 [SMILES: Cc1cc(N)ncc1Oc1ccnc(-c2cnn(C)c2)c1]

Example A9

A 0° C. solution of H₂SO₄ (12 mL) was treated with H₂O₂ (9.72 mL, 95 mmol), stirred for 10 min, treated with a solution of 2-amino-5-fluoro-4-methylpyridine (2 g, 15.86 mmol) in H₂SO₄ (8 mL), stirred for 15 min, then warmed to RT and stirred for 3 h. The mixture was re-cooled to 0° C., neutralized slowly with solid NaHCO₃ and the resulting solid collected via filtration and dried to afford 5-fluoro-4-methyl-2-nitropyridine (2 g, 81%). ¹H NMR (400 MHz, DMSO-d₆): δ 8.57 (s, 1H), 8.42 (d, J=5.3 Hz, 1H), 2.42 (d, J=1.9 Hz, 3H); MS (ESI) m/z: 157.1 (M+H⁺).

A mixture of 5-fluoro-4-methyl-2-nitropyridine (2 g, 12.81 mmol) and 2-chloro-4-hydroxypyridine (1.66 g, 12.81 mmol) in DMF (26 mL) was sparged with Ar, treated with K₂CO₃ (2.66 g, 19.22 mmol), heated at 88° C. for 24 h, then at 50° C. for 2 days. The mixture was treated with water and the resulting solid collected via filtration and dried to afford 5-((2-chloropyridin-4-yl)oxy)-4-methyl-2-nitropyridine (2.72 g, 80%). ¹H NMR (400 MHz, DMSO-d₆): δ 8.49 (s, 1H), 8.47 (s, 1H), 8.35 (d, J=5.7 Hz, 1H), 7.24 (d, J=2.3 Hz, 1H), 7.12 (dd, J=5.7, 2.3 Hz, 1H), 2.32 (s, 3H); MS (ESI) m/z: 266.0 (M+H⁺).

A solution of 5-((2-chloropyridin-4-yl)oxy)-4-methyl-2-nitropyridine (1.5 g, 5.65 mmol) and 1-methyl-4-(4,4,5,5-tetramethyl-1,3,2-dioxaborolan-2-yl)-1H-pyrazole (1.527 g, 7.34 mmol) in dioxane (20 mL) was sparged with Ar, treated with a solution of K₂CO₃ (1.171 g, 8.47 mmol) in water (5 mL) and Pd(PPh₃)₄ (0.326 g, 0.282 mmol) and heated at 80° C. overnight. The mixture was cooled to RT, treated with water, extracted with DCM (4×) and the combined organics were dried over Na₂SO₄, concentrated to dryness and purified via silica gel chromatography (MeOH/DCM) to afford 4-methyl-5-((2-(1-methyl-1H-pyrazol-4-yl)pyridin-4-yl)oxy)-2-nitropyridine (2.3 g, 75%). ¹H NMR (400 MHz, DMSO-d₆): δ 8.48 (s, 1H), 8.43-8.42 (m, 2H), 8.27 (s, 1H), 7.98 (s, 1H), 7.30 (d, J=2.4 Hz, 1H), 6.83 (dd, J=5.7, 2.4 Hz, 1H), 3.84 (s, 3H), 2.34 (s, 3H); MS (ESI) m/z: 312.1 (M+H⁺).

A solution of 4-methyl-5-((2-(1-methyl-1H-pyrazol-4-yl)pyridin-4-yl)oxy)-2-nitropyridine (2.3 g, 7.39 mmol) in MeOH (37 mL) and THF (37 mL) was treated with NH₄Cl (11.86 g, 222 mmol) followed by the portion-wise addition of zinc dust (4.83 g, 73.9 mmol) and the mixture stirred at RT overnight. The mixture was diluted with EtOAc, the solids removed via filtration through diatomaceous earth and the filtrate concentrated to dryness and purified via silica gel chromatography (MeOH/DCM) to afford 4-methyl-5-((2-(1-methyl-1H-pyrazol-4-yl)pyridin-4-yl)oxy)pyridin-2-amine (1.4 g, 67%). MS (ESI) m/z: 282.1 (M+H⁺).

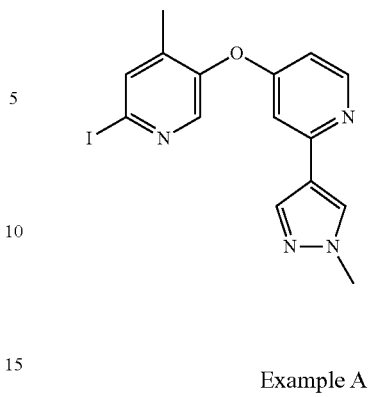

Example A10

A suspension of Example A9 (0.62 g, 2.2 mmol), KI (3.7 g, 22.3 mmol), and diiodomethane (5 mL, 62 mmol) was treated with t-butylnitrite (1.4 mL, 11.7 mmol) and stirred at RT for 12 h. The mixture was treated with EtOAc, washed successively with satd. NaHCO₃ (3×), 10% Na₂S₂O₃ (2×), and brine (2×) and the combined aqueous washes were back-extracted with EtOAc (2×). The combined organics were dried over MgSO₄, concentrated to dryness and purified by silica gel chromatography (EtOAc/DCM) to afford 2-iodo-4-methyl-5-((2-(1-methyl-1H-pyrazol-4-yl)pyridin-4-yl)oxy)pyridine (0.51 g, 59%). MS (ESI) m/z: 393.0 (M+H⁺).

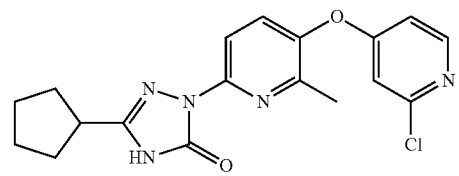 [SMILES: Cc1nc(-n2nc(C3CCCC3)[nH]c2=O)ccc1Oc1ccnc(Cl)c1]

Example A11

A suspension of Example C6 (0.800 g, 5.22 mmol), Example A1 (1.00 g, 2.89 mmol), copper iodide (0.050 g, 0.263 mmol), Cs₂CO₃ (2.000 g, 6.14 mmol) and N1,N2-dimethylethane-1,2-diamine (0.050 g, 0.567 mmol) in acetonitrile (20 mL) was heated at 100° C. under argon for 14 hours. The solvent from the reaction mixture was evaporated and the residue was partitioned between DCM (50 mL) and water (50 mL) The organic layer was separated and the aqueous layer saturated with solid sodium chloride and extracted with DCM (2×20 mL). The combined organics were dried, concentrated and purified by silica gel chromatography using (0-100% EtOAc/DCM) to provide 1-(5-((2-chloropyridin-4-yl)oxy)-6-methylpyridin-2-yl)-3-cyclopentyl-1H-1,2,4-triazol-5(4H)-one (0.342 g, 32% yield) as white solid. ¹H NMR (400 MHz, DMSO-d₆): δ 11.92 (s, 1H), 8.29 (d, J=5.8 Hz, 1H), 7.88 (d, J=8.8 Hz, 1H), 7.73 (d, J=8.8 Hz, 1H), 7.06 (d, J=2.3 Hz, 1H), 6.95 (dd, J=5.8, 2.3 Hz, 1H), 2.95 (m, 1H), 2.29 (s, 3H), 1.94 (m, 2H), 1.62 (m, 6H); MS (ESI) m/z: 372.1 (M+H⁺).

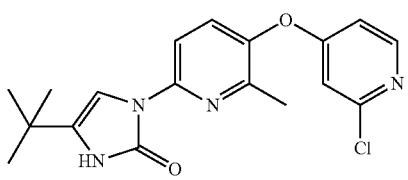 [SMILES: Cc1nc(-n2cc(C(C)(C)C)[nH]c2=O)ccc1Oc1ccnc(Cl)c1]

Example A12

4-(tert-butyl)-1H-imidazol-2(3H)-one (3 g, 21.40 mmol), copper(I) iodide (0.815 g, 4.28 mmol), and $K_2CO_3$ (16.33 g, 118 mmol) were suspended in DMF (100 mL) and placed under an atmosphere of argon. Example A1 (8.16 g, 23.54 mmol) and then N,N-dimethylethane-1,2-diamine (0.377 g, 4.28 mmol) were added and the reaction mixture was stirred at 100° C. overnight. The reaction mixture was allowed to cool to RT and concentrated to dryness under high vacuum. The residue was stirred with sat'd $NH_4Cl$ and EtOAc for ~60 minutes and the aqueous layer separated and back-extracted with EtOAc (3×). The organic phases were combined, dried ($Na_2SO_4$), concentrated to dryness and dried further under high vacuum for ~15 minutes to afford a yellow solid. The solid was suspended in MeCN, sonicated, filtered and the solid washed with MeCN to afford 4-(tert-butyl)-1-(5-((2-chloropyridin-4-yl)oxy)-6-methylpyridin-2-yl)-1H-imidazol-2(3H)-one as a white solid (2.44 g, 31.8%). MS (ESI) m/z: 359.2 (M+H$^+$).

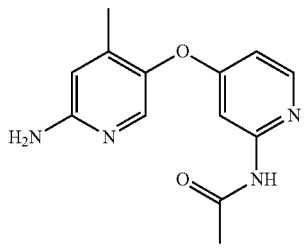 [SMILES: CC(=O)Nc1cc(Oc2cnc(N)cc2C)ccn1]

Example A13

A solution of 5-((2-chloropyridin-4-yl)oxy)-4-methyl-2-nitropyridine (0.52 g, 1.957 mmol; See: Example A9) in dioxane (15 mL) was sparged with Ar, treated with acetamide (0.347 g, 5.87 mmol), $Cs_2CO_3$ (0.638 g, 1.957 mmol), X-Phos (0.093 g, 0.196 mmol) and $Pd_2(dba)_3$ (0.179 g, 0.196 mmol) and heated at 90° C. overnight. The mixture was cooled to RT, diluted with EtOAc, the solids removed via filtration through diatomaceous earth, washed with EtOAc and the filtrate was washed with water, then brine, dried over $Na_2SO_4$, concentrated to dryness and purified via silica gel chromatography (EtOAc/DCM) to afford N-(4-((4-methyl-6-nitropyridin-3-yl)oxy)pyridin-2-yl)acetamide (360 mg, 64%). $^1$H NMR (400 MHz, DMSO-$d_6$): δ 10.66 (s, 1H), 8.47 (s, 1H), 8.43 (s, 1H), 8.24 (d, J=5.7 Hz, 1H), 7.72 (d, J=2.4 Hz, 1H), 6.74 (dd, J=5.7, 2.4 Hz, 1H), 2.33 (s, 3H), 2.05 (s, 3H); MS (ESI) m/z: 289.1 (M+H$^+$).

A solution of N-(4-((4-methyl-6-nitropyridin-3-yl)oxy)pyridin-2-yl)acetamide (0.36 g, 1.249 mmol) in EtOAc (15 mL) was treated with 10% Pd/C (50% w/w water, 0.133 g, 0.125 mmol) and hydrogenated (1 atm) overnight. The solids were removed via filtration through diatomaceous earth, washed with EtOAc and the filtrate was concentrated to dryness to afford N-(4-((6-amino-4-methylpyridin-3-yl)oxy)pyridin-2-yl)acetamide (320 mg, 99%). $^1$H NMR (400 MHz, DMSO-$d_6$): δ 10.47 (s, 1H), 8.11 (d, J=5.7 Hz, 1H), 7.66 (s, 1H), 7.55 (d, J=2.4 Hz, 1H), 6.55 (dd, J=5.7, 2.4 Hz, 1H), 6.37 (s, 1H), 5.88 (s, 2H), 2.02 (s, 3H), 1.93 (s, 3H); MS (ESI) m/z: 259.1 (M+H$^+$).

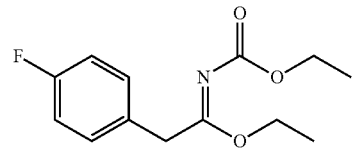 [SMILES: CCOC(=O)/N=C(/Cc1ccc(F)cc1)OCC]

Example B1

2-(4-Fluorophenyl)acetonitrile (1.0 g, 7.4 mmol) was dissolved in anhydrous ethanol (2 mL) under an atmosphere of Ar. The solution was cooled to 0° C., saturated with HCl gas, stirred for 6 h, allowed to warm to RT, and stirred for 6 h. Organic solvent was removed in vacuo to afford ethyl 2-(4-fluorophenyl)acetimidate hydrochloride (1.6 g, 100%) as a white solid. $^1$H NMR (400 MHz, DMSO-$d_6$): δ 12.27 (m, 1H), 11.20 (m, 1H), 7.40 (dd, J=8.3, 5.5 Hz, 2H), 7.19 (t, J=8.8 Hz, 2H), 4.38 (q, J=7.0 Hz, 2H), 3.99 (s, 2H), 1.25 (t, J=7.0 Hz, 3H).

Ethyl 2-(4-fluorophenyl)acetimidate hydrochloride (1.6 g, 7.4 mmol) was suspended in hexanes (18.5 mL) and DCM (18.5 mL) at 0° C. 2,4,6-collidine (3.9 mL, 29.6 mmol) and ethyl chloroformate (1.6 g, 14.8 mmol) were added sequentially and the reaction mixture was allowed to warm to RT and stirred for 12 h. The solvent was removed in vacuo and the residue was suspended in EtOAc (100 mL) and sonicated for 10 minutes. The solids were removed by filtration through a pad of diatomaceous earth and the filter cake was washed with EtOAc (3×10 mL). The combined filtrates were concentrated in vacuo to afford ethyl N-ethoxycarbonyl-2-(4-fluorophenyl)acetimidate (0.99 g, 52.7%) as an amorphous yellow solid. $^1$H NMR (400 MHz, DMSO-$d_6$): δ 7.25 (dd, J=8.5, 5.6 Hz, 2H), 7.13 (t, J=8.8 Hz, 2H), 4.06 (q, J=7.1 Hz, 2H), 4.04 (q, J=7.1 Hz, 2H), 3.66 (s, 2H), 1.15 (t, J=7.1 Hz, 3H), 1.14 (t, J=7.1 Hz, 3H).

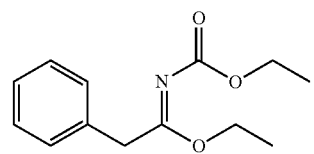 [SMILES: CCOC(=O)/N=C(/Cc1ccccc1)OCC]

Example B2

2-Phenylacetonitrile was dissolved in anhydrous ethanol (2 mL) under an atmosphere of Ar. The solution was cooled to 0° C., saturated with HCl gas, stirred for 6 h, allowed to warm to RT, and stirred for 6 h. The solvent was removed in vacuo to afford ethyl 2-phenylacetimidate hydrochloride (1.7 g, 99%) as a white solid. $^1$H NMR (400 MHz, DMSO-$d_6$): δ 7.36-7.35 (m, 5H), 4.39 (q, J=7.0 Hz, 2H), 3.99 (s, 2H), 1.26 (t, J=7.0 Hz, 3H).

Ethyl 2-phenylacetimidate hydrochloride (1.7 g, 8.5 mmol) was dissolved in DCM (10.6 mL) and cooled to 0° C.

TEA (7.1 mL, 51.1 mmol) was added dropwise the mixture was stirred for 1 h. Ethyl chloroformate (1.6 g, 14.8 mmol) was added and the reaction mixture was allowed to warm to RT and stirred for 12 h. The mixture was diluted with EtOAc (100 mL) and the solids were removed by filtration through diatomaceous earth. The filter cake was washed with EtOAc (3×10 mL) and the combined filtrates were concentrated in vacuo to afford ethyl N-ethoxycarbonyl-2-phenylacetimidate (1.9 g, 93%) as a yellow oil. ¹H NMR (400 MHz, DMSO-d₆): δ 7.27-7.26 (m, 5H), 4.01-4.00 (m, 4H), 3.70 (s, 2H), 1.18-1.08 (m, 6H).

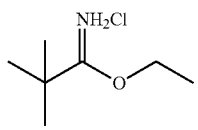

Example B3

Pivalonitrile (1.3 mL, 12.0 mmol) was dissolved in anhydrous ethanol (28 mL) under an atmosphere of Ar. The solution was cooled to 0° C., saturated with HCl gas, stirred for 6 h, allowed to warm to RT, and stirred for 54 h. The solvent was removed in vacuo to afford ethyl pivalimidate hydrochloride (2.0 g, 100%) as an off white solid. ¹H NMR (400 MHz, DMSO-d₆): δ 11.19 (br s, 1H), 4.42 (q, J=6.9 Hz, 2H), 1.33 (t, J=6.8 Hz, 3H), 1.24 (s, 9H).

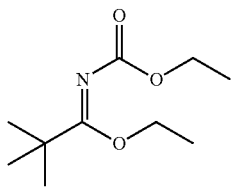

Example B4

Ethyl pivalimidate hydrochloride (Example B3) (0.75 g, 4.5 mmol) was suspended in hexanes (11.3 mL) and DCM (11.3 mL) and cooled to 0° C. 2,4,6-Collidine (2.1 mL, 15.9 mmol) and ethyl chloroformate (0.98 g, 9.1 mmol) were sequentially added and the reaction mixture was allowed to warm to RT and stirred for 12 h. The solvent was removed in vacuo and the residue was slurried with EtOAc (50 mL). The solids were removed by filtration through a pad of diatomaceous earth. The filter cake was washed with EtOAc (3×10 mL) and the combined filtrates were concentrated in vacuo to afford ethyl N-ethoxycarbonylpivalimidate (0.81 g, 89%) as a yellow solid. ¹H NMR (400 MHz, DMSO-d₆): δ 4.05 (q, J=7.1 Hz, 2H), 3.95 (q, J=7.0 Hz, 2H), 1.18 (t, J=7.1 Hz, 3H), 1.18 (t, 7.1 Hz, 3H), 1.15 (s, 9H).

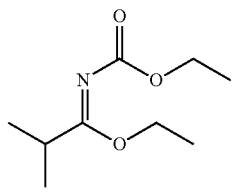

Example B5

Isobutyronitrile (1 g, 14.5 mmol) was dissolved in anhydrous ethanol (30 mL) under an atmosphere of Ar. The solution was cooled to 0° C., saturated with HCl gas, stirred for 6 h, allowed to warm to RT, and stirred for 6 h. The solvent was removed in vacuo to afford ethyl isobutyrimidate hydrochloride (1.8 g, 82%) as a colorless solid. ¹H NMR (400 MHz, DMSO-d₆): δ 11.78 (br s, 1H), 11.05 (br s, 1H), 4.40 (q, J=7.0 Hz, 2H), 2.93-2.92 (m, 1H), 1.33 (t, J=7.0 Hz, 3H), 1.16 (d, J=6.9 Hz, 6H).

Ethyl isobutyrimidate hydrochloride (1.8 g, 11.9 mmol) was suspended in hexanes (29.7 mL) and cooled to 0° C. 2,4,6-Collidine (4.1 mL, 30.9 mmol) and ethyl chloroformate (1.9 g, 17.8 mmol) were sequentially added and the mixture was allowed to warm to RT and stirred for 12 h. Organic solvent was removed in vacuo. The residue was suspended in EtOAc (50 mL) and solids were removed by filtration through a pad of diatomaceous earth. The filter cake was washed with EtOAc (3×10 mL) and the combined filtrates were concentrated in vacuo to afford ethyl N-ethoxycarbonylisobutyrimidate (2.2 g, 99%) as a yellow amorphous solid. ¹H NMR (400 MHz, DMSO-d₆): δ 4.09 (q, J=7.1 Hz, 2H), 4.03 (q, J=7.1 Hz, 2H), 2.65-2.64 (m, 1H), 1.20 (t, J=7.1 Hz, 3H), 1.19 (t, J=7.1 Hz, 3H), 1.07 (d, J=6.8 Hz, 6H).

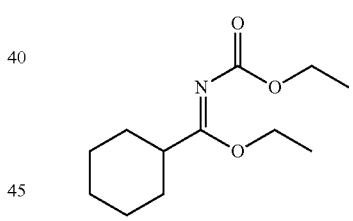

Example B6

Cyclohexanecarbonitrile (1.0 g, 9.2 mmol) was dissolved in anhydrous ethanol under an atmosphere of Ar. The solution was cooled to 0° C., saturated with HCl gas, stirred for 6 h, allowed to warm to RT, and stirred for 6 h. The solvent was removed in vacuo to afford ethyl cyclohexanecarbimidate hydrochloride (1.8 g, 100%) as a colorless solid. ¹H NMR (400 MHz, DMSO-d₆): δ 11.66 (m, 1H), 11.03 (m, 1H), 4.39 (q, J=7.0 Hz, 2H), 2.62 (m, 1H), 1.84 (d, J=12.6 Hz, 2H), 1.70-1.65 (m, 3H), 1.40-1.38 (m, 2H), 1.33 (t, J=7.0 Hz, 3H), 1.23-1.19 (m, 3H).

Ethyl cyclohexanecarbimidate hydrochloride (1.8 g, 9.2 mmol) was suspended in hexanes (22.9 mL) and cooled to 0° C. 2,4,6-Collidine (4.1 mL, 30.9 mmol) and ethyl chloroformate (1.9 g, 17.8 mmol) were sequentially added and the mixture was allowed to warm to RT and stirred for 12 h. The solvent was removed in vacuo. The residue was suspended in EtOAc (50 mL) and the solids were removed by filtration through diatomaceous earth. The filter cake was washed with EtOAc (3×10 mL) and the combined filtrates were concentrated in vacuo to afford ethyl N-ethoxycarbonylcyclohexanecarbimidate (2.0 g, 96%) as a yellow amorphous solid. $^1$H NMR (400 MHz, DMSO-$d_6$): δ 4.09 (q, J=7.1 Hz, 2H), 4.02 (q, J=7.1 Hz, 2H), 2.41-2.31 (m, 1H), 1.70-1.65 (m, 4H), 1.40-1.36 (m, 2H), 1.26-1.09 (m, 4H), 1.19 (t, J=7.1 Hz, 6H).

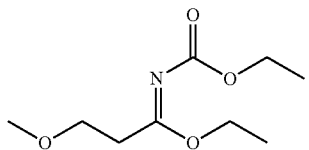

Example B7

3-Methoxypropanenitrile (5.0 g, 58.8 mmol) was dissolved in anhydrous ethanol (50 mL) under an atmosphere of Ar. The solution was cooled to 0° C., saturated with HCl gas, stirred for 6 h, allowed to warm to RT, and stirred for 6 h. The solvent was removed in vacuo. The residue was slurried with hexanes (50 mL) and sonicated for 10 min. The solids were allowed to settle and the solvent was removed by decantation. This was repeated (3×). The solid was collected and dried under high vacuum for 5 h to afford ethyl 3-methoxypropanimidate hydrochloride (6.2 g, 63%) as a white solid. $^1$H NMR (400 MHz, DMSO-$d_6$): δ 12.03 (br s, 1H), 11.22 (br s, 1H), 4.42 (q, J=7.0 Hz, 2H), 3.60 (t, J=5.9 Hz, 2H), 3.23 (s, 3H), 2.87 (t, J=5.9 Hz, 2H), 1.33 (t, J=7.0 Hz, 3H).

Ethyl 3-methoxypropanimidate hydrochloride (1.0 g, 6.0 mmol) was suspended in DCM (12 mL) and cooled to 0° C. Pyridine (2 mL, 24.7 mmol) was added dropwise and the mixture was stirred for 15 min. Ethyl chloroformate (0.97 g, 9.0 mmol) was added dropwise and the mixture was diluted with DCM (20 mL), allowed to warm to RT, and stirred for 12 h. The mixture was diluted with a mixture of EtOAc and hexanes (1:1, 200 mL) and the solids were removed by filtration through a pad of diatomaceous earth. The filtrate was concentrated in vacuo to afford ethyl N-ethoxycarbonyl-3-methoxy-propanimidate (1.0 g, 83%) as a light green solid. $^1$H NMR (400 MHz, DMSO-$d_6$): δ 4.08 (q, J=7.0 Hz, 2H), 4.05 (q, J=7.0 Hz, 2H), 3.50 (t, J=6.4 Hz, 2H), 3.19 (s, 3H), 2.57 (t, J=6.4 Hz, 2H), 1.20 (t, J=7.0 Hz, 3H), 1.19 (t, J=7.0 Hz, 3H).

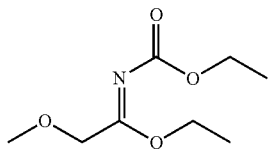

Example B8

2-Methoxyacetonitrile (1.0 g, 14.1 mmol) was dissolved in anhydrous ethanol (28.1 mL) under an atmosphere of Ar. The solution was cooled to 0° C., saturated with HCl gas, stirred for 6 h, allowed to warm to RT, and stirred for 6 h. The solvent was removed in vacuo to afford ethyl 2-methoxyacetimidate hydrochloride (1.0 g, 44.0%) as a white solid. $^1$H NMR (400 MHz, DMSO-$d_6$): δ 4.42 (q, J=7.0 Hz, 2H), 4.31 (s, 2H), 3.36 (s, 3H), 1.32 (t, J=7.0 Hz, 3H).

Ethyl 2-methoxyacetimidate hydrochloride (0.95 g, 6.18 mmol) was suspended in DCM (12.4 mL) and the mixture was cooled to 0° C. Pyridine (2.5 mL, 30.9 mmol) and ethyl chloroformate (1.2 mL, 12.4 mmol) were added sequentially and the solution was allowed to warm to RT and stirred for 12 h. EtOAc (100 mL) was added and solids were removed by filtration through a pad of diatomaceous earth. The filtrate was concentrated in vacuo to afford ethyl N-ethoxycarbonyl-2-methoxyacetimidate (1.2 g, 100%) as a white solid. $^1$H NMR (400 MHz, DMSO-$d_6$): δ 4.08-4.03 (m, 2H), 3.90 (q, J=7.0 Hz, 4H), 3.20 (s, 3H), 1.11 (t, J=6.9 Hz, 6H).

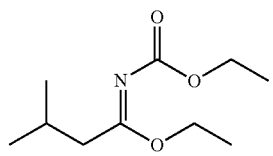

Example B9

Isovaleronitrile (2.0 g, 24.1 mmol) was dissolved in anhydrous ethanol (48 mL) under an atmosphere of Ar. The solution was cooled to 0° C., saturated with HCl gas, stirred for 6 h, allowed to warm to RT, and stirred for 6 h. The solvent was removed in vacuo to afford ethyl 3-methylbutanimidate hydrochloride (4.0 g, 100%) as a white solid. $^1$H NMR (400 MHz, DMSO-$d_6$): δ 12.00 (br s, 1H), 11.09 (br s, 1H), 4.42 (q, J=7.0 Hz, 2H), 2.48-2.47 (m, 2H), 2.02-2.01 (m, 1H), 1.33 (t, J=7.0 Hz, 3H), 0.91 (d, J=6.7 Hz, 6H).

Ethyl 3-methylbutanimidate hydrochloride (4.0 g, 24.2 mmol) was suspended in DCM (48 mL) and the mixture was cooled to 0° C. Pyridine (10.0 mL, 124 mmol) was added and the mixture was stirred for 15 minutes. Ethyl chloroformate (5.3 mL, 48.3 mmol) was added and the solution was allowed to warm to RT and stirred for 12 h. The mixture was diluted with a mixture of EtOAc and hexanes (1:1, 200 mL) and solids were removed by filtration through a diatomaceous earth. The filtrate was concentrated in vacuo to afford ethyl N-ethoxycarbonyl-3-methyl-butanimidate (4.3 g, 88%) as a colorless viscous oil. $^1$H NMR (400 MHz, DMSO-$d_6$): δ 4.09 (q, J=7.1 Hz, 2H), 4.05 (q, J=7.1 Hz, 2H), 2.18 (d, J=7.4 Hz, 2H), 1.95-1.94 (m, 1H), 1.20 (t, J=7.1 Hz, 3H), 1.19 (t, J=7.1 Hz, 3H), 0.86 (d, J=6.7 Hz, 6H).

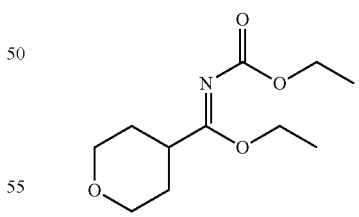

Example B10

Tetrahydro-2H-pyran-4-carbonitrile (1 g, 9.00 mmol) was dissolved in dry ethanol (10 mL) and cooled to 0° C. HCl (gas) was bubbled through the solution for five minutes. The reaction mixture was allowed to warm to RT and stir for 2 days. The solvent was removed under reduced pressure and the resulting solid was dried under high vacuum to yield ethyl tetrahydro-2H-pyran-4-carbimidate hydrochloride (1.646 g, 94%). $^1$H NMR (400 MHz, DMSO-d$_6$): δ 11.54 (br s, 1H), 7.35 (s, 1H), 4.41 (q, J=7.0 Hz, 2H), 3.88-3.86 (m, 2H), 3.33-3.27 (m, 2H), 2.98 (tt, J=11.7, 3.9 Hz, 1H), 1.77 (dd, J=13.1, 3.4 Hz, 2H), 1.65-1.63 (m, 2H), 1.34 (t, J=7.0 Hz, 3H).

Ethyl tetrahydro-2H-pyran-4-carbimidate hydrochloride (1.646 g, 8.50 mmol) was suspended in DCM (21.25 mL) and cooled to 0° C. Pyridine (3.09 mL, 38.2 mmol) was added and the solution was stirred for 15 min. Ethyl chloroformate (1.384 g, 12.75 mmol) was added dropwise. The reaction mixture was allowed to warm to RT and stir overnight. The reaction mixture was diluted with 50% hexane/EtOAc and the resulting suspension was filtered through a plug of diatomaceous earth. The filtrate was concentrated under reduced pressure and the residue dried under high vacuum for several hours to yield ethyl N-ethoxycarbonyltetrahydro-2H-pyran-4-carbimidate (1.80 g, 92%). $^1$H NMR (400 MHz, DMSO-d$_6$): δ 4.12 (m, 2H), 4.07 (m, 2H), 3.85-3.83 (m, 2H), 3.31-3.24 (m, 2H), 2.69-2.68 (m, 1H), 1.69-1.68 (m, 4H), 1.23 (m, 6H).

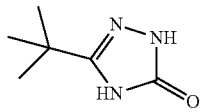

Example C1

Semicarbazide hydrochloride (25.0 g, 224 mmol) was dissolved in water (200 mL). NaHCO$_3$ (40.0 g, 476 mmol) was slowly added to the solution over 30 min at RT followed by the addition of trimethylacetyl chloride (30.0 g, 249 mmol). The mixture was stirred at RT for 12 h. Solids were collected by filtration, washed with cold water, and dried in vacuo. A solution of NaOH (20.0 g, 500 mmol) in water (200 mL) was added. The mixture was stirred at 100° C. for 2 h, cooled with an ice-bath, and neutralized by the drop-wise addition of concentrated HCl. The solids were collected by filtration, washed with water, and dried in vacuo to afford 3-(tert-butyl)-1H-1,2,4-triazol-5(4H)-one (19.6 g, 61.9%) as a white solid. $^1$H NMR (400 MHz, DMSO-d$_6$): δ 11.26 (s, 1H), 11.04 (s, 1H), 1.16 (s, 9H); MS (ESI) m/z: 142.1 (M+H$^+$).

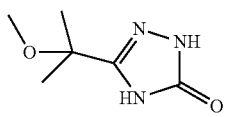

Example C2

2-Methoxyisobutyric acid (0.50 g, 4.23 mmol) was dissolved in MeCN (8.5 mL). 1H-Benzo[d][1,2,3]triazol-1-ol (20% hydrate) (0.65 g, 4.23 mmol) and N-(3-dimethylaminopropyl)-N'-ethylcarbodiimide hydrochloride (0.81 g, 4.23 mmol) were added and the mixture was stirred at RT for 2 h. Semicarbazide hydrochloride (0.47 g, 4.23 mmol) was added and the mixture was stirred for an additional 12 h. Organic solvent was removed in vacuo and the residue was suspended in water (85 mL). Potassium hydroxide (0.48 g, 8.5 mmol) was added and the mixture was stirred at RT until complete dissolution of solids. The mixture was then stirred at 100° C. for 12 h and then allowed to cool to RT. The solution was saturated with solid NH$_4$Cl and extracted with EtOAc (8×50 mL). The combined organics were dried (Na$_2$SO$_4$) and concentrated in vacuo to afford 3-(2-methoxypropan-2-yl)-1H-1,2,4-triazol-5(4H)-one (0.35 g, 52.6%) as an amorphous solid. $^1$H NMR (400 MHz, DMSO-d$_6$): δ 11.44 (s, 1H), 11.28 (s, 1H), 2.96 (s, 3H), 1.36 (s, 6H).

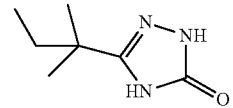

Example C3

2,2-Dimethylbutyric acid (1 g, 8.6 mmol) was dissolved in DCM (10 mL) and cooled to 0° C. The solution was treated with oxalyl chloride (1.2 mL, 13.8 mmol) and DMF (0.07 mL, 0.87 mmol), allowed to warm to RT, and stirred for 2 h for complete conversion to 2,2-dimethylbutyric acid chloride. The solution was cooled to 0° C. and added to a stirred solution of semicarbazide hydrochloride (1.4 g, 12.9 mmol) and NaOH (1.4 g, 34.4 mmol) in a mixture of dioxane (10 mL) and water (2.0 mL) at 0° C. The reaction mixture was allowed to warm to RT and stirred for 12 h. Organic solvent was evaporated in vacuo, and the resultant slurry was diluted with 2 M NaOH (aq) (50 mL, 100 mmol). The suspension was stirred at 100° C. for 24 h. The aqueous solution was saturated with solid NH$_4$Cl and extracted with EtOAc (5×50 mL). The combined organics were dried (Na$_2$SO$_4$) and concentrated in vacuo to afford 3-(tert-pentyl)-1H-1,2,4-triazol-5(4H)-one (0.71 g, 53.1%) as a white solid. $^1$H NMR (400 MHz, DMSO-d$_6$): δ 11.17 (s, 1H), 11.02 (s, 1H), 1.49 (q, J=7.5 Hz, 2H), 1.11 (s, 6H), 0.68 (t, J=7.4 Hz, 3H); MS (ESI) m/z: 156.1 (M+H$^+$).

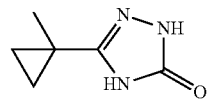

Example C4

2-Methylcyclopropanecarboxylic acid (0.86 g, 8.6 mmol) was dissolved in DCM (10 mL) and cooled to 0° C. The solution was treated with oxalyl chloride (1.2 mL, 13.8 mmol) and DMF (0.07 mL, 0.87 mmol), allowed to warm to RT, and stirred for 2 h for complete conversion to 2-methylcyclopropanecarboxylic acid chloride. The solution was cooled to 0° C. and added via syringe to a stirred solution of semicarbazide hydrochloride (1.4 g, 12.9 mmol) and NaOH (1.4 g, 34.4 mmol) in a mixture of dioxane (10 mL) and water (2.0 mL) at 0° C. The reaction mixture was allowed to warm to RT and stirred for 12 h. The organic solvent was evaporated in vacuo, and the resultant slurry was diluted with 2 M NaOH (aq) (50 mL, 100 mmol). The suspension was stirred at 100° C. for 24 h. The aqueous solution was saturated with solid NH$_4$Cl and extracted with EtOAc (5×50 mL). The combined organics were dried (Na$_2$SO$_4$) and concentrated in vacuo to afford 3-(1-methylcyclopropyl)-1H-1,2,4-triazol-5(4H)-one (0.65 g, 54.3%) as a white solid. $^1$H NMR (400 MHz, DMSO-d$_6$): δ 11.02 (m, 2H), 1.26 (s, 3H), 0.90-0.89 (m, 2H), 0.66-0.65 (m, 2H); MS (ESI) m/z: 140.1 (M+H$^+$).

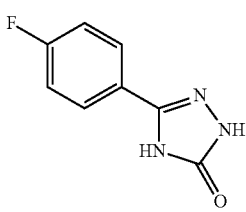 [SMILES: O=c1[nH]nc(-c2ccc(F)cc2)[nH]1]

Example C5

4-Fluorobenzoyl chloride (2.50 g, 15.77 mmol) was added to a solution of semicarbazide hydrochloride (2.00 g, 17.93 mmol) and sodium bicarbonate (2.50 g, 29.8 mmol) in water (25 mL) and the mixture was stirred at RT for 2 h. The solids were collected by filtration, and washed and dried under suction to obtain a white solid. MS (ESI) m/z: 198.1 (M+H$^+$). The solid was suspended in water (25 mL), treated with sodium hydroxide (1.50 g, 37.5 mmol) and heated at 100° C. for 5 hours. The reaction mixture was cooled in ice bath, acidified with conc. HCl and stirred for 20 min. The solids were collected by filtration. The white solid was stirred in acetonitrile filtered, washed and dried to provide 3-(4-fluorophenyl)-1H-1,2,4-triazol-5(4H)-one (1.1 g, 38.9% yield) as white solid. $^1$H NMR (400 MHz, DMSO-d$_6$): δ 12.03 (s, 1H), 11.65 (s, 1H), 7.81 (m, 2H), 7.31 (m, 2H); MS (ESI) m/z: 180.1 (M+H$^+$).

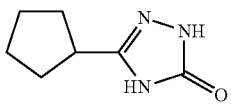 [SMILES: O=c1[nH]nc(C2CCCC2)[nH]1]

Example C6

To a suspension of semicarbazide hydrochloride (5.00 g, 44.8 mmol) in DCM (100 mL) was added triethylamine (10.00 g, 99 mmol) and the mixture was stirred at –10° C. for 30 min. Cyclopentane carbonylchloride (5.00 g, 37.7 mmol) was added at the same temp and the mixture was allowed to warm to RT over night. The solvent from the reaction mixture was completely removed and the residue stirred in MeCN (200 mL) for 1 h. The solids were collected by filtration, washed and dried. The solid was treated with sodium hydroxide (7.00 g, 175 mmol) and water (20 mL). The resulting reaction mixture was heated at 100° C. for 3 h. The reaction mixture was cooled and acidified with conc. HCl. The solids were collected, washed and dried to provide 3-cyclopentyl-1H-1,2,4-triazol-5(4H)-one (2.24 g, 38.8% yield) as white solid. $^1$H NMR (400 MHz, DMSO-d$_6$): δ 11.17 (s, 1H), 11.03 (s, 1H), 2.80 (m, 1H), 1.86 (m, 2H), 1.58 (m, 6H); MS (ESI) m/z: 154.1 (M+H$^+$).

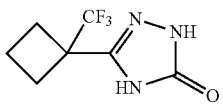 [SMILES: O=c1[nH]nc(C2(C(F)(F)F)CCC2)[nH]1]

Example C7

To a 0° C. solution of 1-trifluoromethyl-1-cyclobutylcarboxylic acid (1.50 g, 8.92 mmol) in DCM (15 mL) was added oxalyl chloride (1.50 g, 11.82 mmol) followed by catalytic amount of DMF. The reaction mixture was stirred at RT for 1 h. The solvent from the reaction mixture was completely evaporated. In a different flask, a suspension of semicarbazide hydrochloride (1.50 g, 13.45 mmol) in water (15 mL) was treated with NaHCO$_3$ (1.50 g, 17.86 mmol) and stirred at RT for 30 minutes till a clear solution forms. To this solution was added the above acid chloride dissolved in EtOAc (20 mL) and the resultant mixture was stirred at RT over night. The organic layer was separated and the aqueous layer was extracted with DCM (2×10 mL). The combined organics were concentrated and the residue was treated with sodium hydroxide (1.50 g, 37.5 mmol) in water (15 mL), heated at 100° C. for 3 h, and stirred for 20 h at RT. The reaction mixture was acidified with conc. HCl to pH 1 and stirred at RT for 1 h. The reaction mixture was concentrated to a small volume under high vacuum and diluted with MeOH. The separated solids were filtered and washed with methanol. The filtrate was evaporated and further dried by azeotropic distillation from toluene to provide 5-(1-(trifluoromethyl)cyclobutyl)-2,4-dihydro-3H-1,2,4-triazol-3-one (1.05 g, 57%) as a light brownish residue, suitable for use without further purification. MS (ESI) m/z: 208.1 (M+H$^+$).

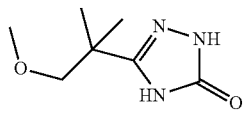

Example C8

3-Hydroxy-2,2-dimethylpropanoic acid (15.00 g, 127.0 mmol) was dissolved in a solution of MeOH (200 mL) and conc. H$_2$SO$_4$ (13.5 g, 254 mmol) and stirred at reflux for 16 h. The reaction mixture was concentrated in vacuo, diluted with EtOAc (100 mL), washed with water (2×50 mL), sat. NaHCO$_3$ (aq) (50 mL), water (50 mL), brine (1×50 mL), and dried (Na$_2$SO$_4$). Organic solvent was removed in vacuo to afford methyl 3-hydroxy-2,2-dimethylpropanoate (6.4 g, 57.2%) as a colorless liquid. $^1$H NMR (400 MHz, DMSO-d$_6$): δ 3.71 (s, 3H), 3.56 (s, 2H), 2.05-2.04 (m, 1H), 1.19 (s, 6H).

Sodium hydride (1.16 g, 48.4 mmol) was dissolved in THF (48 mL) and cooled to 0° C. 3-Hydroxy-2,2-dimethylpropanoate (6.4 g, 48.4 mmol) was added dropwise and the mixture was stirred at 0° C. for 30 min, allowed to warm to RT, and stirred an additional 1 h. The mixture was cooled back to 0° C. and iodomethane (3.0 mL), 48.4 mmol) was added. The reaction mixture was allowed to warm to RT and stirred for 16 h. The reaction mixture was filtered through a pad of diatomaceous earth and the filter cake was washed with THF (2×35 mL). The filtrates were combined and diluted with water (150 mL). Lithium hydroxide hydrate (8.13 g, 194 mmol) was added and the reaction mixture was stirred at RT for 16 h. The aqueous phase was collected and the organic phase was extracted with 0.5 N NaOH (aq) (3×50 mL). The combined aqueous phases were washed with Et$_2$O (20 mL) and hexanes (2×100 mL), saturated with solid NaCl, and the pH of the solution was adjusted to ~2 by the careful addition of conc. HCl (aq). The acidic solution was extracted with EtOAc (4×100 mL) and the combined organics were dried (Na$_2$SO$_4$) and concentrated in vacuo to afford 3-methoxy-2,2-dimethylpropanoic acid (5.8 g, 91%) as a red oil. $^1$H NMR (400 MHz, DMSO-d$_6$): δ 12.02 (s, 1H), 3.29 (s, 2H), 3.23 (s, 3H), 1.06 (s, 6H).

3-Methoxy-2,2-dimethylpropanoic acid (3.00 g, 22.7 mmol) was dissolved in DCM (21 mL) at RT. Oxalyl chloride (2.4 mL, 27.2 mmol) and DMF (0.2 mL, 2.6 mmol) were added and the reaction mixture was stirred at RT for 2 h. In a separate flask, semicarbozide hydrochloride (3.0 g, 27.2 mmol) and NaOH (3.0 g, 75.0 mmol) were dissolved in a solution of dioxane (4.2 mL) and water (21.0 mL). The solution of acid chloride was added in one portion to the latter solution and the reaction mixture was stirred at RT for 12 h. 2 M NaOH (aq) (45.4 mL, 91 mmol) was added and the reaction mixture was stirred at 100° C. for 4 h and allowed to cool to RT. The pH of the solution was adjusted to ~3 by the careful addition of conc. HCl (aq) and subsequently extracted with EtOAc (2×50 mL). The combined organics were dried (Na$_2$SO$_4$) and concentrated in vacuo to afford 3-(1-methoxy-2-methylpropan-2-yl)-1H-1,2,4-triazol-5(4H)-one (0.8 g, 20.6%) as a white solid. $^1$H NMR (400 MHz, DMSO-d$_6$): δ 11.19 (s, 1H), 11.08 (s, 1H), 3.29 (s, 2H), 3.20 (s, 3H), 1.12 (s, 6H).

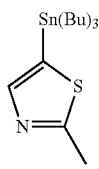

Example D1

A −78° C. solution of 2-methylthiazole (2 g, 20.17 mmol) in THF (50 mL) was treated drop-wise with n-butyllithium (2.5 M in Hex, 10.49 mL, 26.2 mmol), stirred for 1 h, treated drop-wise with a solution of tributyltin chloride (7.11 mL, 26.2 mmol) in THF (25 mL) and stirred for an additional 1 h at −78° C. The mixture was allowed to warm to RT, stirred for 1 h, treated slowly with ice-cold satd. NaHCO$_3$ (20 mL) and quickly extracted with Et$_2$O (3×). The combined organics were washed with brine, dried over Na$_2$SO$_4$, concentrated to dryness and purified via silica gel chromatography (EtOAc/Hex) to afford 2-methyl-5-(tributylstannyl)thiazole (6.67 g, 85%). $^1$H NMR (400 MHz, DMSO-d$_6$): δ 7.55 (s, 1H), 2.67 (s, 3H), 1.54-1.45 (m, 6H), 1.30-1.23 (m, 6H), 1.09-1.04 (m, 6H), 0.83 (t, J=7.3 Hz, 9H).

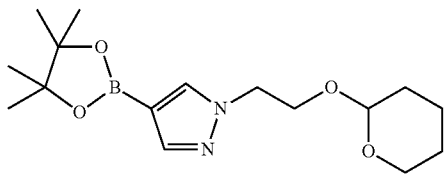 [SMILES: CC1(C)OB(c2cnn(CCOC3CCCCO3)c2)OC1(C)C]

Example D2

A solution of 4-iodopyrazole (20 g, 0.10 mol) in anhydrous DMF (300 mL) was treated with Cs$_2$CO$_3$ (32.5 g, 0.10 mol) and 2-(2-bromoethoxy)tetrahydro-2H pyran. The resultant reaction mixture was stirred at 70° C. overnight. The cooled mixture was diluted with EtOAc (500 mL) and water (500 mL). The layers were separated and the aqueous layer was extracted with EtOAc (3×500 mL). The combined organic layers were washed with water, dried over Na$_2$SO$_4$, and concentrated to afford yellow oil. Purification on a silica gel provided 4-iodo-1-[2-(tetrahydro-pyran-2-yloxy)-ethyl]-1H-pyrazole (22 g, 66.2% yield). $^1$H-NMR (300 MHz, CDCl$_3$): δ 7.55 (s, 1H), 7.50 (s, 1H), 4.53 (s, 1H), 4.33 (m, 2H), 4.03 (m, 1H), 3.74 (m, 1H), 3.61 (m, 1H), 3.46 (m, 1H), 1.60-1.48 (m, 6H).

A solution of iPrMgCl (2M in THF, 68.3 mL, 136.6 mmol) was added drop wise to a solution of 4-iodo-1-[2-(tetrahydro-pyran-2-yloxy)-ethyl]-1H-pyrazole (22 g, 68.3 mmol) in anhydrous THF (200 mL) 0° C. The reaction was stirred for 1 hour at 0° C. under nitrogen. 2-Methoxy-4,4,5,5-tetramethyl-1,3,2-dioxaborolane (16.1 g, 0.101 mol) was added and the resulting yellow solution was allowed to stir for 1 hour at ambient temperature under nitrogen. The reaction was quenched with sat. aqueous solution of NH$_4$Cl and was diluted with EtOAc. The organic layer was washed with brine, and dried over Na$_2$SO$_4$, concentrated under reduced pressure, and purified by silica gel chromatography to give 1-(2-((tetrahydro-2H-pyran-2-yl)oxy)ethyl)-4-(4,4,5,5-tetramethyl-1,3,2-dioxaborolan-2-yl)-1H-pyrazole as a oil. $^1$H-NMR (400 MHz, CDCl$_3$): δ 7.75 (m, 2H), 4.48 (s, 1H), 4.30 (m, 2H), 4.10 (m, 1H), 3.78-3.71 (m, 1H), 3.63-3.59 (m, 1H), 3.42-3.38 (m, 1H), 1.60-1.46 (m, 6H), 1.29 (s, 12H).

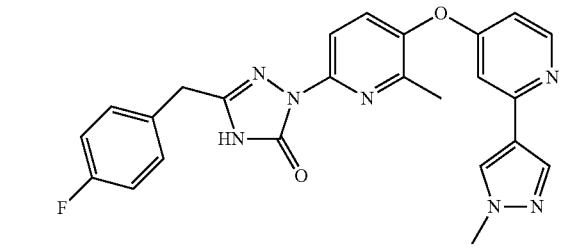 [SMILES: Cc1nc(-n2nc(Cc3ccc(F)cc3)[nH]c2=O)ccc1Oc1ccnc(-c2cnn(C)c2)c1]

Example 1

Example A4 (0.05 g, 0.17 mmol) and Example B1 (0.43 g, 1.7 mmol) were suspended in toluene (0.35 mL). The mixture was stirred at 45° C. for 30 min and allowed to cool to RT. TEA (0.05 mL, 0.4 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-(4-fluorobenzyl)-1-(6-methyl-5-((2-(1-methyl-1H-pyrazol-4-yl)pyridin-4-yl)oxy)pyridin-2-yl)-1H-1,2,4-triazol-5(4H)-one (0.02 g, 26%) as a light yellow solid. $^1$H NMR (400 MHz, DMSO-d$_6$): δ 12.02 (s, 1H), 8.39 (d, J=5.9 Hz, 1H), 8.31-8.28 (m, 1H), 8.01-7.98 (m, 1H), 7.89 (d, J=8.8 Hz, 1H), 7.70 (d, J=8.8 Hz, 1H), 7.36-7.35 (m, 2H), 7.23-7.22 (m, 4H), 3.89 (s, 2H), 3.84 (s, 3H), 2.32 (s, 3H); MS (ESI) m/z: 458.1 (M+H$^+$).

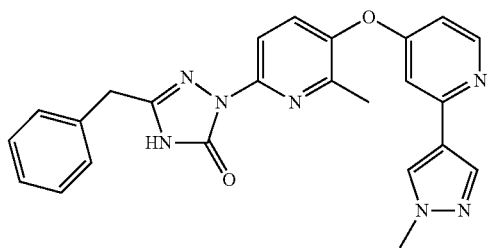 [SMILES: Cc1nc(-n2nc(Cc3ccccc3)[nH]c2=O)ccc1Oc1ccnc(-c2cnn(C)c2)c1]

Example 2

Example A4 (0.05 g, 0.17 mmol) and Example B2 (0.40 g, 1.7 mmol) were suspended in toluene (0.35 mL). The mixture was stirred at 45° C. for 30 min and allowed to cool to RT. TEA (0.05 mL, 0.4 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-benzyl-1-(6-methyl-5-((2-(1-methyl-1H-pyrazol-4-yl)pyridin-4-yl)oxy)pyridin-2-yl)-1H-1,2,4-triazol-5(4H)-one (0.025 g, 33.7%) as a light orange solid. $^1$H NMR (400 MHz, DMSO-d$_6$): δ 12.02 (s, 1H), 8.35 (d, J=5.7 Hz, 1H), 8.25 (s, 1H), 7.95 (s, 1H), 7.88 (d, J=8.8 Hz, 1H), 7.68 (d, J=8.8 Hz, 1H), 7.33-7.32 (m, 5H), 7.18 (d, J=2.4 Hz, 1H), 6.64 (dd, J=5.7, 2.4 Hz, 1H), 3.89 (s, 2H), 3.83 (s, 3H), 2.32 (s, 3H); MS (ESI) m/z: 440.2 (M+H$^+$).

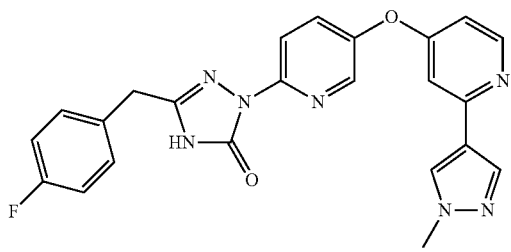 [SMILES: Cn1cc(-c2cc(Oc3ccc(-n4nc(Cc5ccc(F)cc5)[nH]c4=O)nc3)ccn2)cn1]

Example 3

Example A6 (0.2 g, 0.71 mmol) and Example B1 (1.8 g, 7.1 mmol) were suspended in toluene (1.4 mL). The mixture was stirred at 45° C. for 30 min and allowed to cool to RT. TEA (0.22 mL, 1.6 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-(4-fluorobenzyl)-1-(5-((2-(1-methyl-1H-pyrazol-4-yl)pyridin-4-yl)oxy)pyridin-2-yl)-1H-1,2,4-triazol-5(4H)-one (0.212 g, 66%) as an off white solid. $^1$H NMR (400 MHz, DMSO-d$_6$): δ 12.03 (s, 1H), 8.37-8.36 (m, 2H), 8.25 (s, 1H), 8.01 (d, J=9.0 Hz, 1H), 7.95 (s, 1H), 7.79 (dd, J=9.0, 2.9 Hz, 1H), 7.36 (dd, J=8.5, 5.6 Hz, 2H), 7.25 (d, J=2.4 Hz, 1H), 7.17 (t, J=8.9 Hz, 2H), 6.74 (dd, J=5.7, 2.4 Hz, 1H), 3.83 (s, 3H); MS (ESI) m/z: 444.2 (M+H$^+$).

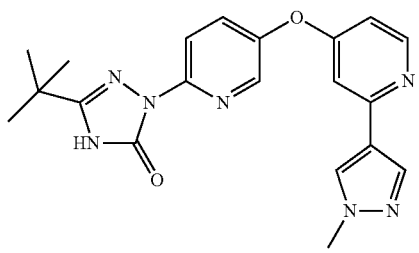 [SMILES: Cn1cc(-c2cc(Oc3ccc(-n4nc(C(C)(C)C)[nH]c4=O)nc3)ccn2)cn1]

Example 4

Example A6 (0.2 g, 0.71 mmol) and Example B4 (1.4 g, 7.1 mmol) were suspended in toluene (1.4 mL). The mixture was stirred at 45° C. for 30 min and allowed to cool to RT. TEA (0.22 mL, 1.6 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-(tert-butyl)-1-(5-((2-(1-methyl-1H-pyrazol-4-yl)pyridin-4-yl)oxy)pyridin-2-yl)-1H-1,2,4-triazol-5(4H)-one (0.026 g, 8.7%) as an off white solid. $^1$H NMR (400 MHz, DMSO-d$_6$): δ 11.99 (s, 1H), 8.39-8.38 (m, 2H), 8.25 (s, 1H), 8.04 (d, J=9.0 Hz, 1H), 7.96 (s, 1H), 7.79 (dd, J=9.0, 2.9 Hz, 1H), 7.24 (d, J=2.4 Hz, 1H), 6.74 (dd, J=5.7, 2.4 Hz, 1H), 3.83 (s, 3H), 1.26 (s, 9H); MS (ESI) m/z: 392.2 (M+H$^+$).

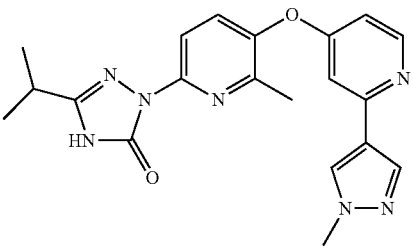 [SMILES: Cc1nc(-n2nc(C(C)C)[nH]c2=O)ccc1Oc1ccnc(-c2cnn(C)c2)c1]

Example 5

Example A4 (0.08 g, 0.27 mmol) and Example B5 (0.51 g, 2.7 mmol) were suspended in toluene (0.54 mL). The mixture was stirred at 45° C. for 30 min and allowed to cool to RT. TEA (0.08 mL, 0.6 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-isopropyl-1-(6-methyl-5-((2-(1-methyl-1H-pyrazol-4-yl)pyridin-4-yl)oxy)pyridin-2-yl)-1H-1,2,4-triazol-5(4H)-one (0.012 g, 10.3%) as a light orange solid. $^1$H NMR (400 MHz, DMSO-d$_6$): δ 11.92 (s, 1H), 8.37 (d, J=5.7 Hz, 1H), 8.26 (s, 1H), 7.96 (s, 1H), 7.87 (d, J=8.8 Hz, 1H), 7.69 (d, J=8.8 Hz, 1H), 7.19 (d, J=2.4 Hz, 1H), 6.64 (dd, J=5.7, 2.4 Hz, 1H), 3.84 (s, 3H), 2.84 (t, J=6.9 Hz, 1H), 2.33 (s, 3H), 1.23 (d, J=7.0 Hz, 6H); MS (ESI) m/z: 392.2 (M+H$^+$).

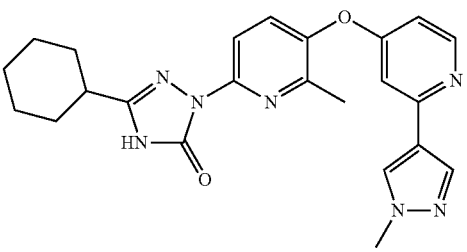 [SMILES: Cc1nc(-n2nc(C3CCCCC3)[nH]c2=O)ccc1Oc1ccnc(-c2cnn(C)c2)c1]

Example 6

Example A4 (0.08 g, 0.27 mmol) and Example B6 (0.61 g, 2.7 mmol) were suspended in toluene (0.54 mL). The mixture was stirred at 45° C. for 30 min and allowed to cool to RT. TEA (0.08 mL, 0.6 mmol) was added and the mixture was stirred at 100° C. for 12 h. The reaction was concentrated in vacuo and the residue was purified by silica gel chromatography (MeOH/DCM). The product was dissolved in MeCN and water, frozen to −78° C., and lyophilized to afford 3-cyclohexyl-1-(6-methyl-5-((2-(1-methyl-1H-pyrazol-4-yl)pyridin-4-yl)oxy)pyridin-2-yl)-1H-1,2,4-triazol-5(4H)-one (0.016 g, 12.4%) as a light orange solid. $^1$H NMR (400 MHz, DMSO-d$_6$): δ 11.88 (s, 1H), 8.36 (d, J=5.7 Hz, 1H), 8.26 (s, 1H), 7.96 (s, 1H), 7.87 (d, J=8.7 Hz, 1H), 7.68 (d, J=8.8 Hz, 1H), 7.19 (d, J=2.4 Hz, 1H), 6.64 (dd, J=5.7, 2.5 Hz, 1H), 3.84 (s, 3H), 2.65 (m, 1H), 2.32 (s, 3H), 1.93-1.19 (m, 10H); MS (ESI) m/z: 432.2 (M+H$^+$).

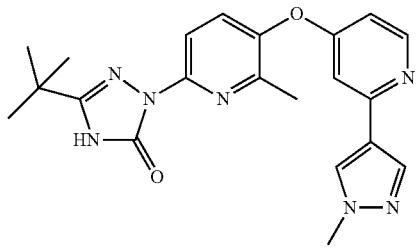 [SMILES: Cc1nc(-n2nc(C(C)(C)C)[nH]c2=O)ccc1Oc1ccnc(-c2cnn(C)c2)c1]

Example 7

Method 1: Example A4 (0.2 g, 0.68 mmol) and Example B3 (0.22 g, 1.4 mmol) were suspended in DCE (1 mL) and stirred at RT for 30 min. The mixture was diluted with DCM (4 mL) and cooled to 0° C. TEA (0.3 mL, 2.2 mmol) was added dropwise and the mixture was treated with a solution of bis(trichloromethyl)carbonate (0.1 g, 0.34 mmol) in DCM (1 mL), allowed to warm to RT, and stirred for 1 h. Sat. NaHCO$_3$ (aq) (5 mL) was added and the resultant suspension was extracted with DCM (4×5 mL). The combined organics were dried (Na$_2$SO$_4$), concentrated in vacuo, and the residue was purified by silica gel chromatography (MeOH/DCM). The isolated product was dissolved in MeCN and water, frozen to −78° C., and lyophilized to afford 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one (0.063 g, 22.3%). $^1$H NMR (400 MHz, acetone-d$_6$): δ 8.40 (d, J=5.7 Hz, 1H), 8.13 (s, 1H), 7.98-7.97 (m, 1H), 7.94 (s, 1H), 7.63 (d, J=8.7 Hz, 1H), 7.16 (d, J=2.4 Hz, 1H), 6.68 (dd, J=5.7, 2.4 Hz, 1H), 3.90 (s, 3H), 2.39 (s, 3H), 1.40 (s, 9H); MS (ESI) m/z: 406.2 (M+H$^+$).

Method 2: A suspension of Example A3 (3.00 g, 8.34 mmol), 1-methyl-4-(4,4,5,5-tetramethyl-1,3,2-dioxaborolan-2-yl)-1H-pyrazole (3.00 g, 14.42 mmol), K$_2$CO$_3$ (3.000 g, 21.71 mmol) in dioxane/water (10:1) (60 mL) was degassed for 5 minutes with argon purge. The reaction mixture was treated with Pd(PPh$_3$)$_4$ (0.300 g, 0.260 mmol) heated at 100° C. under argon over night. The residue was partitioned between dichloromethane (150 mL) and water (150 mL). Organic layer separated and the aqueous layer extracted with dichloromethane (2×70 mL). The combined organics were dried, concentrated in vacuo and purified by silica gel chromatography (0-100% THF/DCM). Pure fractions were combined and the solvent was evaporated. The residue was dissolved in THF, stirred with thiol-modified silica gel (1.4 mmol thiol/g, 3 g, 4.2 mmol) over night (to scavenge Pd). The reaction mixture was filtered and the filtrate completely evaporated. The residue was crystallized from acetonitrile to provide 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one (2.40 g, 70%) as white solid. $^1$H NMR (400 MHz, DMSO-d$_6$): δ 11.96 (s, 1H), 8.37 (d, J=5.7 Hz, 1H), 8.26 (s, 1H), 7.96 (s, 1H), 7.85 (d, J=8.8 Hz, 1H), 7.68 (d, J=8.8 Hz, 1H), 7.18 (d, J=2.4 Hz, 1H), 6.64 (dd, J=5.7, 2.4 Hz, 1H), 3.84 (s, 3H), 2.33 (s, 3H), 1.27 (s, 9H); MS (ESI) m/z: 406.2 (M+H$^+$).

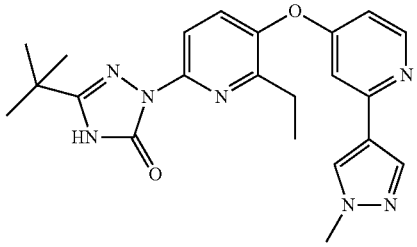

Example 8

2-Amino-6-ethylpyridine (3.0 g, 24.6 mmol) was dissolved in chloroform (25 mL) and cooled to 0° C. NBS (4.4 g, 24.6 mmol) was added portion-wise over 30 min and the mixture was stirred for 30 min at 0° C. The solvent was removed in vacuo and the residue was slurried with EtOAc (8 mL). The resultant solids were removed by filtration through a pad of diatomaceous earth and filtrate was concentrated in vacuo. The residue was purified by silica gel chromatography (EtOAc/hexanes) to afford 5-bromo-6-ethylpyridin-2-amine (3.83 g, 78%) as a white solid. $^1$H NMR (400 MHz, DMSO-d$_6$): δ 7.42 (d, J=8.6 Hz, 1H), 6.20 (d, J=8.7 Hz, 1H), 6.03 (s, 2H), 2.60 (q, J=7.5 Hz, 2H), 1.10 (t, J=7.5 Hz, 3H); MS (ESI) m/z: 201.0/203.0 (M+H$^+$).

A solution of concentrated H$_2$SO$_4$ (25 mL) was cooled to 0° C. Temperature was carefully maintained as 30% H$_2$O$_2$ (5.5 mL) was added over 30 min and 5-bromo-6-ethylpyridin-2-amine (3.77 g, 18.8 mmol) dissolved in concentrated H$_2$SO$_4$ (25 mL) was added dropwise. The mixture was allowed to slowly warm to RT, and stirred for an additional 4 h. at RT. The mixture was poured onto ice (~110 g), and the resultant emulsion was stirred as it was allowed to warm to RT. The emulsion was extracted with EtOAc (4×150 mL) and the combined organics were dried (Na$_2$SO$_4$) and concentrated in vacuo. The residue was purified by silica gel chromatography (EtOAc/hexanes) to afford 3-bromo-2-ethyl-6-nitropyridine (2.6 g, 60%) as a yellow oil. $^1$H NMR (400 MHz, DMSO-d$_6$): δ 8.44 (d, J=8.5 Hz, 1H), 8.05 (d, J=8.5 Hz, 1H), 2.97 (q, J=7.5 Hz, 2H), 1.24 (t, J=7.5 Hz, 3H); MS (ESI) m/z: 231.0/233.0 (M+H$^+$).

3-Bromo-2-ethyl-6-nitropyridine (2.6 g, 11.3 mmol) and 2-chloro-4-hydroxypyridine (2.9 g, 22.5 mmol) were dissolved in DMA (20 mL). The solution was sonicated and sparged with Ar for 10 min. K$_2$CO$_3$ (4.7 g, 33.8 mmol) was added and the reaction mixture was stirred at 110° C. for 12 h. EtOAc (80 mL) was added and the suspension was washed with 10% K$_2$CO$_3$ (aq) (2×50 mL), 5% LiCl (aq) (2×50 mL), and brine (2×50 mL). The solution was dried (Na$_2$SO$_4$), concentrated in vacuo, and the resultant residue was purified by silica gel chromatography (EtOAc/hexanes) to afford 3-((2-chloropyridin-4-yl)oxy)-2-ethyl-6-nitropyridine (1.3 g, 37.2%) as a yellow oil. $^1$H NMR (400 MHz, DMSO-d$_6$): δ 8.38 (d, J=5.7 Hz, 1H), 8.25 (d, J=8.7 Hz, 1H), 7.96 (d, J=8.7 Hz, 1H), 7.82 (d, J=8.6 Hz, 1H), 7.16 (dd, J=5.7, 2.3 Hz, 1H), 2.79 (q, J=7.5 Hz, 2H), 1.21 (t, J=7.5 Hz, 3H); MS (ESI) m/z: 280.0 (M+H$^+$).

3-((2-chloropyridin-4-yl)oxy)-2-ethyl-6-nitropyridine (1.0 g, 3.6 mmol) and 1-methyl-4-(4,4,5,5-tetramethyl-1,3,2-dioxaborolan-2-yl)-1H-pyrazole (1.0 g, 4.6 mmol) were dissolved in dioxane (10 mL). A solution of K₂CO₃ (1.5 g, 10.6 mmol) in water (2 mL) was added and the mixture was sonicated and sparged with Ar for 10 min. Pd(PPh₃)₄ (0.21 g, 0.18 mmol) was added and the reaction mixture was stirred at 80° C. for 24 h. EtOAc (60 mL) was added and the mixture was washed with sat. NaHCO₃ (aq) (60 mL) and brine (60 mL), dried (Na₂SO₄), and concentrated in vacuo to afford 2-ethyl-3-((2-(1-methyl-1H-pyrazol-4-yl)pyridin-4-yl)oxy)-6-nitropyridine (1.2 g, 100%) as a brown viscous oil that was carried forward without further purification. MS (ESI) m/z: 326.1 (M+H⁺).

2-Ethyl-3-((2-(1-methyl-1H-pyrazol-4-yl)pyridin-4-yl)oxy)-6-nitropyridine (1.1 g, 3.2 mmol) and NH₄Cl (6.8 g, 128 mmol) were suspended in MeOH (12 mL) and THF (12 mL) at 0° C. The temperature was carefully maintained while Zn (2.1 g, 31.9 mmol) was added portion-wise over 20 min. The mixture was stirred vigorously for 12 h. EtOAc (75 mL) was added and solids were removed by filtration through a pad of diatomaceous earth. The filter cake was washed with EtOAc (2×15 mL) and the combined filtrates were concentrated in vacuo. The residue was slurried with EtOAc (6 mL) and warmed to 77° C. for 5 min. Solids were collected by filtration, slurried with EtOAc (10 mL), and warmed to 77° C. for 5 min. The slurry was immediately filtered to collect solid product. The filtrates were combined and purified by silica gel chromatography (MeOH/EtOAc). Product material was combined and residual solvent was removed in vacuo to afford 6-ethyl-5-((2-(1-methyl-1H-pyrazol-4-yl)pyridin-4-yl)oxy)pyridin-2-amine (0.48 g, 51%) as an off white solid. ¹H NMR (400 MHz, DMSO-d₆): δ 8.30 (d, J=5.7 Hz, 1H), 8.22 (s, 1H), 7.93 (s, 1H), 7.17 (d, J=8.7 Hz, 1H), 7.11 (d, J=2.4 Hz, 1H), 6.50 (dd, J=5.7, 2.4 Hz, 1H), 6.35 (d, J=8.7 Hz, 1H), 5.94 (s, 2H), 3.84 (s, 3H), 2.39 (q, J=7.5 Hz, 2H), 1.04 (t, J=7.5 Hz, 3H); MS (ESI) m/z: 296.2 (M+H⁺).

6-Ethyl-5-((2-(1-methyl-1H-pyrazol-4-yl)pyridin-4-yl)oxy)pyridin-2-amine (0.15 g, 0.51 mmol) was added to a solution of HF-pyridine (0.76 mL, 8.4 mmol) and pyridine (0.76 mL) at 0° C. and the mixture was stirred for 10 min. Sodium nitrite (0.063 g, 0.91 mmol) was added and the reaction mixture was allowed to warm to RT and stirred for 12 h. The mixture was cooled to 0° C. and poured into cold sat. NaHCO₃ (aq) (5 mL), stirred for 30 min, and extracted with EtOAc (4×10 mL). The combined organics were dried (Na₂SO₄) and concentrated in vacuo to afford 2-ethyl-6-fluoro-3-((24'-methyl-1H-pyrazol-4-yl)pyridin-4-yl)oxy)pyridine (0.15 g, 99%) as a yellow solid that was used in the next step without further purification. MS (ESI) m/z: 299.1 (M+H⁺).

2-Ethyl-6-fluoro-3-((2-(1-methyl-1H-pyrazol-4-yl)pyridin-4-yl)oxy)pyridine (0.15 g, 0.51 mmol) was suspended in 2-propanol (1.0 mL) in a screw-cap reaction vessel. Hydrazine hydrate (0.12 mL, 2.5 mmol) was added, the reaction vessel was sealed and the mixture was stirred at 90° C. for 18 h. Sat. NaHCO₃ (aq) (20 mL) was added and the mixture was extracted wth EtOAc (4×35 mL). The combined organics were dried (Na₂SO₄) and concentrated in vacuo to afford 2-ethyl-6-hydrazinyl-3-((2-(1-methyl-1H-pyrazol-4-yl)pyridin-4-yl)oxy)pyridine (0.15 g, 96%) as a light yellow solid that was used in the next step without further purification. MS (ESI) m/z: 311.2 (M+H⁺).

2-Ethyl-6-hydrazinyl-3-((2-(1-methyl-1H-pyrazol-4-yl)pyridin-4-yl)oxy)pyridine (0.15 g, 0.483 mmol) Example B4 (0.81 g, 4.0 mmol) were suspended in toluene (1 mL), stirred at 45° C. for 30 min, and allowed to cooled to RT. TEA (0.08 mL, 0.57 mmol) was added and the reaction mixture was stirred at 105° C. overnight, cooled to 0° C., and diluted with DCM (4 mL). A solution of bis(trichloromethyl)carbonate (0.2 g, 0.7 mmol) in DCM (2 mL) was added and the mixture was stirred for 1.5 h. Sat. NaHCO₃ (aq) (5 mL) was added the mixture was extracted with DCM (4×5 mL). The combined organics were dried (Na₂SO₄) and concentrated in vacuo. The residue was purified by silica gel chromatography (MeOH/DCM) and again by reverse-phase silica gel chromatography (MeCN/water (0.1% TFA) to afford 3-(tert-butyl)-1-(6-ethyl-5-((2-(1-methyl-1H-pyrazol-4-yl)pyridin-4-yl)oxy)pyridin-2-yl)-1H-1,2,4-triazol-5(4H)-one (0.022 g, 9.2%) as a white solid. ¹H NMR (400 MHz, Acetone-d₆): δ 8.40 (d, J=5.7 Hz, 1H), 8.13 (s, 1H), 7.94 (t, J=4.4 Hz, 2H), 7.63 (d, J=8.7 Hz, 1H), 7.18 (d, J=2.4 Hz, 1H), 6.69 (dd, J=5.7, 2.4 Hz, 1H), 3.90 (s, 3H), 2.74 (d, J=7.5 Hz, 2H), 1.40 (s, 9H), 1.24 (t, J=7.5 Hz, 3H); MS (ESI) m/z: 420.2 (M+H⁺).

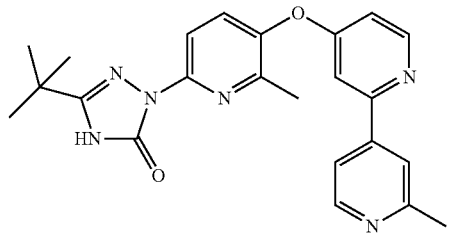 [SMILES: Cc1cc(-c2cc(Oc3ccc(-n4nc(C(C)(C)C)[nH]c4=O)nc3C)ccn2)ccn1]

Example 9

K₂CO₃ (0.1 g, 0.72 mmol) was dissolved in water (0.2 mL) and the solution was diluted with dioxane (1.2 mL). Example A3 (0.10 g, 0.28 mmol) and 2-methyl-4-(4,4,5,5-tetramethyl-1,3,2-dioxaborolan-2-yl)pyridine (0.08 g, 0.37 mmol) were added and the mixture was sonicated and sparged with Ar for 10 min. Pd(PPh₃)₄ (0.04 g, 0.04 mmol) was added and the reaction mixture was stirred at 85° C. for 16 h. EtOAc (5 mL) was added and solids were removed by filtration through a pad of diatomaceous earth. The filter cake was washed with EtOAc (3×5 mL) and the combined filtrates were concentrated in vacuo. The residue was purified by silica gel chromatography (MeOH/DCM). The purified product was dissolved in MeCN and water, frozen to –78° C., and lyophilized to afford 3-(tert-butyl)-1-(6-methyl-5-((2'-methyl-[2,4'-bipyridin]-4-yl)oxy)pyridin-2-yl)-1H-1,2,4-triazol-5(4H)-one (0.038 g, 29.8%) as a yellow solid. ¹H NMR (400 MHz, DMSO-d₆): δ 11.99 (s, 1H), 8.61 (s, 1H), 8.53 (s, 1H), 7.91 (s, 1H), 7.89 (s, 1H), 7.81 (d, J=2.7 Hz, 1H), 7.75 (s, 1H), 7.69 (s, 1H), 6.93 (d, J=2.9 Hz, 1H), 2.53 (s, 3H), 2.35 (s, 3H), 1.28 (s, 9H); MS (ESI) m/z: 417.2 (M+H⁺).

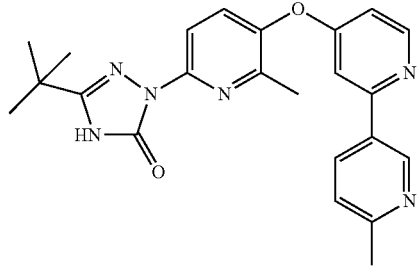 [SMILES: Cc1ccc(-c2cc(Oc3ccc(-n4nc(C(C)(C)C)[nH]c4=O)nc3C)ccn2)cn1]

Example 10

K₂CO₃ (0.1 g, 0.72 mmol) was dissolved in water (0.2 mL) and the solution was diluted with dioxane (1.2 mL). Example A3 (0.10 g, 0.28 mmol) and 2-methyl-4-(4,4,5,5-tetramethyl-1,3,2-dioxaborolan-2-yl)pyridine (0.08 g, 0.37 mmol) were added and the mixture was sonicated and sparged with Ar for 10 min. Pd(PPh$_3$)$_4$ (0.04 g, 0.04 mmol) was added and the reaction mixture was stirred at 85° C. for 16 h. EtOAc (5 mL) was added and solids were removed by filtration through a pad of diatomaceous earth. The filter cake was washed with EtOAc (3×5 mL) and the combined filtrates were concentrated in vacuo. The residue was purified by silica gel chromatography (MeOH/DCM). The isolated product was dissolved in MeCN and water, frozen to −78° C., and lyophilized to afford 3-(tert-butyl)-1-(6-methyl-5-((6'-methyl-[2,3'-bipyridin]-4-yl)oxy)pyridin-2-yl)-1H-1,2,4-triazol-5(4H)-one (0.064 g, 55.0%) as a yellow solid. $^1$H NMR (400 MHz, DMSO-d$_6$): δ 11.99 (s, 1H), 9.11 (s, 1H), 8.57 (s, 1H), 8.29 (d, J=4.2 Hz, 1H), 7.88 (s, 1H), 7.75 (s, 1H), 7.61 (s, 1H), 7.36 (s, 1H), 6.84 (d, J=2.9 Hz, 1H), 2.51 (s, 3H), 2.36 (s, 3H), 1.28 (s, 9H); MS (ESI) m/z: 417.2 (M+H$^+$).

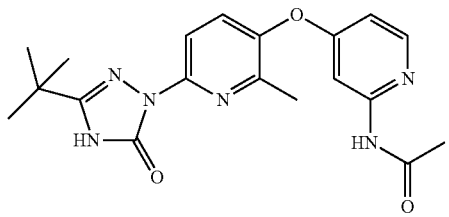 [SMILES: CC(=O)Nc1cc(Oc2ccc(-n3nc(C(C)(C)C)[nH]c3=O)nc2C)ccn1]

Example 11

Example A3 (0.09 g, 0.25 mmol), acetamide (0.065 g, 1.1 mmol), Cs$_2$CO$_3$ (0.09 g, 0.28 mmol), and X-Phos (0.012 g, 0.025 mmol) were combined and suspended in dioxane (1.5 mL) and the mixture was sonicated and sparged with Ar for 10 min. Pd$_2$(dba)$_3$ (0.023 g, 0.025 mmol) was added and the mixture was stirred at 80° C. for 16 h. EtOAc (10 mL) was added and solids were removed by filtration through a pad of diatomaceous earth. The filter cake was washed with EtOAc (3×10 mL) and the combined filtrates were concentrated in vacuo. The residue was purified by silica gel chromatography (MeOH/DCM). The product was dissolved in MeCN and water, frozen to −78° C., and lyophilized to afford N-(4-((6-(3-(tert-butyl)-5-oxo-4,5-dihydro-1H-1,2,4-triazol-1-yl)-2-methylpyridin-3-yl)oxy)pyridin-2-yl)acetamide (0.056 g, 58.5%) as a white solid. $^1$H NMR (400 MHz, DMSO-d$_6$): δ 11.98 (s, 1H), 10.57 (s, 1H), 8.19 (br s, 1H), 7.86 (s, 1H), 7.70 (s, 1H), 7.59 (s, 1H), 6.66-6.66 (m, 1H), 2.30 (s, 3H), 2.03 (s, 3H), 1.27 (s, 9H); MS (ESI) m/z: 383.2 (M+H$^+$).

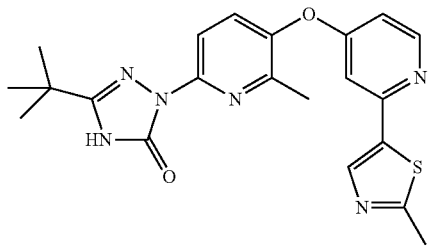 [SMILES: Cc1ncc(-c2cc(Oc3ccc(-n4nc(C(C)(C)C)[nH]c4=O)nc3C)ccn2)s1]

Example 12

Example A3 (0.20 g, 0.56 mmol) and Example D1 (0.28 g, 0.72 mmol) were suspended in toluene (3 mL). The mixture was sonicated and sparged with Ar for 10 minutes. Pd(PPh$_3$)$_4$ (0.03 g, 0.03 mmol) was added and the reaction mixture was stirred at 105° C. for 12 h. Additional Pd(PPh$_3$)$_4$ (0.02 g, 0.02 mmol) was added and stirring was continued at 105° C. for 18 h. The mixture was partitioned between 10% KF (aq) (10 mL) and EtOAc (10 mL) and the biphasic mixture was stirred vigorously at RT for 2 h. The solids were removed by filtration through a plug of diatomaceous earth. The filter cake was washed with EtOAc (3×10 mL) and the combined filtrates were extracted with EtOAc (4×20 mL). The combined organics were dried (MgSO$_4$) and concentrated in vacuo. The residue was purified by silica gel chromatography (MeOH/DCM) to afford 3-(tert-butyl)-1-(6-methyl-5-((2-(2-methylthiazol-5-yl)pyridin-4-yl)oxy)pyridin-2-yl)-1H-1,2,4-triazol-5(4H)-one (0.16 g, 67.8%) as a white solid. $^1$H NMR (400 MHz, DMSO-d$_6$): δ 11.97 (s, 1H), 8.40 (d, J=5.8 Hz, 1H), 8.33 (s, 1H), 7.86 (d, J=8.8 Hz, 1H), 7.71 (d, J=8.8 Hz, 1H), 7.58 (d, J=2.4 Hz, 1H), 6.76 (dd, J=5.8, 2.4 Hz, 1H), 2.65 (s, 3H), 2.34 (s, 3H), 1.27 (s, 9H); MS (ESI) m/z: 423.2 (M+H$^+$).

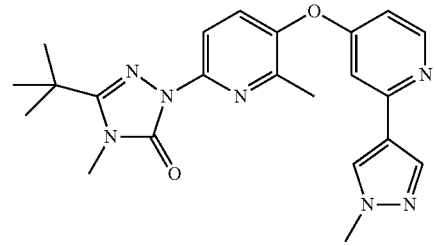 [SMILES: Cc1nc(-n2nc(C(C)(C)C)n(C)c2=O)ccc1Oc1ccnc(-c2cnn(C)c2)c1]

Example 13

A suspension of Example 7 (0.050 g, 0.12 mmol) in acetone (2.5 mL) was treated with Cs$_2$CO$_3$ (0.080 g, 0.25 mmol) and iodomethane (0.02 mL, 0.32 mmol) and the mixture was stirred at RT for 12 h. The solvent was removed in vacuo and the residue was dissolved in DCM (3 mL) and washed with water (3 mL). The aqueous phase was extracted with DCM (4×5 mL) and the combined organics were dried (MgSO$_4$) and concentrated in in vacuo. The residue was triturated with Et$_2$O (2 mL) and sonicated for 5 min, which lead to the precipitation of an off white solid. Solid was isolated by filtration and washed with Et$_2$O (3×1 mL). The solid was dried under high vacuum for 3 h, and was then dissolved in MeCN and water, frozen to −78° C., and lyophilized to afford 3-(tert-butyl)-4-methyl-1-(6-methyl-5-((2-(1-methyl-1H-pyrazol-4-yl)pyridin-4-yl)oxy)pyridin-2-yl)-1H-1,2,4-triazol-5(4H)-one (0.024 g, 46.4%) as an off white solid. $^1$H NMR (400 MHz, DMSO-d$_6$): δ 8.37 (d, J=5.7 Hz, 1H), 8.26 (s, 1H), 7.96 (s, 1H), 7.85 (d, J=8.7 Hz, 1H), 7.72 (d, J=8.7 Hz, 1H), 7.20 (d, J=2.4 Hz, 1H), 6.65 (dd, J=5.7, 2.4 Hz, 1H), 3.84 (s, 3H), 3.39 (s, 3H), 2.34 (s, 3H), 1.37 (s, 9H); MS (ESI) m/z: 420.2 (M+H$^+$).

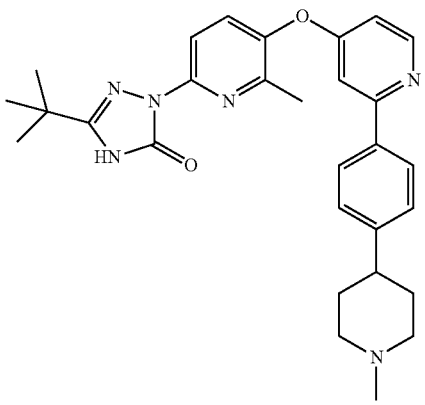 [SMILES: Cc1nc(-n2nc(C(C)(C)C)[nH]c2=O)ccc1Oc1ccnc(-c2ccc(C3CCN(C)CC3)cc2)c1]

Example 14

In a sealed tube, PdCl$_2$(dppf).CH$_2$Cl$_2$ (0.025 g, 0.030 mmol), potassium acetate (0.089 g, 0.908 mmol), bis(pinacolato)diboron (0.115 g, 0.454 mmol) and 4-(4-bromo-phenyl)-1-methyl-piperidine (0.1 g, 0.393 mmol) were suspended in dioxane (6 mL). The mixture was degassed with Ar and heated at 100° C. for 20 h. The reaction was cooled to RT and Example A3 (0.109 g, 0.303 mmol), Pd(PPh$_3$)$_4$ (0.035 g, 0.030 mmol), K$_2$CO$_3$ (0.125 g, 0.908 mmol) and water (1.500 mL) were added. The reaction was degassed with Ar and heated at 100° C. for 3 h. The mixture was partitioned between EtOAc and 1N NaOH and extracted with EtOAc (2×). The combined organic extracts were washed with brine, dried and evaporated. The crude product was purified by reverse phase chromatography (C-18) eluting with water/acetonitrile (0.1% TFA). Fractions containing the desired product were combined and concentrated until mostly water remained. The mixture was made basic with 1N NaOH and extracted with DCM (3×). The combined organic extracts were dried and evaporated to yield the product, which was suspended in acetonitrile (~5 mL) and sonicated for 30 min. The resulting solid was collected by filtration and dried under high vacuum to yield 3-(tert-butyl)-1-(6-methyl-5-((2-(4-(1-methylpiperidin-4-yl)phenyl)pyridin-4-yl)oxy)pyridin-2-yl)-1H-1,2,4-triazol-5(4H)-one (30 mg, 19.9%). $^1$H NMR (400 MHz, DMSO-d$_6$): δ 11.95 (br s, 1H), 8.52 (d, J=5.6 Hz, 1H), 7.94 (d, J=8.2 Hz, 2H), 7.86 (d, J=8.8 Hz, 1H), 7.72 (d, J=8.8 Hz, 1H), 7.42 (d, J=2.4 Hz, 1H), 7.32 (d, J=8.2 Hz, 2H), 6.80 (dd, J=5.6, 2.4 Hz, 1H), 2.85 (d, J=10.9 Hz, 2H), 2.53-2.43 (m, 1H), 2.34 (s, 3H), 2.18 (s, 3H), 1.95 (t, J=11.3 Hz, 2H), 1.76-1.60 (m, 4H), 1.27 (s, 9H); MS (ESI) m/z: 499.3 (M+H$^+$).

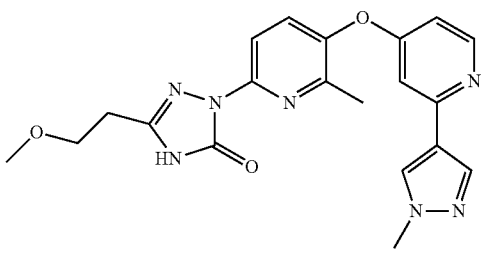 [SMILES: COCCc1nn(-c2ccc(Oc3ccnc(-c4cnn(C)c4)c3)c(C)n2)c(=O)[nH]1]

Example 15

Example A4 (0.20 g, 0.68 mmol) and Example B7 (0.27 g, 1.35 mmol) were suspended in DCM (1.4 mL). The mixture was cooled to 0° C. and stirred for 30 min. TEA (0.60 mL, 4.30 mmol) was added dropwise and the reaction mixture was warmed to 40° C. and stirred for 12 h. Sat. NH$_4$Cl (aq) (3 mL) was added and the mixture was extracted with EtOAc (4×5 mL). The combined organics were dried (Na$_2$SO$_4$) and concentrated in vacuo. The residue was purified by silica gel chromatography (MeOH/DCM) to afford 3-(2-methoxyethyl)-1-(6-methyl-5-((2-(1-methyl-1H-pyrazol-4-yl)pyridin-4-yl)oxy)pyridin-2-yl)-1H-1,2,4-triazol-5(4H)-one (0.18 g, 63.8%) as white solid. $^1$H NMR (400 MHz, DMSO-d$_6$): δ 11.90 (s, 1H), 8.37 (d, J=5.7 Hz, 1H), 8.26 (s, 1H), 7.96 (d, J=0.7 Hz, 1H), 7.88 (d, J=8.8 Hz, 1H), 7.69 (d, J=8.8 Hz, 1H), 7.19 (d, J=2.4 Hz, 1H), 6.65 (dd, J=5.7, 2.4 Hz, 1H), 3.84 (s, 3H), 3.63 (t, J=6.4 Hz, 2H), 3.26 (s, 3H), 2.76 (t, J=6.4 Hz, 2H), 2.33 (s, 3H). MS (ESI) m/z: 408.2 (M+H$^+$).

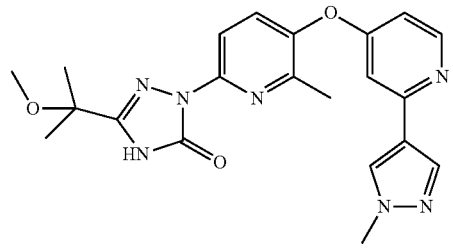 [SMILES: COC(C)(C)c1nn(-c2ccc(Oc3ccnc(-c4cnn(C)c4)c3)c(C)n2)c(=O)[nH]1]

Example 16

Example C2 (0.075 g, 0.48 mmol), copper(I) iodide (0.01 g, 0.05 mmol), and K$_2$CO$_3$ (0.20 g, 1.45 mmol) were suspended in DMF (1 mL). The mixture was sonicated and sparged with Ar for 10 min. Example A1 (0.34 g, 0.98 mmol) and N,N-dimethylethane-1,2-diamine (10 mg, 0.11 mmol) were sequentially added and the mixture was stirred under an atmosphere of Ar at 100° C. for 12 h. Water (10 mL) was added and the mixture was extracted with EtOAc (5×10 mL). The combined organics were dried (Na$_2$SO$_4$) and concentrated in vacuo. The residue was purified by silica gel chromatography (MeOH/DCM) to afford 3-(2-methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.1 g, 55.8%) as a brown oil. $^1$H NMR (400 MHz, DMSO-d$_6$): δ 9.63 (s, 1H), 8.30 (d, J=5.7 Hz, 1H), 8.03 (d, J=8.8 Hz, 1H), 7.71 (d, J=8.8 Hz, 1H), 7.00 (d, J=2.2 Hz, 1H), 6.96 (dd, J=5.7, 2.3 Hz, 1H), 3.18 (s, 3H), 2.38 (s, 3H), 1.56 (s, 6H); MS (ESI) m/z: 376.2 (M+H$^+$).

3-(2-Methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.10 g, 0.27 mmol) and 1-methyl-4-(4,4,5,5-tetramethyl-1,3,2-dioxaborolan-2-yl)-1H-pyrazole were dissolved in dioxane (2.2 mL). A solution of K$_2$CO$_3$ (0.10 g, 0.7 mmol) in water (0.44 mL) was added and the mixture was sonicated and sparged with Ar for 10 min. Pd(PPh$_3$)$_4$ (0.03 g, 0.03 mmol) was added and the reaction mixture was stirred at 85° C. for 12 h. Sat. NaHCO$_3$ (aq) (10 mL) was added and the mixture was extracted with EtOAc (5×10 mL). The combined organics were dried (Na$_2$SO$_4$), concentrated in vacuo, and the residue was purified by silica gel chromatography (MeOH/DCM). The product was suspended in MeCN (1 mL) and sonicated for 5 min. The solvent solvent was removed by decantation. The residual solid was dissolved in MeCN and water, frozen to −78° C., and lyophilized to afford 3-(2-methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.026 g, 22.8%) as a white solid. ¹H NMR (400 MHz, DMSO-d₆): δ 12.15 (s, 1H), 8.37 (d, J=5.7 Hz, 1H), 8.26 (s, 1H), 7.96 (d, J=0.7 Hz, 1H), 7.89 (d, J=8.8 Hz, 1H), 7.70 (d, J=8.8 Hz, 1H), 7.19 (d, J=2.4 Hz, 1H), 6.66 (dd, J=5.7, 2.4 Hz, 1H), 3.84 (s, 3H), 3.07 (s, 3H), 2.34 (s, 3H), 1.48 (s, 6H); MS (ESI) m/z: 422.2 (M+H⁺).

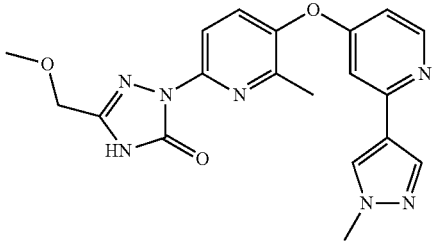 [SMILES: COCc1nn(-c2ccc(Oc3ccnc(-c4cnn(C)c4)c3)c(C)n2)c(=O)[nH]1]

Example 17

Example A4 (0.20 g, 0.68 mmol) and Example B8 (0.26 g, 1.4 mmol) were suspended in DCM (1.4 mL). The mixture was cooled to 0° C. and stirred for 30 min. TEA (0.60 mL, 4.3 mmol) was added dropwise and the mixture was stirred at 40° C. for 12 h. Sat. NH₄Cl (aq) (15 mL) was added and the mixture was extracted with DCM (4×10 mL). The combined organics were dried (Na₂SO₄) and concentrated in vacuo. The residue was purified by silica gel chromatography (MeOH/DCM). The product was further purified by trituration with MeCN (2 mL), and was then dissolved in MeCN and water, frozen to −78° C., and lyophilized to afford 3-(methoxymethyl)-1-(6-methyl-5-((2-(1-methyl-1H-pyrazol-4-yl)pyridin-4-yl)oxy)pyridin-2-yl)-1H-1,2,4-triazol-5(4H)-one (0.035 g, 12%) as a light yellow solid. ¹H NMR (400 MHz, DMSO-d₆): δ 12.24-12.22 (m, 1H), 8.37 (d, J=5.7 Hz, 1H), 8.26 (s, 1H), 7.96 (d, J=0.7 Hz, 1H), 7.91 (d, J=8.8 Hz, 1H), 7.71 (d, J=8.8 Hz, 1H), 7.21 (d, J=2.4 Hz, 1H), 6.65 (dd, J=5.7, 2.4 Hz, 1H), 4.33 (s, 2H), 3.84 (s, 3H), 3.31 (s, 3H), 2.33 (s, 3H); MS (ESI) m/z: 394.2 (M+H⁺).

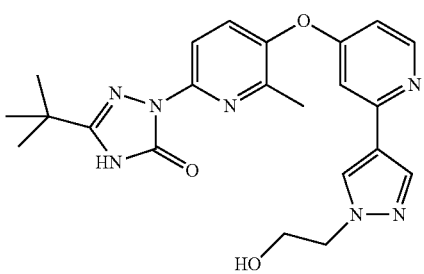 [SMILES: Cc1nc(-n2nc(C(C)(C)C)[nH]c2=O)ccc1Oc1ccnc(-c2cnn(CCO)c2)c1]

Example 18

Example A3 (0.20 g, 0.56 mmol) and Example D2 (0.14 g, 0.43 mmol) were dissolved in dioxane (1.8 mL). A solution of K₂CO₃ (0.15 g, 1.11 mmol) in water (0.36 mL) was added and the mixture was sonicated and sparged with Ar for 10 min. Pd(PPh₃)₄ (0.05 g, 0.04 mmol) was added and the mixture was stirred at 85° C. for 12 h. Water (5 mL) was added and the mixture was extracted with EtOAc (4×15 mL). The combined organics were dried (Na₂SO₄) and concentrated in vacuo to afford 3-(tert-butyl)-1-(6-methyl-5-((2-(1(2-((tetrahydro-2H-pyran-2-yl)oxy)ethyl)-1H-pyrazol-4-yl)pyridin-4-yl)oxy)pyridin-2-yl)-1H-1,2,4-triazol-5(4H)-one (0.18 g, 80%) as a yellow oil that was used in the next step without further purification. MS (ESI) m/z: 520.3 (M+H⁺).

3-(tert-Butyl)-1-(6-methyl-5-((2-(1-(2-((tetrahydro-2H-pyran-2-yl)oxy)ethyl)-1H-pyrazol-4-yl)pyridin-4-yl)oxy)pyridin-2-yl)-1H-1,2,4-triazol-5(4H)-one (0.18 g, 0.34 mmol) was dissolved in MeCN and treated with a HCl (4 M in dioxane) (0.25 mL, 1.0 mmol). The mixture was stirred at RT for 20 min. Sat. NaHCO₃ (aq) (15 mL) was added and the suspension was extracted with EtOAc (5×15 mL). The combined organics were dried (Na₂SO₄) and concentrated in vacuo. The residue was purified by silica gel chromatography (MeOH/DCM). The product was triturated with MeCN (5 mL) and sonicated for 5 min. The solid was isolated by filtration, redissolved in MeCN and water, frozen to −78° C., and lyophilized to afford 3-(tert-butyl)-1-(5-((2-(1-(2-hydroxyethyl)-1H-pyrazol-4-yl)pyridin-4-yl)oxy)-6-methylpyridin-2-yl)-1H-1,2,4-triazol-5(4H)-one (0.13 g, 82%) as an off white solid. ¹H NMR (400 MHz, DMSO-d₆): δ 11.97 (s, 1H), 8.37 (d, J=5.7 Hz, 1H), 8.27 (s, 1H), 7.99 (s, 1H), 7.85 (d, J=8.8 Hz, 1H), 7.68 (d, J=8.8 Hz, 1H), 7.21 (d, J=2.4 Hz, 1H), 6.64 (dd, J=5.7, 2.4 Hz, 1H), 4.89 (t, J=5.3 Hz, 1H), 4.13 (t, J=5.6 Hz, 2H), 3.73 (q, J=5.5 Hz, 2H), 2.33 (s, 3H), 1.27 (s, 9H); MS (ESI) m/z: 436.2 (M+H⁺).

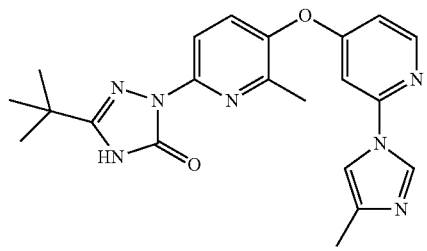 [SMILES: Cc1cn(-c2cc(Oc3ccc(-n4nc(C(C)(C)C)[nH]c4=O)nc3C)ccn2)cn1]

Example 19

To a degassed solution of dioxane (12 mL) and toluene (3 mL) was added Pd₂(dba)₃ (0.020 g, 0.022 mmol) and Me₄tBuXPhos (0.020 g, 0.042 mmol) and the mixture was heated in a sealed vessel (vol. 40 mL) at 110° C. for 5 minutes. The reaction mixture was cooled to RT and Example A3 (0.250 g, 0.695 mmol), 4-methylimidazole (0.100 g, 1.218 mmol) and potassium phosphate (0.300 g, 1.413 mmol) were added. The vessel was sealed and heated at 110° C. for 14 hours. The reaction mixture was filtered and washed well with DCM and THF. The filtrate was completely evaporated and the residue was subjected to reverse phase chromatography using [10-90% MeCN-water (containing 1% TFA)] to provide colorless oily mass, which on lyophilization after dissolving in a mixture of MeCN (2 mL) and water (2 mL) provided 3-(tert-butyl)-1-(6-methyl-5-((2-(4-methyl-1H-imidazol-1-yl)pyridin-4-yl)oxy)pyridin-2-yl)-1H-1,2,4-triazol-5(4H)-one (0.070 g, 25% yield) as white solid. ¹H NMR (400 MHz, DMSO-d₆): δ 12.00 (s, 1H), 9.58 (s, 1H), 8.47 (d, J=5.8 Hz, 1H), 8.11 (s, 1H), 7.90 (d, J=8.8 Hz, 1H), 7.74 (d, J=8.8 Hz, 1H), 7.52 (d, J=2.2 Hz, 1H), 7.07 (dd, J=5.8, 2.2 Hz, 1H), 2.34 (s, 3H), 2.29 (s, 3H), 1.27 (s, 9H); MS (ESI) m/z: 406.2 (M+H⁺).

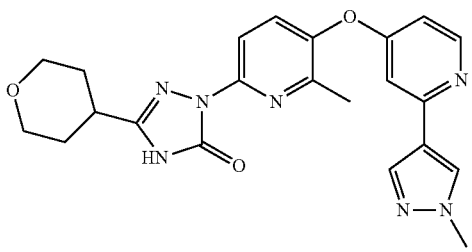 [SMILES: Cc1nc(-n2nc(C3CCOCC3)[nH]c2=O)ccc1Oc1ccnc(-c2cnn(C)c2)c1]

Example 20

Example A4 (0.2 g, 0.675 mmol) was suspended in DCM (3 mL) and cooled to 0° C. A solution of Example B10 (0.309 g, 1.350 mmol) in DCM (3.75 mL) was added and the mixture stirred for 30 min. The reaction was allowed to warm to RT and TEA (0.659 mL, 4.72 mmol) was added. The mixture was heated at 40° C. for 3 days. The reaction was cooled to RT and partitioned between DCM and saturated NaHCO$_3$ (aq) and the aqueous was extracted with DCM (2×). The organic extracts were combined, washed with brine, dried and evaporated. The crude product was purified silica gel chromatography eluting with DCM/MeOH to give the product which was purified further by preparatory silica gel TLC eluting with DCM/MeOH. The desired product was dissolved in acetonitrile/water, frozen and lyophilized to yield 1-(6-methyl-5-((2-(1-methyl-1H-pyrazol-4-yl)pyridin-4-yl)oxy)pyridin-2-yl)-3-(tetrahydro-2H-pyran-4-yl)-1H-1,2,4-triazol-5(4H)-one (9 mg, 3%). $^1$H NMR (400 MHz, DMSO-d$_6$): δ 11.98 (s, 1H), 8.37 (d, J=5.7 Hz, 1H), 8.26 (s, 1H), 7.96 (d, J=0.7 Hz, 1H), 7.87 (d, J=8.8 Hz, 1H), 7.69 (d, J=8.8 Hz, 1H), 7.19 (d, J=2.4 Hz, 1H), 6.64 (dd, J=5.7, 2.4 Hz, 1H), 3.90-3.89 (m, 2H), 3.84 (s, 3H), 3.41 (td, J=11.5, 2.2 Hz, 2H), 2.85-2.84 (m, 1H), 2.33 (s, 3H); 1.84-1.82 (m, 2H), 1.71-1.69 (m, 2H); MS (ESI) m/z: 434.2 (M+H$^+$).

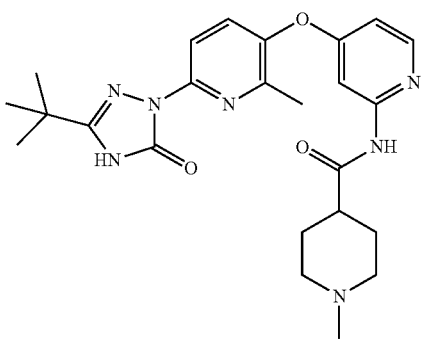 [SMILES: Cc1nc(-n2nc(C(C)(C)C)[nH]c2=O)ccc1Oc1ccnc(NC(=O)C2CCN(C)CC2)c1]

Example 21

A round bottom flask was charged with Example A3 (0.189 g, 0.525 mmol) in dioxane (5 mL) and sparged with Ar under sonication for 20 minutes after which 1-methylpiperidine-4-carboxamide (0.149 g, 1.051 mmol), Cs$_2$CO$_3$ (0.342 g, 1.051 mmol), and DPPF (0.029 g, 0.053 mmol) was added and the mixture sparged with Ar under sonication for 15 minutes. Pd$_2$(dba)$_3$ (0.024 g, 0.026 mmol) was added and the mixture was sparged with Ar under sonication for 15 minutes. The reaction was then heated to 100° C. under Ar and stirred overnight. The reaction mixture was cooled to RT, sparged with Ar under sonication and added Pd$_2$(dba)$_3$ (0.024 g, 0.026 mmol), DPPF (0.029 g, 0.053 mmol), sparged with Ar under sonication and then heated to 100° C. and stirred overnight. The reaction mixture was cooled to RT, sparged with Ar under sonication and added Pd$_2$(dba)$_3$ (0.024 g, 0.026 mmol), DPPF (0.029 g, 0.053 mmol), sparged with Ar under sonication and then heated to 100° C. and stirred overnight. The reaction mixture was cooled to RT, diluted with EtOAc and filtered through diatomaceous earth and washed with EtOAc. The filtrates were concentrated to dryness to afford a brown solid. The crude product was subject to reverse-phase silica gel chromatography (10%-45% MeCN/water, 0.1% TFA). The appropriate fractions were collected, concentrated and stirred with EtOAc and sat'd NaHCO$_3$. The aqueous layer was back-extracted with EtOAc (3×), the organic phases combined, dried (Na$_2$SO$_4$) and concentrated to dryness to afford a white solid. The product was suspended in MeCN/H$_2$O, frozen and lyophilized overnight to furnish N-(4-((6(3-(tert-butyl)-5-oxo-4,5-dihydro-1H-1,2,4-triazol-1-yl)-2-methylpyridin-3-yl)oxy)pyridin-2-yl)-1-methylpiperidine-4-carboxamide an off white solid. (0.0428 g, 16.5%). $^1$H NMR (400 MHz, DMSO-d$_6$): δ 11.98 (br s, 1H), 10.52 (s, 1H), 8.19 (d, J=5.7 Hz, 1H), 7.86 (d, J=8.8 Hz, 1H), 7.69 (d, J=8.8 Hz, 1H), 7.58 (d, J=2.4 Hz, 1H), 6.69 (dd, J=5.7, 2.4 Hz, 1H), 2.81-2.71 (m, 2H), 2.41-2.33 (m, 1H), 2.29 (s, 3H), 2.13 (s, 3H), 1.87-1.76 (m, 2H), 1.71-1.62 (m, 2H), 1.56-1.47 (m, 2H), 1.27 (s, 9H); MS (ESI) m/z: 466.3 (M+H$^+$).

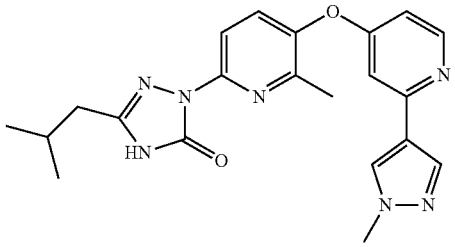 [SMILES: Cc1nc(-n2nc(CC(C)C)[nH]c2=O)ccc1Oc1ccnc(-c2cnn(C)c2)c1]

Example 22

Example A4 (0.20 g, 0.68 mmol) was suspended in DCM (6 mL) and cooled to 0° C. Example B9 (0.27 g, 1.4 mmol) was added and the reaction mixture was allowed to warm to RT, stirred for 30 min, and cooled back to 0° C. TEA (0.56 mL, 4.1 mmol) was added dropwise and the mixture was stirred at RT for 12 h. Sat. NH$_4$Cl (aq) (15 mL) was added and the resultant suspension was extracted with DCM (4×10 mL). The combined organics were dried (Na$_2$SO$_4$) and concentrated in vacuo. The resultant residue was purified by a three step sequence involving silica gel chromatography (MeOH/DCM), reverse-phase chromatography (30 g C18 column) [MeCN (0.1% TFA)/water (0.1% TFA)], and additional silica gel chromatography (EtOAc/DCM and MeOH/EtOAc) to afford a colorless solid. The isolated product was dissolved in MeCN/water, frozen to −78° C., and lyophilized to afford 3-(methoxymethyl)-1-(6-methyl-5-((2-(1-methyl-1H-pyrazol-4-yl)pyridin-4-yl)oxy)pyridin-2-yl)-1H-1,2,4-triazol-5(4H)-one (0.030 g, 10.8%) as a white solid. $^1$H NMR (400 MHz, DMSO-d$_6$): δ 8.34 (d, J=5.7 Hz, 1H), 8.24 (s, 1H), 8.18-8.17 (m, 1H), 7.95 (d, J=0.7 Hz, 1H), 7.53-7.52 (m, 1H), 7.15 (d, J=2.4 Hz, 1H), 6.60 (dd, J=5.7, 2.4 Hz, 1H), 3.83 (s, 3H), 2.27 (s, 3H), 1.97-1.96 (m, 1H), 1.63-1.61 (m, 2H), 0.90 (d, J=6.6 Hz, 6H); MS (ESI) m/z: 406.2 (M+H$^+$).

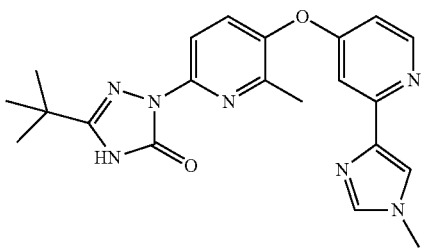 [SMILES: Cc1nc(-n2nc(C(C)(C)C)[nH]c2=O)ccc1Oc1ccnc(-c2cn(C)cn2)c1]

Example 23

To a degassed solution of Example A3 (0.200 g, 0.556 mmol) in toluene (10 mL) was added N-methyl-4-(tributylstannyl)imidazole (0.400 g, 1.078 mmol) followed by Pd(PPh$_3$)$_4$ (0.040 g, 0.035 mmol) and the resultant mixture was heated in a sealed tube (vol. 20 mL) at 105° C. over night. The reaction mixture was diluted with EtOAc (8 mL) and stirred with aq KF solution for 1 h. The organic layer was separated and the aqueous layer extracted with DCM (2×10 mL) and combined with the previous organic layer. The organic layer was directly subjected to chromatography using (0-20% MeOH/DCM) to provide 3-(tert-butyl)-1-(6-methyl-5-((2-(1-methyl-1H-imidazol-4-yl)pyridin-4-yl)oxy)pyridin-2-yl)-1H-1,2,4-triazol-5(4H)-one (0.060 g, 25% yield) as a white solid. $^1$H NMR (400 MHz, dmso): δ 11.98 (s, 1H), 8.37 (d, J=5.7 Hz, 1H), 7.86 (d, J=8.7 Hz, 1H), 7.73 (d, J=8.8 Hz, 1H), 7.68 (d, J=1.3 Hz, 1H), 7.59 (s, 1H), 7.17 (d, J=2.6 Hz, 1H), 6.79 (dd, J=5.7, 2.6 Hz, 1H), 3.67 (s, 3H), 2.31 (s, 3H), 1.27 (s, 9H); MS (ESI) m/z: 406.2 (M+H$^+$).

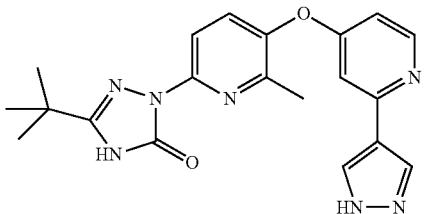 [SMILES: Cc1nc(-n2nc(C(C)(C)C)[nH]c2=O)ccc1Oc1ccnc(-c2cn[nH]c2)c1]

Example 24

A mixture of Example A3 (0.060 g, 0.17 mmol), 4-(4,4,5,5-tetramethyl-1,3,2-dioxaborolan-2-yl)-1H-pyrazole (0.042 g, 0.22 mmol) and K$_2$CO$_3$ (0.060 g, 0.43 mmol) were suspended in dioxane (0.70 mL) and water (0.14 mL). The mixture was sonicated and sparged with Ar for 10 min. Pd(PPh$_3$)$_4$ (0.019 g, 0.017 mmol) was added and the reaction mixture was stirred at 85° C. for 12 h. EtOAc (10 mL) was added and solids were removed by filtration through a pad of diatomaceous earth. The filter cake was washed with EtOAc (3×5 mL) and the combined filtrates were concentrated in vacuo. The residue was purified by silica gel chromatography (MeOH/DCM) to afford 1-(5-((2-(1H-pyrazol-4-yl)pyridin-4-yl)oxy)-6-methylpyridin-2-yl)-3-(tert-butyl)-1H-1,2,4-triazol-5(4H)-one (0.042 g, 64%) as a white solid. $^1$H NMR (400 MHz, acetone-d$_6$): δ 10.70 (m, 1H), 8.42 (d, J=5.7 Hz, 1H), 8.18-8.16 (m, 1H), 7.97 (d, J=8.7 Hz, 1H), 7.63 (d, J=8.7 Hz, 1H), 7.26 (d, J=2.4 Hz, 1H), 6.68 (dd, J=5.7, 2.4 Hz, 1H), 2.39 (s, 3H), 1.40 (s, 9H); MS (ESI) m/z: 392.2 (M+H$^+$).

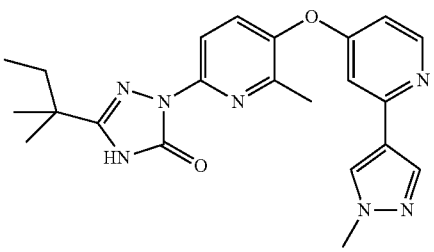 [SMILES: CCC(C)(C)c1nn(-c2ccc(Oc3ccnc(-c4cnn(C)c4)c3)c(C)n2)c(=O)[nH]1]

Example 25

Example C3 (0.21 g, 1.3 mmol), copper(I) iodide (0.050 g, 0.26 mmol), and K$_2$CO$_3$ (1.0 g, 7.2 mmol) were suspended in DMF (6 mL) under an atmosphere of Ar. Example A1 (0.50 g, 1.4 mmol) and N,N-dimethylethane-1,2-diamine (0.023 g, 0.26 mmol) were added sequentially and the reaction mixture was stirred at 100° C. for 12 h. Sat. NH$_4$Cl (aq) (30 mL) was added and the resultant emulsion was extracted with EtOAc (5×25 mL). The combined organics were dried and concentrated in vacuo to afford a yellow oil that was triturated with MeCN (5 mL) and sonicated for 30 min. The resultant suspension was collected by filtration and washed with cold MeCN (2×2.5 mL) to afford 1-(5-((2-chloropyridin-4-yl)oxy)-6-methylpyridin-2-yl)-3-(tert-pentyl)-1H-1,2,4-triazol-5(4H)-one (0.44 g, 89%) as a light yellow solid that was carried forward without further purification. MS (ESI) m/z: 374.1 (M+H$^+$).

1-(5-((2-Chloropyridin-4-yl)oxy)-6-methylpyridin-2-yl)-3-(tert-pentyl)-1H-1,2,4-triazol-5(4H)-one (0.15 g, 0.40 mmol), 1-methyl-4-(4,4,5,5-tetramethyl-1,3,2-dioxaborolan-2-yl)-1H-pyrazole (0.11 g, 0.52 mmol), and K$_2$CO$_3$ (0.14 g, 1.04 mmol) were suspended in dioxane (1.7 mL) and water (0.33 mL). The suspension was sonicated and sparged with Ar for 10 min. Pd(PPh$_3$)$_4$ (0.046 g, 0.040 mmol) was added and the reaction mixture was stirred at 85° C. for 12 h. EtOAc (15 mL) was added and the suspension was filtered through a pad of diatomaceous earth. The filter cake was washed with EtOAc (3×5 mL) and the combined filtrates were concentrated in vacuo. The residue was purified by silica gel chromatography (MeOH/DCM). Product was isolated as a colorless oil that was dissolved in MeCN/water, frozen to −78° C., and lyophilized to afford 1-(6-methyl-5-((2-(1-methyl-1H-pyrazol-4-yl)pyridin-4-yl)oxy)pyridin-2-yl)-3-(tert-pentyl)-1H-1,2,4-triazol-5(4H)-one (0.143 g, 79%) as a white solid. $^1$H NMR (400 MHz, DMSO-d$_6$): δ 11.91 (s, 1H), 8.37 (d, J=5.7 Hz, 1H), 8.25 (s, 1H), 7.96 (s, 1H), 7.86 (d, J=8.7 Hz, 1H), 7.68 (d, J=8.7 Hz, 1H), 7.18 (s, 1H), 6.66 (d, J=5.6 Hz, 1H), 3.84 (s, 3H), 2.33 (s, 3H), 1.61 (q, J=7.6 Hz, 2H), 1.23 (s, 6H), 0.76 (t, J=7.3 Hz, 3H); MS (ESI) m/z: (M+H$^+$).

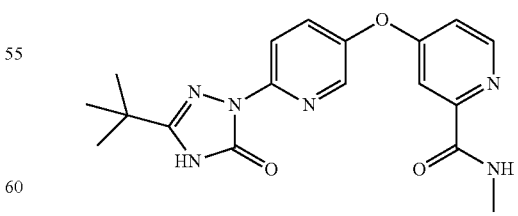

Example 26

Example C1 (0.055 g, 0.392 mmol), copper (I) iodide (0.011 g, 0.060 mmol), Example A7 (0.107 g, 0.301 mmol), N,N-dimethylethane-1,2-diamine (5.31 mg, 0.060 mmol) and K$_2$CO$_3$ (0.230 g, 1.663 mmol) were suspended in DMF (3 mL) and degassed with Ar. The reaction mixture was stirred at 100° C. for 20 h. The reaction was cooled to RT and partitioned between DCM and saturated NH$_4$Cl (aq). The mixture was extracted with saturated NH$_4$Cl (aq) (2×). The combined aqueous extracts were back-extracted with DCM (3×). The organic extracts were combined, dried and evaporated. The crude product was purified by silica gel chromatography eluting with EtOAc/MeOH to give the product, which was purified further by silica gel preparatory TLC eluting with DCM/MeOH to give the desired product. The product was dissolved in MeCN/water, frozen and lyophilized to yield 4-((6-(3-(tert-butyl)-5-oxo-4,5-dihydro-1H-1,2,4-triazol-1-yl)pyridin-3-yl)oxy)-N-methylpicolinamide (27 mg, 24.3%). $^1$H NMR (400 MHz, DMSO-d$_6$): δ 12.02-11.98 (m, 1H), 8.79-8.76 (m, 1H), 8.54 (d, J=5.6 Hz, 1H), 8.44 (d, J=2.7 Hz, 1H), 8.07 (d, J=8.9 Hz, 1H), 7.87-7.85 (m, 1H), 7.44 (d, J=2.4 Hz, 1H), 7.21 (dd, J=5.4, 2.4 Hz, 1H), 2.78 (d, J=4.8 Hz, 3H), 1.27 (s, 9H); MS (ESI) m/z: 369.2 (M+H$^+$).

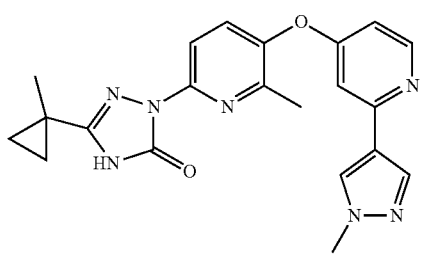 [SMILES: Cc1nc(-n2nc(C3(C)CC3)[nH]c2=O)ccc1Oc1ccnc(-c2cnn(C)c2)c1]

Example 27

Example C4 (0.18 g, 1.3 mmol), copper(I) iodide (0.050 g, 0.26 mmol), and K$_2$CO$_3$ (1.0 g, 7.2 mmol) were suspended in DMF (6 mL) under an atmosphere of Ar. Example A1 (0.50 g, 1.4 mmol) and N,N-dimethylethane-1,2-diamine (0.023 g, 0.26 mmol) were added sequentially and the reaction mixture was stirred at 100° C. for 12 h. Sat. NH$_4$Cl (aq) (30 mL) was added and the resultant emulsion was extracted with EtOAc (5×25 mL). The combined organics were dried and concentrated in vacuo to afford a yellow oil that was triturated with EtOAc (5 mL) and sonicated for 30 min. The resultant suspension was filtered and washed with cold EtOAc (2×2.5 mL) to afford 1-(5-((2-chloropyridin-4-yl)oxy)-6-methylpyridin-2-yl)-3-(1-methylcyclopropyl)-1H-1,2,4-triazol-5(4H)-one (0.32 g, 68.2%) as a white amorphous solid that was carried forward without further purification. MS (ESI) m/z: 358.1 (M+H$^+$).

1-(5-((2-Chloropyridin-4-yl)oxy)-6-methylpyridin-2-yl)-3-(1-methylcyclopropyl)-1H-1,2,4-triazol-5(4H)-one (0.10 g, 0.28 mmol), 1-methyl-4-(4,4,5,5-tetramethyl-1,3,2-dioxaborolan-2-yl)-1H-pyrazole (0.08 g, 0.36 mmol), and K$_2$CO$_3$ (0.10 g, 0.73 mmol) were suspended in dioxane (1.7 mL) and water (0.33 mL). The suspension was sonicated and sparged with Ar for 10 min. Pd(PPh$_3$)$_4$ (0.032 g, 0.028 mmol) was added and the reaction mixture was stirred at 85° C. for 12 h. Sat. NH$_4$Cl (aq) (10 mL) was added and the resultant emulsion was extracted with EtOAc (4×10 mL). The combined organics were dried (Na$_2$SO$_4$) and concentrated in vacuo. The residue was purified by silica gel chromatography (MeOH/DCM) to afford 1-(6-methyl-5-((2-(1-methyl-1H-pyrazol-4-yl)pyridin-4-yl)oxy)pyridin-2-yl)-3-(1-methylcyclopropyl)-1H-1,2,4-triazol-5(4H)-one (0.052 g, 46.1%) as an white solid. $^1$H NMR (400 MHz, DMSO-d$_6$): δ 11.76 (s, 1H), 8.37 (d, J=5.7 Hz, 1H), 8.25 (s, 1H), 7.96 (s, 1H), 7.83 (d, J=8.8 Hz, 1H), 7.68 (d, J=8.8 Hz, 1H), 7.19 (d, J=2.4 Hz, 1H), 6.64 (dd, J=5.7, 2.4 Hz, 1H), 3.84 (s, 3H), 2.33 (s, 3H), 1.38 (s, 3H), 1.06 (d, J=2.3 Hz, 2H), 0.81 (t, J=2.3 Hz, 2H); MS (ESI) m/z: 404.2 (M+H$^+$).

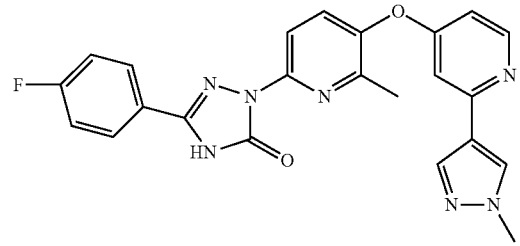 [SMILES: Cc1nc(-n2nc(-c3ccc(F)cc3)[nH]c2=O)ccc1Oc1ccnc(-c2cnn(C)c2)c1]

Example 28

A suspension of Example A8 (0.300 g, 0.754 mmol), 1-methyl-4-(4,4,5,5-tetramethyl-1,3,2-dioxaborolan-2-yl)-1H-pyrazole (0.250 g, 1.202 mmol), K$_2$CO$_3$ (0.200 g, 1.447 mmol) in a mixture of dioxane/water (10:1) (11 mL) was degassed for 5 minutes with argon purge. The reaction mixture was treated with Pd(PPh$_3$)$_4$ (0.020 g, 0.017 mmol) and heated at 100° C. under argon over night. The solvent from the reaction mixture was completely evaporated and the residue was partitioned between DCM (30 mL) and water (30 mL). The organic layer separated and the aqueous layer extracted with dichloromethane (2×15 mL). The combined organics were dried and concentrated to a small volume and purified by silica gel chromatography (0-100% THF/DCM) to provide 3-(4-fluorophenyl)-1-(6-methyl-5-((2-(1-methyl-1H-pyrazol-4-yl)pyridin-4-yl)oxy)pyridin-2-yl)-1H-1,2,4-triazol-5(4H)-one (0.152 g, 45%) as white solid. $^1$H NMR (400 MHz, DMSO-d$_6$): δ 12.71 (s, 1H), 8.38 (d, J=5.7 Hz, 1H), 8.27 (s, 1H), 7.98-7.94 (m, 4H), 7.74 (d, J=8.8 Hz, 1H), 7.40 (t, J=8.8 Hz, 2H), 7.23 (d, J=2.4 Hz, 1H), 6.67 (dd, J=5.7, 2.4 Hz, 1H), 3.84 (s, 3H), 2.37 (s, 3H); MS (ESI) m/z: 444.2 (M+H$^+$).

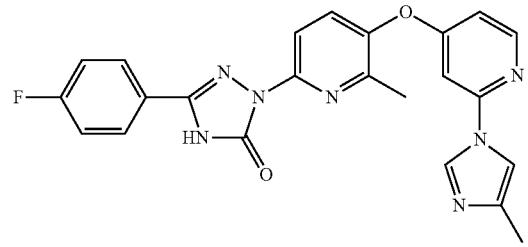 [SMILES: Cc1cn(-c2cc(Oc3ccc(-n4nc(-c5ccc(F)cc5)[nH]c4=O)nc3C)ccn2)cn1]

Example 29

A solution of Pd$_2$(dba)$_3$ (0.012 g, 0.013 mmol) and Me$_4$tBuXPhos (0.012 g, 0.025 mmol) in toluene (2 mL) and dioxane (4 mL) was heated in a screw capped tube (10 mL) at 120° C. for 3 min. The reaction mixture was cooled to RT and the pre-formed catalyst was transferred to a re-sealable pressure tube (50 mL) containing a degassed suspension of Example A8 (0.250 g, 0.628 mmol), 4-methyl imadazole (0.100 g, 1.218 mmol) and potassium phosphate (0.250 g, 1.178 mmol) in a mixture of toluene (4 mL) and dioxane (8 mL) followed by heating at 110° C. for 8 hours. The solids from the reaction mixture was filtered and washed with DCM and THF. The filtrate was completely evaporated and the residue was subjected to chromatography using (0-15% MeOH/DCM) to provide 3-(4-fluorophenyl)-1-(6-methyl-5-((2-(4-methyl-1H-imidazol-1-yl)pyridin-4-yl)oxy)pyridin-2-yl)-1H-1,2,4-triazol-5(4H)-one (0.050 g, 18% yield) as white solid. ¹H NMR (400 MHz, DMSO-d₆): δ 12.71 (s, 1H), 8.41 (d, J=1.4 Hz, 1H), 8.34 (d, J=5.8 Hz, 1H), 7.98-7.93 (m, 3H), 7.78 (d, J=8.8 Hz, 1H), 7.65 (t, J=1.3 Hz, 1H), 7.48 (br s, 1H), 7.40 (m, 2H), 6.82 (dd, J=5.8, 2.2 Hz, 1H), 2.38 (s, 3H), 2.13 (s, 3H); MS (ESI) m/z: 444.2 (M+H⁺).

centrated in vacuo. The residue was purified by silica gel chromatography (MeOH/DCM) to afford 3-(tert-butyl)-1-(4-methyl-5-((2-(1-methyl-1H-pyrazol-4-yl)pyridin-4-yl)oxy)pyridin-2-yl)-1H-1,2,4-triazol-5(4H)-one (0.122 g, 46.3%) as a white solid. ¹H NMR (400 MHz, DMSO-d₆): δ 12.02 (s, 1H), 8.36 (d, J=5.7 Hz, 1H), 8.27 (s, 1H), 8.26 (s, 1H), 7.98 (s, 1H), 7.96 (d, J=0.7 Hz, 1H), 7.18 (d, J=2.4 Hz, 1H), 6.64 (dd, J=5.7, 2.5 Hz, 1H), 3.84 (s, 3H), 2.19 (s, 3H), 1.26 (s, 9H); MS (ESI) m/z: 406.2 (M+H⁺).

Example 32

A suspension of Example A8 (0.250 g, 0.628 mmol), cyclopropane carboxamide (0.100 g, 1.175 mmol), Cs₂CO₃ (0.400 g, 1.228 mmol) and X-Phos (0.012 g, 0.025 mmol) in dioxane (20 mL) was purged with argon for 5 minutes. To the reaction mixture was added Pd₂(dba)₃ (0.012 g, 0.013 mmol) and the mixture wass heated in a reclosable sealed tube (100 mL) at 110° C. for 8 h. The solids from the reaction mixture was filtered and washed with DCM and THF. The filtrate was evaporated and the residue subjected to chromatography using (0-100% EtOAc/DCM) to provide N-(4-((6-(3-(4-fluorophenyl)-5-oxo-4,5-dihydro-1H-1,2,4-triazol-1-yl)-2-methylpyridin-3-yl)oxy)pyridin-2-yl)cyclopropanecarboxamide (0.072 g, 24%) as a white solid. ¹H NMR (400 MHz, DMSO-d₆): δ 12.73 (s, 1H), 10.89 (s, 1H), 8.21 (d, J=5.7 Hz, 1H), 7.98-7.93 (m, 3H), 7.75 (d, J=8.8 Hz, 1H), 7.59 (d, J=2.4 Hz, 1H), 7.40 (t, J=8.8 Hz, 2H), 6.71 (dd, J=5.7, 2.4 Hz, 1H), 2.33 (s, 3H), 1.95 (t, J=6.1 Hz, 1H), 0.75 (d, J=6.2 Hz, 4H), MS (ESI) m/z: 447.2 (M+H⁺).

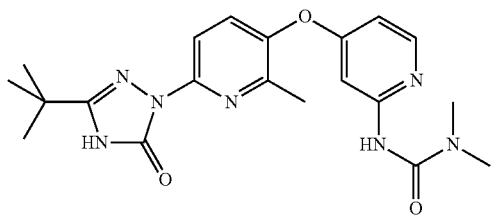 [SMILES: Cc1nc(-n2nc(C(C)(C)C)[nH]c2=O)ccc1Oc1ccnc(NC(=O)N(C)C)c1]

Example 30

A suspension of Example A3 (0.250 g, 0.695 mmol), N,N-dimethyl urea (0.100 g, 1.135 mmol), Cs₂CO₃ (0.500 g, 1.535 mmol) and Xantphos (0.016 g, 0.028 mmol) in dioxane (20 mL) was purged with argon for 5 minutes. Pd₂(dba)₃ (0.025 g, 0.028 mmol) was added and the reaction mixture was heated in a reclosable sealed tube (50 mL) at 100° C. The solids from the reaction mixture was filtered and washed with DCM and THF. The filtrate was concentrated and the residue purified by silica gel chromatography (0-100% THF/DCM) to provide 3-(4-((6-(3-(tert-butyl)-5-oxo-4,5-dihydro-1H-1,2,4-triazol-1-yl)-2-methylpyridin-3-yl)oxy)pyridin-2-yl)-1,1-dimethylurea (0.090 g, 31% yield) as white solid. ¹H NMR (400 MHz, DMSO-d₆): δ 11.98 (s, 1H), 8.92 (s, 1H), 8.11 (d, J=5.7 Hz, 1H), 7.84 (d, J=8.7 Hz, 1H), 7.67 (d, J=8.8 Hz, 1H), 7.30 (d, J=2.4 Hz, 1H), 6.58 (dd, J=5.7, 2.4 Hz, 1H), 2.87 (s, 6H), 2.30 (s, 3H), 1.27 (s, 9H); MS (ESI) m/z: 412.2 (M+H⁺).

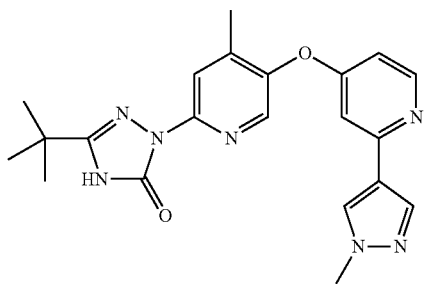 [SMILES: Cc1cc(-n2nc(C(C)(C)C)[nH]c2=O)ncc1Oc1ccnc(-c2cnn(C)c2)c1]

Example 31

Example C1 (0.10 g, 0.71 mmol), copper(I) iodide (0.022 g, 0.116 mmol), and K₂CO₃ (0.44 g, 3.2 mmol) were combined in DMF (3 mL) under argon. Example A10 (0.25 g, 0.64 mmol) and N,N-dimethylethane-1,2-diamine (0.010 g, 0.12 mmol) were added sequentially and the reaction mixture was stirred at 100° C. for 18 h. Sat. NH₄Cl (aq) (10 mL) was added and the resultant suspension was extracted with EtOAc (4×20 mL). The combined organics were dried (MgSO₄) and con-

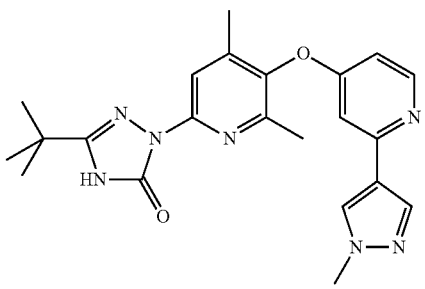 [SMILES: Cc1cc(-n2nc(C(C)(C)C)[nH]c2=O)nc(C)c1Oc1ccnc(-c2cnn(C)c2)c1]

Example 33

A solution of concentrated H₂SO₄ (9 mL) was cooled to 0° C. and the temperature was carefully maintained as 30% H₂O₂ (6.1 mL, 60 mmol) was added over 30 min and 5-bromo-4,6-dimethylpyridin-2-amine (2.0 g, 9.95 mmol) in sulphuric acid (6 mL) was added over 2 h. The solution was allowed to warm to RT and stirred for 1 h. The mixture was poured onto ice (200 g), and the resultant suspension was stirred as it warmed to RT. The solids were collected by filtration, washed with water (3×50 mL), and subjected to high vacuum for 5 h to afford 3-bromo-2,4-dimethyl-6-nitropyridine (2.2 g, 96%) as a yellow solid. $^1$H NMR (400 MHz, DMSO-$d_6$): δ 8.20 (s, 1H), 2.67 (s, 3H), 2.52 (s, 3H); MS (ESI) m/z: 231.0 (M+H$^+$).

3-Bromo-2,4-dimethyl-6-nitropyridine (2.2 g, 9.5 mmol) and 2-chloro-4-hydroxypyridine (2.5 g, 19 mmol) were combined in DMA (10 mL) and the solution was sonicated and sparged with Ar for 10 min. K$_2$CO$_3$ (4.0 g, 29 mmol) was added and the reaction mixture was stirred at 100° C. for 12 h. The reaction mixture was poured into water (200 mL) and the precipitated solids were isolated by filtration. The solids were washed with ½ sat. K$_2$CO$_3$ (aq) (3×50 mL) and water (3×50 mL) and dried under high vacuum for 5 h. The crude product was purified by silica gel chromatography (EtOAc/hexanes) to afford 3-((2-chloropyridin-4-yl)oxy)-2,4-dimethyl-6-nitropyridine (0.50 g, 19%) as a brown solid. $^1$H NMR (400 MHz, DMSO-$d_6$): δ 8.33-8.30 (m, 2H), 7.15 (d, J=2.3 Hz, 1H), 7.01 (dd, J=5.8, 2.3 Hz, 1H), 2.33 (s, 3H), 2.23 (s, 3H); MS (ESI) m/z: 280.0 (M+H$^+$).

3((2-Chloropyridin-4-yl)oxy)-2,4-dimethyl-6-nitropyridine (0.50 g, 1.8 mmol), 1-methyl-4-(4,4,5,5-tetramethyl-1,3,2-dioxaborolan-2-yl)-1H-pyrazole (0.48 g, 2.3 mmol), and K$_2$CO$_3$ (0.37 g, 2.7 mmol) were suspended in dioxane (6 mL) and water (1.2 mL) and sonicated and sparged with Ar for 10 min. Pd(PPh$_3$)$_4$ (0.10 g, 0.089 mmol) was added and the reaction mixture was stirred at 80° C. for 12 h. The mixture was diluted with water (20 mL) and extracted with EtOAc (4×25 mL). The combined organics were dried and concentrated in vacuo. The residue was purified by silica gel chromatography (MeOH/DCM) to afford 2,4-dimethyl-3-((2-(1-methyl-1H-pyrazol-4-yl)pyridin-4-yl)oxy)-6-nitropyridine (0.56 g, 96%) as a brown oil. MS (ESI) m/z: 326.1 (M+H$^+$).

2,4-Dimethyl-3-((2-(1-methyl-1H-pyrazol-4-yl)pyridin-4-yl)oxy)-6-nitropyridine (0.56 g, 1.8 mmol) and NH$_4$Cl (2.76 g, 51.6 mmol) were combined in a solution of MeOH (8.6 mL) and THF (8.6 mL) and cooled to 0° C. Zinc powder (1.13 g, 17.2 mmol) was added portion-wise over 30 min and the reaction mixture was allowed to warm to RT and stirred vigorously for 12 h. EtOAc (100 mL) was added and the resultant suspension was filtered through a pad of diatomaceous earth. The filter cake was washed with EtOAc (3×10 mL) and the combined filtrates were concentrated in vacuo. The residue was purified by silica gel chromatography (MeOH/DCM) to afford 4,6-dimethyl-5-((2-(1-methyl-1H-pyrazol-4-yl)pyridin-4-yl)oxy)pyridin-2-amine (0.41 g, 81%) as a light red solid. MS (ESI) m/z: 296.1 (M+H$^+$).

4,6-Dimethyl-5-((2-(1-methyl-1H-pyrazol-4-yl)pyridin-4-yl)oxy)pyridin-2-amine (0.41 g, 1.4 mmol), KI (2.30 g, 13.9 mmol), and diiodomethane (4 mL, 49.6 mmol) were combined and stirred at RT. The suspension was treated with tert-butylnitrite (1.0 mL, 8.3 mmol) and the reaction mixture was stirred at RT for 12 h. The mixture was diluted with MeCN (10 mL), additional tert-butylnitrite (1.0 mL, 8.3 mmol) was added and stirring was continued at RT for 24 h. The reaction mixture was partitioned between EtOAc (120 mL) and sat. NaHCO$_3$ (aq) (20 mL). The aqueous phase was collected and the organic phase was washed with sat. NaHCO$_3$ (aq) (2×20 mL), 10% Na$_2$S$_2$O$_3$(aq) (2×20 mL), and brine (2×20 mL). The combined aqueous washes were back-extracted with EtOAc (2×20 mL) and the combined organics were dried (MgSO$_4$) and concentrated in vacuo. The residue was purified by silica gel chromatography (EtOAc/DCM) to afford 6-iodo-2,4-dimethyl-3-((2-(1-methyl-1H-pyrazol-4-yl)pyridin-4-yl)oxy)pyridine (0.24 g, 43%) as an off white solid that was used in the next step without further purification. MS (ESI) m/z: 407.0 (M+H$^+$).

Example C1 (0.10 g, 0.71 mmol), copper(I) iodide (0.020 g, 0.11 mmol), and K$_2$CO$_3$ (0.41 g, 3.0 mmol) were suspended in DMF (3 mL) under an atmosphere of Ar. 6-Iodo-2,4-dimethyl-3-((2-(1-methyl-1H-pyrazol-4-yl)pyridin-4-yl)oxy)pyridine (0.24 g, 0.59 mmol) and N,N-dimethylethane-1,2-diamine (0.010 g, 0.11 mmol) were added sequentially and the reaction mixture was stirred at 100° C. for 18 h. Sat. NH$_4$Cl (aq) (10 mL) was added and the resultant suspension was extracted with EtOAc (4×20 mL). The combined organics were dried (MgSO$_4$) and concentrated in vacuo. The residue was purified by silica gel chromatography (MeOH/DCM) to afford 3-(tert-butyl)-1-(4,6-dimethyl-5-((2-(1-methyl-1H-pyrazol-4-yl)pyridin-4-yl)oxy)pyridin-2-yl)-1H-1,2,4-triazol-5(4H)-one (0.114 g, 48.0%) as a white solid. $^1$H NMR (400 MHz, DMSO-$d_6$): δ 11.99 (s, 1H), 8.34 (d, J=5.7 Hz, 1H), 8.26 (s, 1H), 7.96 (s, 1H), 7.79 (s, 1H), 7.13 (d, J=2.4 Hz, 1H), 6.55 (dd, J=5.7, 2.4 Hz, 1H), 3.84 (s, 3H), 2.25 (s, 3H), 2.13 (s, 3H), 1.27 (s, 9H); MS (ESI) m/z: 420.2 (M+H$^+$).

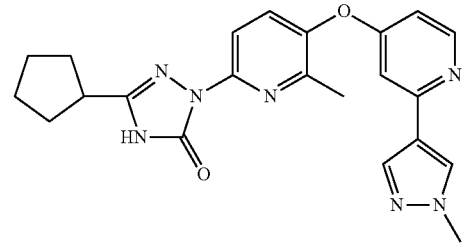 [SMILES: Cc1nc(-n2nc(C3CCCC3)[nH]c2=O)ccc1Oc1ccnc(-c2cnn(C)c2)c1]

Example 34

A suspension of Example A11 (0.340 g, 0.91 mmol), 1-methyl-4-(4,4,5,5-tetramethyl-1,3,2-dioxaborolan-2-yl)-1H-pyrazole (0.250 g, 1.202 mmol), Cs$_2$CO$_3$ (0.680 g, 2.087 mmol) and Pd(PPh$_3$)$_4$ (0.050 g, 0.043 mmol) in MeCN (20 mL) was heated at 100° C. under argon for 4 hours. The solvent from the reaction mixture was completely evaporated and the residue was partitioned between DCM (50 mL) and water (50 mL). The organic layer was separated and the aqueous layer saturated with solid sodium chloride and extracted with DCM (2×20 mL). The combined organic layer was dried and concentrated to a small volume and subjected to chromatography using (0-20% MeOH/DCM) to provide 3-cyclopentyl-1-(6-methyl-5-((2-(1-methyl-1H-pyrazol-4-yl)pyridin-4-yl)oxy)pyridin-2-yl)-1H-1,2,4-triazol-5(4H)-one (0.191 g, 49.5%) as a white solid. $^1$H NMR (400 MHz, DMSO-$d_6$): δ 11.90 (s, 1H), 8.36 (d, J=5.7 Hz, 1H), 8.26 (s, 1H), 7.96 (s, 1H), 7.86 (d, J=8.8 Hz, 1H), 7.68 (d, J=8.8 Hz, 1H), 7.19 (d, J=2.4 Hz, 1H), 6.64 (dd, J=5.7, 2.4 Hz, 1H), 3.84 (s, 3H), 2.96 (m, 1H), 2.32 (s, 3H), 1.94 (t, J=7.8 Hz, 2H), 1.74 (m, 4H), 1.61 (m, 2H); MS (ESI) m/z: 418.2 (M+H$^+$).

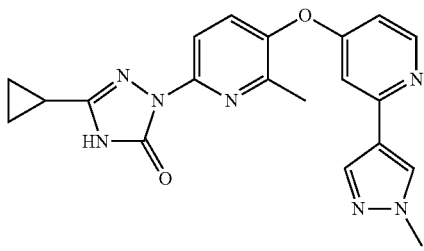 [SMILES: Cc1nc(-n2nc(C3CC3)[nH]c2=O)ccc1Oc1ccnc(-c2cnn(C)c2)c1]

Example 35

To a suspension of semicarbazide hydrochloride (5.00 g, 44.8 mmol) in DCM (100 mL) was added triethylamine (10.00 g, 99 mmol) and the mixture was stirred at −10° C. for 30 min. Cyclopropane carbonylchloride (5.00 g, 47.8 mmol) was added at the same temp and the mixture was stirred to RT over night. The solvent from the reaction mixture was completely removed and the residue stirred in MeCN (200 mL) for 1 h. The solids were collected by filtration, washed and dried. The solid was transferred to a RB flask and treated with sodium hydroxide (7.00 g, 175 mmol) and water (20 mL). The resulting reaction mixture was heated at 100° C. for 2 hours. The reaction mixture was cooled and acidified with conc. HCl. The solids were collected by filtration, washed and dried to provide 3-cyclopropyl-1H-1,2,4-triazol-5(4H)-one (1.82 g, 30.4% yield) as white solid. $^1$H NMR (400 MHz, DMSO-$d_6$): δ11.03 (br s, 2H), 1.67 (m, 1H), 0.82 (m, 2H), 0.73 (m, 2H); MS (ESI) m/z: 126.1 (M+H$^+$).

A suspension of 3-cyclopropyl-1H-1,2,4-triazol-5(4H)-one (0.600 g, 4.80 mmol), Example A1 (1.00 g, 2.89 mmol), copper iodide (0.050 g, 0.263 mmol), Cs$_2$CO$_3$ (2.00 g, 6.14 mmol) and N1,N2-dimethylethane-1,2-diamine (0.050 g, 0.567 mmol) in MeCN (20 mL) was heated at 100° C. under argon for 14 hours. The solvent from the reaction mixture was completely evaporated and the residue was partitioned between DCM (50 mL) and water (50 mL). The organic layer was separated and the aqueous layer saturated with solid sodium chloride and extracted with DCM (2×20 mL). The combined organic layer was dried, concentrated to a small volume and purified by silica gel chromatography (0-100% EtOAc/DCM) to provide 1-(5-((2-chloropyridin-4-yl)oxy)-6-methylpyridin-2-yl)-3-cyclopropyl-1H-1,2,4-triazol-5(4H)-one (0.288 g, 29%) as a white solid. $^1$H NMR (400 MHz, DMSO-$d_6$): δ 11.81 (s, 1H), 8.29 (d, J=5.8 Hz, 1H), 7.87 (d, J=8.8 Hz, 1H), 7.72 (d, J=8.8 Hz, 1H), 7.06 (d, J=2.3 Hz, 1H), 6.95 (dd, J=5.8, 2.3 Hz, 1H), 2.29 (s, 3H), 1.87 (m, 1H), 0.95 (m, 4H); MS (ESI) m/z: 344.1 (M+1-1').

A suspension of 1-(5-((2-chloropyridin-4-yl)oxy)-6-methylpyridin-2-yl)-3-cyclopropyl-1H-1,2,4-triazol-5(4H)-one (0.285 g, 0.829 mmol), 1-methyl-4-(4,4,5,5-tetramethyl-1,3,2-dioxaborolan-2-yl)-1H-pyrazole (0.250 g, 1.202 mmol), Cs$_2$CO$_3$ (0.600 g, 1.842 mmol) and Pd(PPh$_3$)$_4$ (0.050 g, 0.043 mmol) in MeCN (20 mL) was heated at 100° C. under argon for 4 hours. The solvent from the reaction mixture was completely evaporated and the residue was partitioned between DCM (50 mL) and water (50 mL). The organic layer was separated and the aqueous layer saturated with solid sodium chloride and extracted with DCM (2×20 mL). The combined organics were dried, concentrated, and purified by silica gel chromatography (0-20% MeOH/DCM) to provide 3-cyclopropyl-1-(6-methyl-5-((2-(1-methyl-1H-pyrazol-4-yl)pyridin-4-yl)oxy)pyridin-2-yl)-1H-1,2,4-triazol-5(4H)-one (0.228 g, 66%) as a white solid. $^1$H NMR (400 MHz, dmso): δ 11.80 (s, 1H), 8.36 (d, J=5.7 Hz, 1H), 8.26 (s, 1H), 7.96 (s, 1H), 7.86 (d, J=8.8 Hz, 1H), 7.68 (d, J=8.8 Hz, 1H), 7.20 (d, J=2.4 Hz, 1H), 6.63 (dd, J=5.7, 2.4 Hz, 1H), 3.84 (s, 3H), 2.32 (s, 3H), 1.87 (tt, J=8.4, 5.1 Hz, 1H), 0.95 (m, 4H); MS (ESI) m/z: 390.2 (M+H$^+$).

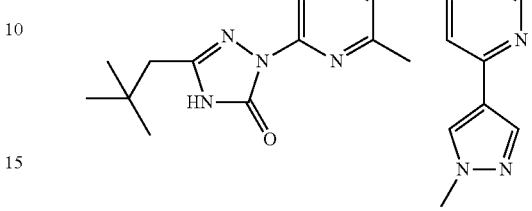

Example 36

Semicarbazide hydrochloride (1.50 g, 13.6 mmol) was dissolved in water (15 mL). NaHCO$_3$ (2.40 g, 28.6 mmol) was slowly added to the solution over 30 min at RT followed by the addition of 3,3-dimethylbutyryl chloride (2 g, 14.86 mmol). The mixture was stirred at RT for 12 h followed by the addition of solid NaOH (1.08 g, 27 mmol). The reaction mixture was stirred at 100° C. for 3 h, allowed to cool to RT and stirred for an additional 12 h. The reaction mixture was neutralized by the drop-wise addition of concentrated HCl. The solids were collected by filtration, washed with water, and dried in vacuo to afford 3-neopentyl-1H-1,2,4-triazol-5(4H)-one (0.65 g, 31%) as a white solid. $^1$H NMR (400 MHz, DMSO-$d_6$): δ 11.12 (s, 1H), 11.10 (s, 1H), 2.20 (s, 2H), 0.90 (s, 9H).

Example A1 (0.50 g, 1.44 mmol), 3-neopentyl-1H-1,2,4-triazol-5(4H)-one (0.20 g, 1.29 mmol), and K$_2$CO$_3$ (1.00 g, 7.24 mmol) were suspended in DMF (4.5 mL). The mixture was sonicated and sparged with Ar for 10 min followed by sequential addition of copper(I) iodide (0.05 g, 0.26 mmol) and N,N-dimethylethane-1,2-diamine (0.02 g, 0.26 mmol). The reaction mixture was stirred at 100° C. for 12 h, allowed to cool to RT, and subsequently diluted with sat. NH$_4$Cl (aq.) (15 mL), and extracted with EtOAc (5×20 mL). The combined organics were dried (MgSO$_4$) and concentrated in vacuo. The resultant yellow oil was triturated with MeCN (3 mL) and sonicated to afford a pale yellow solid that was isolated by filtration and dried in vacuo to afford 1-(5-((2-chloropyridin-4-yl)oxy)-6-methylpyridin-2-yl)-3-neopentyl-1H-1,2,4-triazol-5(4H)-one (0.37 g, 77%) as a pale yellow solid. $^1$H NMR (400 MHz, DMSO-$d_6$): δ 11.85 (s, 1H), 8.29 (d, J=5.8 Hz, 1H), 7.90 (d, J=8.8 Hz, 1H), 7.74 (d, J=8.8 Hz, 1H), 7.08 (d, J=2.3 Hz, 1H), 6.97 (dd, J=5.8, 2.3 Hz, 1H), 2.37 (s, 2H), 2.30 (s, 3H), 0.97 (s, 9H); MS (ESI) m/z: 374.1 (M+H$^+$).

1-(5-((2-Chloropyridin-4-yl)oxy)-6-methylpyridin-2-yl)-3-neopentyl-1H-1,2,4-triazol-5(4H)-one (0.15 g, 0.40 mmol), 1-methyl-4-(4,4,5,5-tetramethyl-1,3,2-dioxaborolan-2-yl)-1H-pyrazole (0.11 g, 0.52 mmol), and K$_2$CO$_3$ (0.14 g, 1.04 mmol) were suspended in a solution of dioxane (2.0 mL) and water (0.40 mL). The suspension was sonicated and sparged with Ar for 10 min. Pd(PPh$_3$)$_4$ (0.05 g, 0.04 mmol) was added and the reaction mixture was stirred at 85° C. for 12 h, allowed to cool to RT, diluted with water (5 mL), and extracted with EtOAc (5×10 mL). The combined organics were dried (MgSO$_4$) and concentrated in vacuo. The residue was purified by silica gel chromatography (MeOH/DCM) to afford 1-(6-methyl-5-((2-(1-methyl-1H-pyrazol-4-yl)pyridin-4-yl)oxy)pyridin-2-yl)-3-neopentyl-1H-1,2,4-triazol-5(4H)-one (0.124 g, 69%) as a white solid. $^1$H NMR (400 MHz, DMSO-d$_6$): δ 11.83 (s, 1H), 8.36 (d, J=5.7 Hz, 1H), 8.26 (s, 1H), 7.97 (s, 1H), 7.89 (d, J=8.8 Hz, 1H), 7.69 (d, J=8.8 Hz, 1H), 7.21 (d, J=2.4 Hz, 1H), 6.65 (dd, J=5.7, 2.4 Hz, 1H), 3.84 (s, 3H), 2.38 (s, 2H), 2.33 (s, 3H), 0.98 (s, 9H); MS (ESI) m/z: 420.2 (M+H$^+$).

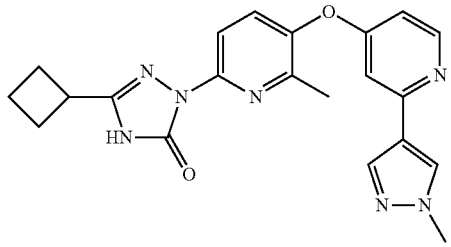 [SMILES: Cc1nc(-n2nc(C3CCC3)[nH]c2=O)ccc1Oc1ccnc(-c2cnn(C)c2)c1]

Example 37

To a 0° C. solution of cyclobutane carboxylic acid (7.50 g, 74.9 mmol) in DCM (100 mL) was added oxalyl chloride (12.00 g, 95 mmol) followed by catalytic amount of DMF. The resultant mixture was stirred at RT for 1 h. The solvent from the reaction mixture was completely evaporated to a light coloured viscous mass. In a different RB flask, a suspension of semicarbazide hydrochloride (9.00 g, 81 mmol) in DCM (100 mL) was treated with triethylamine (18.00 g, 178 mmol) and stirred at −10° C. for 30 minutes. To the reaction mixture was added the acid chloride dissolved in DCM (20 mL) at the same temp and the resultant mixture was stirred at RT over night. The solvent from the reaction mixture was completely removed and the residue was stirred in MeCN (100 mL) for 1 h. The solids were collected by filtration, washed and dried. The solid was transferred to a RB flask and was treated with sodium hydroxide (7.50 g, 188 mmol) and water (20 mL). The resulting reaction mixture was heated at 100° C. for 3 h, cooled to RT, and acidified with conc. sulfuric acid. The solids were collected, washed sparingly with cold water, and dried to provide 3-cyclobutyl-1H-1,2,4-triazol-5(4H)-one, (6.40 g, 61.4% yield) as white solid. $^1$H NMR (400 MHz, DMSO-d$_6$): δ 11.27 (s, 1H), 11.10 (s, 1H), 2.15 (m, 7H); MS (ESI) m/z: 140.1 (M+H$^+$).

A suspension of 3-cyclobutyl-1H-1,2,4-triazol-5(4H)-one (0.800 g, 5.75 mmol), Example A1 (1.000 g, 2.89 mmol), copper iodide (0.050 g, 0.263 mmol), Cs$_2$CO$_3$ (2.000 g, 6.14 mmol) and N1,N2-dimethylethane-1,2-diamine (0.050 g, 0.567 mmol) in acetonitrile (20 mL) was heated at 100° C. under argon for 4 h. The solvent was completely evaporated and the residue was stirred in water. The solids were collected, washed and dried to provide 1-(5-((2-chloropyridin-4-yl)oxy)-6-methylpyridin-2-yl)-3-cyclobutyl-1H-1,2,4-triazol-5(4H)-one (0.820 g, 79%) as a yellow solid. $^1$H NMR (400 MHz, DMSO-d$_6$): δ 8.48 (d, J=9.0 Hz, 1H), 8.26 (d, J=5.7 Hz, 1H), 7.77 (d, J=9.0 Hz, 1H), 6.95-6.89 (m, 2H), 3.10 (m, 1H), 2.20 (m, 4H), 2.03 (s, 3H), 1.70 (m, 2H); MS (ESI) m/z: 358.1 (M+H$^+$.

A suspension of 1-(5-((2-chloropyridin-4-yl)oxy)-6-methylpyridin-2-yl)-3-cyclobutyl-1H-1,2,4-triazol-5(4H)-one (0.300 g, 0.838 mmol), 1-methyl-4-(4,4,5,5-tetramethyl-1,3,2-dioxaborolan-2-yl)-1H-pyrazole (0.250 g, 1.202 mmol), Cs$_2$CO$_3$ (0.600 g, 1.842 mmol) and Pd(PPh$_3$)$_4$ (0.050 g, 0.043 mmol) in acetonitrile (20 mL) was heated at 100° C. under argon for 2 h. The solvent from the reaction mixture was completely evaporated and the residue partitioned between DCM (50 mL) and water (50 mL). The organic layer was separated and the aqueous layer saturated with solid sodium chloride and extracted with DCM (2×20 mL). The combined organics were dried, concentrated, subjected to silica gel chromatography (0-100% THF/EtOAc) to provide 3-cyclobutyl-1-(6-methyl-5-((2-(1-methyl-1H-pyrazol-4-yl)pyridin-4-yl)oxy)pyridin-2-yl)-1H-1,2,4-triazol-5(4H)-one (0.055 g, 15%) as a white solid. $^1$H NMR (400 MHz, DMSO-d$_6$): δ 11.97 (s, 1H), 8.37 (d, J=5.7 Hz, 1H), 8.26 (s, 1H), 7.96 (s, 1H), 7.87 (d, J=8.8 Hz, 1H), 7.69 (d, J=8.8 Hz, 1H), 7.20 (d, J=2.4 Hz, 1H), 6.64 (dd, J=5.7, 2.4 Hz, 1H), 3.84 (s, 3H), 3.44 (m, 1H), 2.33 (s, 3H), 2.26 (m, 4H), 2.04 (m, 1H), 1.90 (m, 1H); MS (ESI) m/z: 404.2 (M+H$^+$).

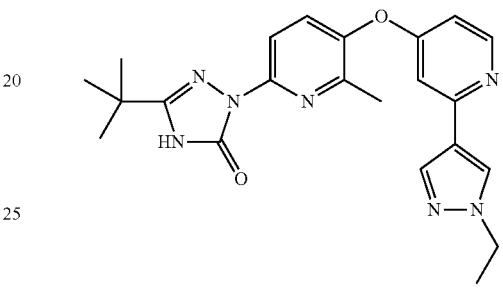

Example 38

Example A3 (80 mg, 0.22 mmol), 1-ethyl-4-(4,4,5,5-tetramethyl-1,3,2-dioxaborolan-2-yl)-1H-pyrazole (55 mg, 0.24 mmol), and K$_2$CO$_3$ (90 g, 0.66 mmol) were combined in the mixture of dioxane/water (4:1, 5 mL). The mixture was sparged with Ar and then Pd(PPh$_3$)$_4$ (26 mg, 0.022 mmol) was added. The mixture was sparge with Ar again and then heated at 90° C. overnight. The reaction mixture was diluted with saturated aqueous NaHCO$_3$ and then the solution was extracted with EtOAc (3×). The combined organics were dried (Na$_2$SO$_4$), filtered and concentrated to dryness. The material was purified via silica gel chromatography (MeOH/DCM) to obtain 3-(tert-butyl)-1-(5-((2-(1-ethyl-1H-pyrazol-4-yl)pyridin-4-yl)oxy)-6-methylpyridin-2-yl)-1H-1,2,4-triazol-5(4H)-one (35 mg, 36.6%). $^1$H NMR (400 MHz, DMSO-d$_6$): δ 11.99 (s, 1H), 8.37 (d, J=5.7 Hz, 1H), 8.32 (s, 1H), 7.98 (s, 1H), 7.86 (d, J=8.8 Hz, 1H), 7.69 (d, J=8.8 Hz, 1H), 7.20 (d, J=2.4 Hz, 1H), 6.65 (dd, J=5.7, 2.4 Hz, 1H), 4.13 (q, J=7.3 Hz, 2H), 2.34 (s, 3H), 1.37 (t, J=7.3 Hz, 3H), 1.28 (s, 9H); MS (ESI) m/z: 420.2 (M+H$^+$).

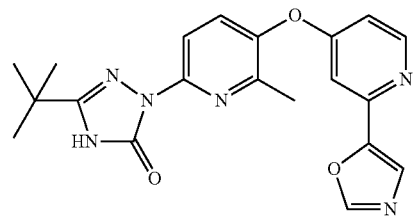 [SMILES: Cc1nc(-n2nc(C(C)(C)C)[nH]c2=O)ccc1Oc1ccnc(-c2cnco2)c1]

Example 39

Example A3 (0.14 g, 0.39 mmol), 5-(4,4,5,5-tetramethyl-1,3,2-dioxaborolan-2-yl)oxazole (0.10 g, 0.51 mmol), and K$_2$CO$_3$ (0.14 g, 1.04 mmol) were suspended in a solution of dioxane (2.5 mL) and water (0.50 mL). The suspension was sonicated and sparged with Ar for 10 min. Pd(PPh$_3$)$_4$ (0.05 g, 0.04 mmol) was added and the reaction mixture was stirred at 85° C. for 12 h, allowed to cool to RT, diluted with sat. NH$_4$Cl (aq.) (5 mL), and extracted with EtOAc (4×5 mL). The combined organics were dried (Na$_2$SO$_4$) and concentrated in vacuo. The residue was purified by silica gel chromatography (MeOH/DCM) to afford 3-(tert-butyl)-1-(6-methyl-5-((2-(oxazol-5-yl)pyridin-4-yl)oxy)pyridin-2-yl)-1H-1,2,4-triazol-5(4H)-one (0.025 g, 15.6%) as an off white solid. $^1$H NMR (400 MHz, DMSO-d$_6$): δ 11.99 (s, 1H), 8.51 (d, J=5.7 Hz, 1H), 8.49 (s, 1H), 7.87 (d, J=8.8 Hz, 1H), 7.80 (s, 1H), 7.76 (d, J=8.8 Hz, 1H), 7.21 (d, J=2.5 Hz, 1H), 6.91 (dd, J=5.7, 2.4 Hz, 1H), 2.33 (s, 3H), 1.27 (s, 9H); MS (ESI) m/z: 393.2 (M+H$^+$).

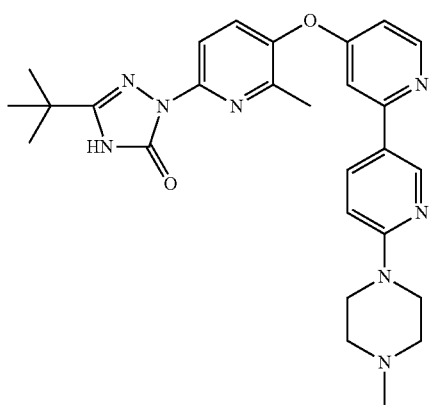 [SMILES: Cc1nc(-n2nc(C(C)(C)C)[nH]c2=O)ccc1Oc1ccnc(-c2ccc(N3CCN(C)CC3)nc2)c1]

Example 40

In a sealed tube, Pd(PPh$_3$)$_4$ (0.016 g, 0.014 mmol), K$_2$CO$_3$ (0.115 g, 0.834 mmol), Example A3 (0.100 g, 0.278 mmol), and 2-(4-methylpiperazino)pyridine-5-boronic acid pinacol ester (0.126 g, 0.417 mmol) were suspended in dioxane (6 mL) and water (1.5 mL). The mixture was degassed with Ar and heated at 90° C. overnight. The reaction mixture was partitioned between EtOAc and 1N NaOH and extracted with EtOAc (2×). The EtOAc extracts were combined and washed with brine. The aqueous extracts were combined and back-extracted with DCM (3×). The DCM extracts were combined with the EtOAc extracts, dried, and evaporated. The crude product was purified by silica gel preparatory TLC (DCM/MeOH (10% NEt$_3$)) to give the desired product, which was dissolved in acetonitrile/water, frozen and lyophilized to yield 3-(tert-butyl)-1-(6-methyl-5-((6'-(4-methylpiperazin-1-yl)-[2,3'-bipyridin]-4-yl)oxy)pyridin-2-yl)-1H-1,2,4-triazol-5(4H)-one (49 mg, 35.2%). $^1$H NMR (400 MHz, DMSO-d$_6$): δ 11.99 (s, 1H), 8.85 (d, J=2.5 Hz, 1H), 8.49 (d, J=5.7 Hz, 1H), 8.27 (dd, J=9.0, 2.5 Hz, 1H), 7.86 (d, J=8.8 Hz, 1H), 7.71 (d, J=8.8 Hz, 1H), 7.56-7.54 (m, 1H), 7.03 (d, J=9.0 Hz, 1H), 6.77-6.75 (m, 1H), 4.51-4.49 (m, 2H), 3.56-3.46 (m, 2H), 3.22-3.20 (m, 2H), 3.08-3.05 (m, 2H), 2.81 (d, J=4.5 Hz, 3H), 2.35 (s, 3H), 1.27 (s, 9H); MS (ESI) m/z: 501.3 (M+H$^+$).

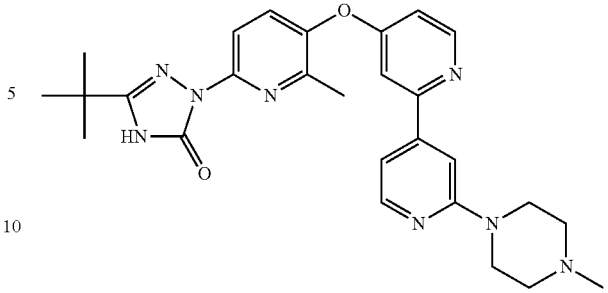

Example 41

In a sealed tube, Pd(PPh$_3$)$_4$ (0.016 g, 0.014 mmol), K$_2$CO$_3$ (0.115 g, 0.834 mmol), Example A3 (0.100 g, 0.278 mmol), and 2-(4-methylpiperazino)pyridine-4-boronic acid pinacol ester (0.126 g, 0.417 mmol) were suspended in dioxane (6 mL) and water (1.5 mL). The mixture was degassed with Ar and heated at 90° C. for 20 h. The reaction mixture was partitioned between EtOAc and 1N NaOH and extracted with EtOAc (2×). The EtOAc extracts were combined and washed with brine. The aqueous extracts were combined and back-extracted with DCM (3×). The DCM extracts were combined with the EtOAc extracts, dried and evaporated. The crude product was purified by silica gel preparatory TLC [DCM/MeOH (10% NEt$_3$)] to give the desired product which was dissolved in acetonitrile/water, frozen and lyophilized to yield 3-(tert-butyl)-1-(6-methyl-5-((2'-(4-methylpiperazin-1-yl)-[2,4'-bipyridin]-4-yl)oxy)pyridin-2-yl)-1H-1,2,4-triazol-5(4H)-one (45 mg, 32.3%). $^1$H NMR (400 MHz, DMSO-d$_6$): δ 11.99 (s, 1H), 8.57 (d, J=5.7 Hz, 1H), 8.25 (d, J=5.3 Hz, 1H), 7.87 (d, J=8.8 Hz, 1H), 7.81 (d, J=2.3 Hz, 1H), 7.72 (d, J=8.8 Hz, 1H), 7.58 (s, 1H), 7.40-7.39 (m, 1H), 6.85-6.84 (m, 1H), 4.52-4.49 (m, 2H), 3.42 (m, 2H), 3.18-3.17 (m, 2H), 3.13-3.04 (m, 2H), 2.83 (d, J=4.6 Hz, 3H), 2.35 (s, 3H), 1.27 (s, 9H); MS (ESI) m/z: 501.3 (M+H$^+$).

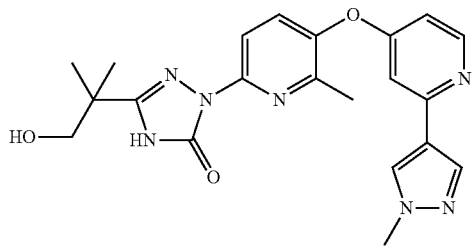 [SMILES: Cc1nc(-n2nc(C(C)(C)CO)[nH]c2=O)ccc1Oc1ccnc(-c2cnn(C)c2)c1]

Example 42

3-(Benzyloxy)-2,2-dimethylpropanoic acid (1.00 g, 4.80 mmol) was dissolved in DCM (10 mL) at RT. Oxalyl chloride (0.70 mL, 8.00 mmol) and DMF (0.10 mL, 1.29 mmol) were added sequentially and the reaction mixture was stirred at RT for 2 h. In a separate flask, semicarbazide hydrochloride (0.8 g, 7.24 mmol) and NaOH (0.80 g, 20.0 mmol) were dissolved in a solution of dioxane (2.0 mL) and water (10.0 mL). The solution of the acid chloride was added in one portion to the solution of the semicarbazide and the reaction mixture was stirred at RT for 12 h. 2 M NaOH (aq.) (28.0 mL, 56.0 mmol) was then added and the reaction mixture was stirred at 100° C. for 2 h, allowed to cool to RT, and neutralized by the addition of ¾ sat. NH₄Cl (aq.) (75 mL). The resultant homogenous solution was sonicated for 12 h and the resultant precipitated solids were collected by filtration and dried in vacuo to afford 3-(1-(benzyloxy)-2-methylpropan-2-yl)-1H-1,2,4-triazol-5(4H)-one (0.57 g, 48.0%) as a white solid. ¹H NMR (400 MHz, DMSO-d₆): δ 11.22 (s, 1H), 11.09 (s, 1H), 7.34-7.23 (m, 5H), 4.44 (s, 2H), 3.39 (s, 2H), 1.16 (s, 5H).

Example A1 (0.40 g, 1.15 mmol), 3-(1-(benzyloxy)-2-methylpropan-2-yl)-1H-1,2,4-triazol-5(4H)-one (0.29, 1.15 mmol), and K₂CO₃ (1.00 g, 7.24 mmol) were combined in DMF (4.0 mL) and the mixture was sonicated and sparged with Ar for 10 min. Copper(I) iodide (0.04 g, 0.23 mmol) and N,N-dimethylethane-1,2-diamine (0.02 g, 0.23 mmol) were added. The reaction mixture was stirred at 100° C. for 12 h, allowed to cool to RT, and subsequently diluted with ¾ sat. NH₄Cl (aq.) (50 mL) and EtOAc (50 mL). The biphasic solution was mixed vigorously and extracted with EtOAc (2×50 mL)). The combined organics were dried (Na₂SO₄) and concentrated in vacuo to afford 3-(1-(benzyloxy)-2-methylpropan-2-yl)-1-(5-((2-chloropyridin-4-yl)oxy)-6-methylpyridin-2-yl)-1H-1,2,4-triazol-5(4H)-one (0.41 g, 76%) as a pale yellow oil. ¹H NMR (400 MHz, DMSO-d₆): δ 11.96 (s, 1H), 8.29 (d, J=5.8 Hz, 1H), 7.87 (d, J=8.8 Hz, 1H), 7.74 (d, J=8.8 Hz, 1H), 7.29-7.27 (m, 5H), 7.07 (d, J=2.3 Hz, 1H), 6.96 (dd, J=5.8, 2.3 Hz, 1H), 4.49 (s, 2H), 3.49 (s, 2H), 2.31 (s, 3H), 1.26 (s, 6H); MS (ESI) m/z: 466.2 (M+H⁺).

3-(1-(Benzyloxy)-2-methylpropan-2-yl)-1-(5-((2-chloropyridin-4-yl)oxy)-6-methylpyridin-2-yl)-1H-1,2,4-triazol-5(4H)-one (0.41 g, 0.88 mmol), 1-methyl-4-(4,4,5,5-tetramethyl-1,3,2-dioxaborolan-2-yl)-1H-pyrazole (0.24 g, 1.14 mmol), and K₂CO₃ (0.32 g, 2.29 mmol) were suspended in a solution of dioxane (5.0 mL) and water (1.0 mL). The suspension was sonicated and sparged with Ar for 10 min followed by the addition of Pd(PPh₃)₄ (0.10 g, 0.09 mmol). The reaction mixture was stirred at 85° C. for 12 h, allowed to cool to RT, and suspended between sat. NH₄Cl (aq.) (15 mL) and EtOAc (20 mL). The organic phase was collected and the aqueous phase was extracted with EtOAc (3×15 mL). The combined organics were dried (Na₂SO₄) and concentrated in vacuo to afford an orange oil. The residue was purified by silica gel chromatography (MeOH/DCM) to afford 3-(1-(benzyloxy)-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.41 g, 91%) as a viscous, pale yellow oil. ¹H NMR (400 MHz, DMSO-d₆): δ 11.95 (s, 1H), 8.36 (d, J=5.6 Hz, 1H), 8.26 (s, 1H), 7.96 (s, 1H), 7.86 (d, J=8.8 Hz, 1H), 7.69 (d, J=8.8 Hz, 1H), 7.31-7.29 (m, 5H), 7.18 (d, J=2.4 Hz, 1H), 6.66 (dd, J=5.7, 2.4 Hz, 1H), 4.49 (s, 2H), 3.83 (s, 3H), 3.50 (s, 2H), 2.33 (s, 3H), 1.27 (s, 6H); MS (ESI) m/z: 512.3 (M+H⁺).

3-(1-(Benzyloxy)-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.41 g, 0.80 mmol), and palladium(0) on carbon (10% w/w, 0.20 g, 0.19 mmol) were combined in EtOAc (4.0 mL) under an atmosphere of Ar. The reaction flask was depressurized and back-filled with H₂ (g). This process was repeated (2×) and the reaction mixture was stirred under a balloon of H₂ (g) for 12 h. Formic acid (0.5 mL) was added and stirring was continued an additional 12 h at RT. The reaction mixture was transferred to a Parr hydrogenation shaker and reaction was continued under 40 psi H₂ (g) atmosphere. After 5 h, the Pd was removed by filtration through a pad of diatomaceous earth and the filter cake was washed with EtOAc (4×25 mL). The combined filtrates were concentrated in vacuo. The residue was purified by silica gel chromatography (MeOH/DCM) to afford 3-(1-hydroxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.053 g, 15%) as a white solid. ¹H NMR (400 MHz, DMSO-d₆): δ 11.85-11.83 (m, 1H), 8.36 (d, J=5.7 Hz, 1H), 8.26 (s, 1H), 7.96 (s, 1H), 7.86 (d, J=8.8 Hz, 1H), 7.69 (d, J=8.8 Hz, 1H), 7.18 (d, J=2.4 Hz, 1H), 6.65 (dd, J=5.7, 2.4 Hz, 1H), 4.92-4.91 (m, 1H), 3.84 (s, 3H), 3.45-3.43 (m, 2H), 2.33 (s, 3H), 1.20 (s, 6H); MS (ESI) m/z: 422.2 (M+H⁺).

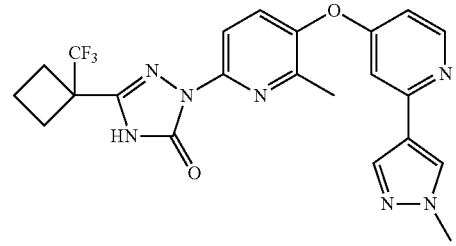 [SMILES: Cc1nc(-n2nc(C3(C(F)(F)F)CCC3)[nH]c2=O)ccc1Oc1ccnc(-c2cnn(C)c2)c1]

Example 43

A suspension of Example C7 (1.00 g, 4.83 mmol), Example A1 (0.500 g, 1.443 mmol), copper iodide (0.050 g, 0.263 mmol), Cs₂CO₃ (1.000 g, 3.07 mmol) and N1,N2-dimethylethane-1,2-diamine (0.050 g, 0.567 mmol) in MeCN (20 mL) was heated at 100° C. under argon for 14 hours. The solvent from the reaction mixture was completely evaporated and the residue partitioned between DCM (50 mL) and water (50 mL). The organic layer was separated and the aqueous layer saturated with solid sodium chloride and extracted with DCM (2×20 mL). The organics were dried, concentrated, and purified by silica gel chromatography (0-100% EtOAc/DCM) to provide 1-(54(2-chloropyridin-4-yl)oxy)-6-methylpyridin-2-yl)-3-(1-(trifluoromethyl)cyclobutyl)-1H-1,2,4-triazol-5(4H)-one (0.240 g, 39% yield) as light greenish solid, suitable for use in the next reaction. MS (ESI) m/z: 426.1 (M+H⁺).

To a suspension of 1-(5((2-chloropyridin-4-yl)oxy)-6-methylpyridin-2-yl)-3-(1-(trifluoromethyl)cyclobutyl)-1H-1,2,4-triazol-5(4H)-one (0.240 g, 0.564 mmol), 1-methyl-4-(4,4,5,5-tetramethyl-1,3,2-dioxaborolan-2-yl)-1H-pyrazole (0.250 g, 1.202 mmol), Cs₂CO₃ (0.500 g, 1.535 mmol) and Pd(PPh₃)₄ (0.030 g, 0.026 mmol) in EtOH (20 mL) was heated at 100° C. The solvent from the reaction mixture was completely evaporated and the residue was partitioned between DCM (30 mL) and water (30 mL). The organic layer was separated and the aqueous layer saturated with solid sodium chloride and extracted with DCM (2×20 mL). The combined organics were dried, concentrated in vacuo, and purified by silica gel chromatography (0-40% THF/EtOAc) to provide 1-(6-methyl-5-((2-(1-methyl-1H-pyrazol-4-yl)pyridin-4-yl)oxy)pyridin-2-yl)-3-(1-(trifluoromethyl)cyclobutyl)-1H-1,2,4-triazol-5(4H)-one (0.013 g, 4.6%) as a white solid. ¹H NMR (400 MHz, DMSO-d₆): δ 12.48 (s, 1H), 8.37 (d, J=5.7 Hz, 1H), 8.26 (s, 1H), 7.97 (s, 1H), 7.91 (d, J=8.8 Hz, 1H), 7.73 (d, J=8.8 Hz, 1H), 7.20 (d, J=2.4 Hz, 1H), 6.67 (dd, J=5.7, 2.4 Hz, 1H), 3.84 (s, 3H), 2.61 (m, 4H), 2.35 (s, 3H), 2.03 (t, J=8.2 Hz, 2H); MS (ESI) m/z: 472.2 (M+H⁺).

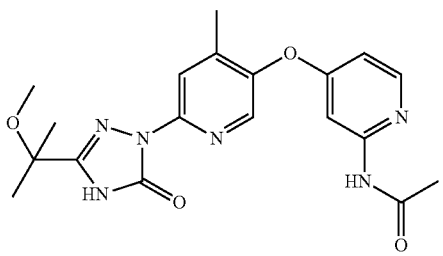 [SMILES: COC(C)(C)c1nn(-c2cc(C)c(Oc3ccnc(NC(C)=O)c3)cn2)c(=O)[nH]1]

Example 44

Example A13 (0.74 g, 2.87 mmol), potassium iodide (4.80 g, 28.9 mmol), and diiodomethane (6.00 mL, 74.4 mmol) were combined at RT. tert-Butylnitrite (2.00 mL, 16.7 mmol) was added dropwise and the reaction mixture was stirred for 12 h at RT. The reaction mixture was diluted with MeCN (15 mL), additional tert-butylnitrite (1.00 mL, 8.34 mmol) was added and stirring was continued for an additional 24 h. The mixture was partitioned between sat. NaHCO$_3$ (aq) (80 mL) and EtOAc (200 mL). The aqueous phase was removed and the organic phase was washed with sat. NaHCO$_3$ (aq) (1×50 mL), 10% Na$_2$S$_2$O$_3$ (aq) (2×35 mL), and brine (2×35 mL). The combined aqueous washes were back-extracted with EtOAc (1×50 mL). The combined organics were dried (MgSO$_4$) and concentrated in vacuo. The residue was purified by silica gel chromatography (EtOAc/DCM) to afford N-(4-((6-iodo-4-methylpyridin-3-yl)oxy)pyridin-2-yl)acetamide (0.52 g, 49.2%) as a light yellow solid. $^1$H NMR (400 MHz, DMSO-d$_6$): δ 10.59 (s, 1H), 8.19 (s, 1H), 8.18 (d, J=5.7 Hz, 1H), 7.92 (s, 1H), 7.59 (s, 1H), 6.64 (dd, J=5.7, 2.5 Hz, 1H), 2.08 (s, 3H), 2.03 (s, 3H); MS (ESI) m/z: 370.0 (M+H$^+$).

N-(4-((6-iodo-4-methylpyridin-3-yl)oxy)pyridin-2-yl)acetamide (0.15 g, 0.41 mmol), Example C2 (0.11 g, 0.70 mmol), and K$_2$CO$_3$ (0.55 g, 3.98 mmol) were suspended in DMF (5 mL). The suspension was sonicated and sparged with Ar for 10 min. Copper(I) iodide (0.03 g, 0.16 mmol) and N,N-dimethylethane-1,2-diamine (0.012 g, 0.14 mmol) were added and the reaction mixture was stirred at 100° C. for 12 h. The reaction mixture was diluted with EtOAc (5 mL) and filtered through a pad of diatomaceous earth. The filter cake was washed with EtOAc (2×5 mL) and the combined filtrates were concentrated in vacuo. The residue was purified by silica gel chromatography (MeOH/DCM) to provide impure product as a brown solid. The solid was repurified by silica gel chromatography (MeOH/EtOAc) to afford N-(4((6-(3-(2-methoxypropan-2-yl)-5-oxo-4,5-dihydro-1H-1,2,4-triazol-1-yl)-4-methylpyridin-3-yl)oxy)pyridin-2-yl)acetamide (0.035 g, 19%) as a white solid. $^1$H NMR (400 MHz, DMSO-d$_6$): δ 12.20-12.18 (m, 1H), 10.57 (s, 1H), 8.27 (s, 1H), 8.18 (d, J=5.7 Hz, 1H), 7.98 (s, 1H), 7.59 (d, J=2.4 Hz, 1H), 6.67 (dd, J=5.7, 2.4 Hz, 1H), 3.06 (s, 3H), 2.18 (s, 3H), 2.02 (s, 3H), 1.46 (s, 6H); MS (ESI) m/z: 399.2 (M+H$^+$).

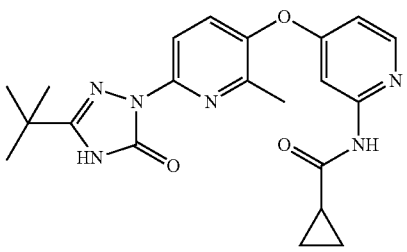 [SMILES: Cc1nc(-n2nc(C(C)(C)C)[nH]c2=O)ccc1Oc1ccnc(NC(=O)C2CC2)c1]

Example 45

A round bottom flask was charged with cyclopropane carboxamide (0.473 g, 5.56 mmol), Example A3 (0.400 g, 1.112 mmol), Cs$_2$CO$_3$ (0.54 g, 1.668 mmol), XPhos (0.053 g, 0.111 mmol) and dioxane (6 mL). The mixture was sparged with Ar under sonication for 10 min. Pd$_2$(dba)$_3$ (0.051 g, 0.056 mmol) was added and the mixture was sparged with Ar under sonication for 10 minutes. The reaction was then stirred at 100° C. overnight. The reaction was allowed to cool to RT, diluted with EtOAc. The mixture was washed with water, dried over anhydrous Na$_2$SO$_4$ and concentrated to dryness to afford a redish orange solid. The solid was chromatographed (0-5% MeOH/EtOAc) to afford a white solid. The product was suspended in CH$_3$CN/H$_2$O, frozen and lyophilized to provide N-(4-((6-(3-(tert-butyl)-5-oxo-4,5-dihydro-1H-1,2,4-triazol-1-yl)-2-methylpyridin-3-yl)oxy)pyridin-2-yl)cyclopropanecarboxamide as a fluffy white solid. (0.120 g, 26.4%) $^1$H NMR (400 MHz, DMSO-d$_6$) 11.98 (s, 1H), 10.88 (s, 1H), 8.20 (d, J=5.7 Hz, 1H), 7.85 (d, J=8.8 Hz, 1H), 7.69 (d, J=8.8 Hz, 1H), 7.54 (d, J=2.4 Hz, 1H), 6.70 (dd, J=5.7, 2.4 Hz, 1H), 2.28 (s, 3H), 1.98-1.90 (m, 1H), 1.27 (s, 9H), 0.77-0.72 (m, 4H); MS (ESI) m/z: 409.2 (M+H$^+$).

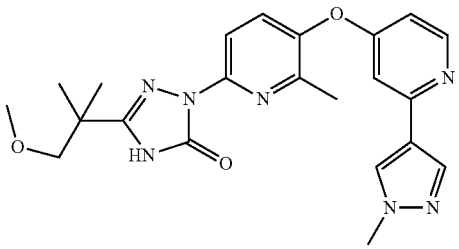 [SMILES: COCC(C)(C)c1nn(-c2ccc(Oc3ccnc(-c4cnn(C)c4)c3)c(C)n2)c(=O)[nH]1]

Example 46

Example C8 (0.60 g, 3.50 mmol), Example A1 (1.20 g, 3.50 mmol), and K$_2$CO$_3$ (2.50 g, 18.1 mmol) were suspended in DMF (4.5 mL). The mixture was sonicated and sparged with Ar for 10 min followed by sequential addition of copper (I) iodide (0.13 g, 0.70 mmol) and N,N-dimethylethane-1,2-diamine (0.06 g, 0.70 mmol). The reaction mixture was stirred at 100° C. for 16 h. The reaction mixture was partitioned between sat. NH4Cl (aq) (100 mL) and EtOAc (150 mL) and the resultant biphasic solution was mixed vigously for 10 min. The organic phase was collected and the aqueous phase was extracted with EtOAc (5×50 mL) and the combined organics were dried (Na$_2$SO$_4$) and concentrated in vacuo. The residue was triturated with MeCN (5 mL), sonicated, and the resultant white solid was collected by filtration to afford 1454(2-chloropyridin-4-yl)oxy)-6-methylpyridin-2-yl)-3-(1-methoxy-2-methylpropan-2-yl)-1H-1,2,4-triazol- 5(4H)-one (1.12 g, 82%) as a white solid. $^1$H NMR (400 MHz, DMSO-d$_6$): δ 11.93 (s, 1H), 8.29 (d, J=5.8 Hz, 1H), 7.86 (d, J=8.8 Hz, 1H), 7.74 (d, J=8.8 Hz, 1H), 7.06 (d, J=2.3 Hz, 1H), 6.96 (dd, J=5.8, 2.3 Hz, 1H), 3.39 (s, 2H), 3.24 (s, 3H), 2.31 (s, 3H), 1.24 (s, 6H); MS (ESI) m/z: 390.2 (M+H$^+$).

1-(5-((2-Chloropyridin-4-yl)oxy)-6-methylpyridin-2-yl)-3-(1-methoxy-2-methylpropan-2-yl)-1H-1,2,4-triazol-5(4H)-one (0.10 g, 0.26 mmol), 1-methyl-4-(4,4,5,5-tetramethyl-1,3,2-dioxaborolan-2-yl)-1H-pyrazole (0.07 g, 0.33 mmol), and K$_2$CO$_3$ (0.09 g, 0.66 mmol) were suspended in a solution of dioxane (2.0 mL) and water (0.4 mL). The suspension was sonicated and sparged with Ar for 10 min followed by the addition of Pd(PPh$_3$)$_4$ (0.03 g, 0.026 mmol). The reaction mixture was stirred at 85° C. for 12 h, allowed to cool to RT, diluted with water (2.0 mL), and extracted with EtOAc (5×3 mL). The combined organics were dried (Na$_2$SO$_4$) and concentrated in vacuo to afford an orange oil. The residue was purified by silica gel chromatography (MeOH/DCM) to afford 3-(1-methoxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one (0.085 g, 76%) as a white solid. $^1$H NMR (400 MHz, DMSO-d$_6$): δ 11.93 (s, 1H), 8.37 (d, J=5.7 Hz, 1H), 8.26 (s, 1H), 7.96 (s, 1H), 7.85 (d, J=8.8 Hz, 1H), 7.69 (d, J=8.8 Hz, 1H), 7.18 (d, J=2.4 Hz, 1H), 6.65 (dd, J=5.7, 2.5 Hz, 1H), 3.84 (s, 3H), 3.39 (s, 2H), 3.25 (s, 3H), 2.33 (s, 3H), 1.24 (s, 6H); MS (ESI) m/z: 436.2 (M+H$^+$).

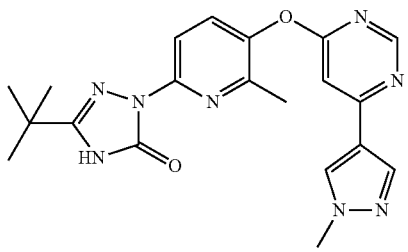 [SMILES: Cc1nc(-n2nc(C(C)(C)C)[nH]c2=O)ccc1Oc1cc(-c2cnn(C)c2)ncn1]

Example 47

2-Methylpyridin-3-ol (3.00 g, 27.5 mmol) was dissolved in a solution of Na$_2$CO$_3$ (5.83 g, 55.0 mmol) in water (48 mL) and MeOH (30 mL). Iodine (6.98 g, 27.5 mmol) was added and the reaction mixture was stirred for 1 h at RT. The mixture was treated with 2 M HCl solution (14 mL) and the resultant suspension was extracted with EtOAc (2×65 mL). The combined organics were washed with brine, dried (Na$_2$SO$_4$) and concentrated. The residue was slurried with DCM (20 mL) and the resultant solid was collected to afford 6-iodo-2-methylpyridin-3-ol (3.6 g, 55.7% yield) as a white solid. $^1$H NMR (400 MHz, CDCl$_3$): δ 7.41 (d, J=8.26 Hz, 1H), 6.78 (d, J=8.26 Hz, 1H), 5.03 (br s, 1H), 2.47 (s, 3H); MS (ESI) m/z: 236.0 (M+H$^+$).

6-Iodo-2-methylpyridin-3-ol (2.00 g, 8.51 mmol) and 4,6-dichloropyrimidine (5.00 g, 33.6 mmol) were dissolved in DMA (40 mL) and sonicated and sparged with Ar for 10 min. K$_2$CO$_3$ (2.00 g, 14.5 mmol) was added and the reaction mixture was stirred at 110° C. for 16 h. The mixture was partitioned between water (260 mL) and EtOAc (100 mL). The solids were removed by filtration through a pad of diatomaceous earth. The filter cake was washed with EtOAc (3×25 mL). The organic phase was collected and the aqueous phase was extracted with EtOAc (3×50 mL). The combined organics were dried (Na$_2$SO$_4$) and concentrated in vacuo to afford 4-chloro-6-((6-iodo-2-methylpyridin-3-yl)oxy)pyrimidine (2.8 g, 95%) as a yellow solid. $^1$H NMR (400 MHz, DMSO-d$_6$): δ 8.63 (s, 1H), 7.77 (d, J=8.3 Hz, 1H), 7.57 (s, 1H), 7.41 (d, J=8.3 Hz, 1H), 2.25 (s, 3H). MS (ESI) m/z: 348.0 (M+H$^+$).

Example C1 (0.20 g, 1.42 mmol), 4-chloro-6-((6-iodo-2-methylpyridin-3-yl)oxy)pyrimidine (0.50 g, 1.44 mmol), and K$_2$CO$_3$ (1.10 g, 7.94 mmol) were suspended in MeCN (14 mL). The suspension was sonicated and sparged with Ar for 10 min. Copper(I) iodide (0.055 g, 0.29 mmol) and N,N-dimethylethane-1,2-diamine (0.020 g, 0.14 mmol) were added and the reaction mixture was stirred at 100° C. for 16 h. The reaction mixture was diluted with sat. NH$_4$Cl (aq) (20 mL), filtered, and concentrated in vacuo. The aqueous suspension was extracted with EtOAc (5×15 mL) and the combined organics were dried (Na$_2$SO$_4$) and concentrated in vacuo. The residue was purified by silica gel chromatography (EtOAc/DCM followed by MeOH/EtOAc) to afford 3-(tert-butyl)-1-(5-((6-chloropyrimidin-4-yl)oxy)-6-methylpyridin-2-yl)-1H-1,2,4-triazol-5(4H)-one (0.10 g, 19.3%) as a white solid. $^1$H NMR (400 MHz, DMSO-d$_6$): δ 11.96 (s, 1H), 8.64 (d, J=0.9 Hz, 1H), 7.81 (d, J=8.8 Hz, 1H), 7.75 (d, J=8.8 Hz, 1H), 7.55 (s, 1H), 2.28 (s, 3H), 1.26 (s, 9H); MS (ESI) m/z: 361.1 (M+H$^+$).

3-(tert-Butyl)-1-(5-((6-chloropyrimidin-4-yl)oxy)-6-methylpyridin-2-yl)-1H-1,2,4-triazol-5(4H)-one (0.10 g, 0.28 mmol), 1-methyl-4-(4,4,5,5-tetramethyl-1,3,2-dioxaborolan-2-yl)-1H-pyrazole (0.08 g, 0.36 mmol), and K$_2$CO$_3$ (0.10 g, 0.72 mmol) were suspended in a solution of dioxane (2.5 mL) and water (0.50 mL). The suspension was sonicated and sparged with Ar for 10 min. Pd(PPh$_3$)$_4$ (0.032 g, 0.028 mmol) was added and the reaction mixture was stirred at 85° C. for 16 h. The mixture was diluted with sat. NH$_4$Cl (aq) 5 mL) and the resultant emulsion was extracted with EtOAc (4×10 mL). The combined organics were dried (Na$_2$SO$_4$) and concentrated in vacuo. The residue was purified by silica gel chromatography (MeOH/DCM) to afford a brown amorphous solid that was triturated with MeCN (1.5 mL). A white precipitate formed following sonication and was isolated by filtration and dried to afford 3-(tert-butyl)-1-(6-methyl-5-((6-(1-methyl-1H-pyrazol-4-yl)pyrimidin-4-yl)oxy)pyridin-2-yl)-1H-1,2,4-triazol-5(4H)-one (0.055 g, 48.3%) as a white solid. $^1$H NMR (400 MHz, DMSO-d$_6$): δ 11.95 (s, 1H), 8.61 (d, J=1.1 Hz, 1H), 8.48 (s, 1H), 8.17 (s, 1H), 7.80 (d, J=8.7 Hz, 1H), 7.73 (d, J=8.7 Hz, 1H), 7.46 (d, J=1.1 Hz, 1H), 3.89 (s, 3H), 2.29 (s, 3H), 1.27 (s, 9H); MS (ESI) m/z: 420.3 (M+H$^+$).

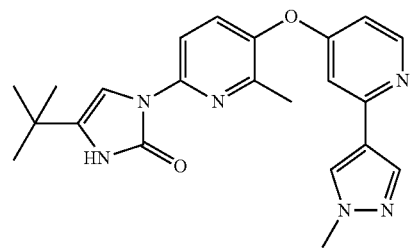 [SMILES: Cc1nc(-n2cc(C(C)(C)C)[nH]c2=O)ccc1Oc1ccnc(-c2cnn(C)c2)c1]

Example 48

A round bottom flask was charged with Example A12 (2.4 g, 6.69 mmol), 1-methyl-4-(4,4,5,5-tetramethyl-1,3,2-dioxaborolan-2-yl)-1H-pyrazole (1.531 g, 7.36 mmol), K$_2$CO$_3$ (1.017 g, 7.36 mmol), dioxane (40 mL) and water (10 mL) and spargd with Ar under sonication for ~10 minutes. Pd(PPh$_3$)$_4$ (0.309 g, 0.268 mmol) was added and the reaction was sparged again with Ar under sonication for ~10 minutes and then heated to 100° C. overnight. The reaction mixture was allowed to cool to RT, and extracted with EtOAc and sat'd NaHCO₃. The Aqueous layer was back-extracted with EtOAc (3×), the organic phases combined, dried (Na₂SO₄) and concentrated to dryness to afford a white solid. The solid was suspended in MeCN, sonicated and the solids were collected by filtration, washed with MeCN, and dried in the vacuum oven to afford 4-(tert-butyl)-1-(6-methyl-5-((2-(1-methyl-1H-pyrazol-4-yl)pyridin-4-yl)oxy)pyridin-2-yl)-1H-imidazol-2(3H)-one as a white solid (1.89 g, 69.9%). $^1$H NMR (400 MHz, DMSO-d₆): 10.59 (d, J=2.5 Hz, 1H), 8.36 (d, J=5.7 Hz, 1H), 8.26-8.25 (m, 2H), 7.96 (s, 1H), 7.67 (d, J=8.9 Hz, 1H), 7.16 (d, J=2.4 Hz, 1H), 6.87 (d, J=2.5 Hz, 1H), 6.62 (dd, J=5.7, 2.4 Hz, 1H), 3.84 (s, 3H), 2.31 (s, 3H), 1.19 (s, 9H); MS (ESI) m/z: 405.2 (M+H⁺).

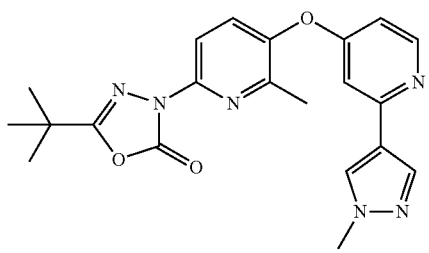 [SMILES: Cc1nc(-n2nc(C(C)(C)C)oc2=O)ccc1Oc1ccnc(-c2cnn(C)c2)c1]

Example 49

A mixture of Example A4 (0.20 g, 0.67 mmol) in DCM (4 mL) was cooled in an ice-water bath and treated with trimethylacetyl chloride (0.16 g, 1.35 mmol). The mixture was allowed to warm up to RT and stirred for 30 min. The reaction mixture was cooled to 0° C. and then diluted with DCM (4 mL). Triethylamine (0.5 mL, 3.61 mmol) was added and then a solution of triphosgene (80 mg, 0.26 mmol) in DCM (4 mL) was added drop-by-drop under the same conditions. The reaction mixture was allowed to warm to RT and stirred at RT overnight. The mixture was quenched with NaHCO3 solution and extracted with DCM (2×). The organic was dried over Na₂SO₄, filtered and concentrated in vacuo. The crude product was purified via silica gel chromatography (EtOAc) to obtain 5-(tert-butyl)-3-(6-methyl-5-((2-(1-methyl-1H-pyrazol-4-yl)pyridin-4-yl)oxy)pyridin-2-yl)-1,3,4-oxadiazol-2(3H)-one (114 mg, 37.8%). $^1$H NMR (400 MHz, DMSO-d₆): δ 8.39 (d, J=5.7 Hz, 1H), 8.27 (s, 1H), 7.97 (s, 1H), 7.78 (d, J=8.7 Hz, 1H), 7.70 (d, J=8.8 Hz, 1H), 7.23 (d, J=2.4 Hz, 1H), 6.67 (dd, J=5.7, 2.4 Hz, 1H), 3.85 (s, 3H), 2.37 (s, 3H), 1.33 (s, 9H); MS (ESI) m/z: 407.2 (M+H⁺).

The following assays demonstrate that certain compounds of Formula I inhibit kinase activity of c-FMS kinase, c-KIT kinase, or PDGFRβ kinase in enzymatic assays and also inhibit the activity of c-FMS kinase in M-NFS-60 and THP-1 cell lines. In vivo evaluations of certain compounds of Formula I also demonstrate inhibition of c-FMS in a pharmcodynamic model or also exhibit efficacy in a peritibial implant model, a U-251 or GL-261 glioma model, or in a MDA-MB-231 breast cancer xenograft model.

uFMS Kinase (Seq. ID No. 1) Assay

Activity of unphosphorylated c-FMS kinase (uFMS, Seq. ID no. 1) was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained FMS (purchased from Millipore) (10 nM), polyE4Y (1 mg/mL), MgCl₂ (10 mM), pyruvate kinase (4 units), lactate dehydrogenase (0.7 units), phosphoenol pyruvate (1 mM), NADH (0.28 mM) and ATP (500 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). IC₅₀ values were calculated from a series of percent inhibition values determined at a range of inhibitor concentrations using software routines as implemented in the GraphPad Prism software package.

```
uFMS Kinase sequence (Y538-end) used for screening
                                          (Seq. ID No. 1)
YKYKQKPKYQ  VRWKIIESYE  GNSYTFIDPT  QLPYNEKWEF

PRNNLQFGKT  LGAGAFGKVV  EATAFGLGKE  DAVLKVAVKM

LKSTAHADEK  EALMSELKIM  SHLGQHENIV  NLLGACTHGG

PVLVITEYCC  YGDLLNFLRR  KAEAMLGPSL  SPGQDPEGGV

DYKNIHLEKK  YVRRDSGFSS  QGVDTYVEMR  PVSTSSNDSF

SEQDLDKEDG  RPLELRDLLH  FSSQVAQGMA  FLASKNCIHR

DVAARNVLLT  NGHVAKIGDF  GLARDIMNDS  NYIVKGNARL

PVKWMAPESI  FDCVYTVQSD  VWSYGILLWE  IFSLGLNPYP

GILVNSKFYK  LVKDGYQMAQ  PAFAPKNIYS  IMQACWALEP

THRPTFQQIC  SFLQEQAQED  RRERDYTNLP  SSSRSGGSGS

SSSELEEESS  SEHLTCCEQG  DIAQPLLQPN  NYQFC
``` uKit Kinase (Seq. ID No. 2) Assay

Activity of unphosphorylated c-KIT kinase (uKIT, Seq. ID no. 2) was determined by following the production of ADP from the KIT kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μl) contained unphosphorylated KIT (12 nM), polyE4Y (1 mg/mL), MgCl₂ (10 mM), pyruvate kinase (4 units), lactate dehydrogenase (0.7 units), phosphoenol pyruvate (1 mM), and NADH (0.28 mM) and ATP (2000 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader (BioTech). Reaction rates around 3 to 4 h time frame were used to calculate % inhibitions, from which IC₅₀ values were generated.

```
uKit with N-terminal GST fusion used for screening
                                          (Seq ID No. 2)
LGYWKIKGLV  QPTRLLLEYL  EEKYEEHLYE  RDEGDKWRNK

KFELGLEFPN  LPYYIDGDVK  LTQSMAIIRY  IADKHNMLGG

CPKERAEISM  LEGAVDIRYG  VSRIAYSKDF  ETLKVDFLSK
```

-continued

```
LPEMLKMFED RLCHKTYLNG DHVTHPDFML YDALDVVLYM

DPMCLDAFPK LVCFKKRIEA IPQIDKYLKS SKYIWPLQGW

QATFGGGDHP PKSDLVPRHN QTSLYKKAGS AAAVLEENLY

FQGTYKYLQK PMYEVQWKVV EEINGNNYVY IDPTQLPYDH

KWEFPRNRLS FGKTLGAGAF GKVVEATAYG LIKSDAAMTV

AVKMLKPSAH LTEREALMSE LKVLSYLGNH MNIVNLLGAC

TIGGPTLVIT EYCCYGDLLN FLRRKRDSFI CSKQEDHAEA

ALYKNLLHSK ESSCSDSTNE YMDMKPGVSY VVPTKADKRR

SVRIGSYIER DVTPAIMEDD ELALDLEDLL SFSYQVAKGM

AFLASKNCIH RDLAARNILL THGRITKICD FGLARDIKND

SNYVVKGNAR LPVKWMAPES IFNCVYTFESD VWSYGIFLWE

LFSLGSSPYP GMPVDSKFYK MIKEGFRMLS PEHAPAEMYD

IMKTCWDADP LKRPTFKQIV QLIEKQISES TNHIYSNLAN

CSPNRQKPVV DHSVRINSVG STASSSQPLL VHDDV
```

Unphosphorylated PDGFRβ (uPDGFRβ) Kinase (Seq. ID No. 3) Assay

Activity of unphosphorylated PDGFRβ kinase (uPDGFRβ, Seq. ID No. 3) was determined by following the production of ADP from the kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained PDGFRβ (DeCode, 15.7 nM), polyE4Y (2.5 mg/mL), $MgCl_2$ (10 mM), pyruvate kinase (4 units), lactate dehydrogenase (0.7 units), phosphoenol pyruvate (1 mM) and NADH (0.28 mM) and ATP (500 μM) in a 90 mM Tris buffer containing 0.2% octyl-glucoside and 1% DMSO, at pH 7.5. The inhibition reaction was started by mixing serial diluted test compound with the above reaction mixture. The absorption at 340 nm was monitored continuously for 4 h at 30° C. on a Polarstar Optima or Synergy 2 plate reader. The reaction rate was calculated using the 1.5 to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

```
uPDGFRβ Kinase Sequence (residues 557-1106) used
for screening
                                      (Seq ID No. 3)
QKKPRYEIRW KVIESVSSDG HEYIYVDPMQ LPYDSTWELP

RDQLVLGRTL GSGAFGQVVE ATAHGLSHSQ ATMKVAVKML

KSTARSSEKQ ALMSELKIMS HLGPHLNVVN LLGACTKGGP

IYIITEYCRY GDLVDYLHRN KHTFLQHHSD KRRPPSAELY

SNALPVGLPL PSHVSLTGE SDGGYMDMSK DESVDYVPML

DMKGDVKYAD IESSNYMAPY DNYVPSAPER TCRATLINES

PVLSYMDLVG FSYQVANGME FLASKNCVHR DLAARNVLIC

EGKLVKICDF GLARDIMRDS NYISKGSTFL PLKWMAPESI

FNSLYTTLSD VWSFGILLWE IFTLGGTPYP ELPMNEQFYN

AIKRGYRMAQ PAHASDEIYE IMQKCWEEKF EIRPPFSQLV

LLLERLLGEG YKKKYQQVDE EFLRSDHPAI LRSQARLPGF

HGLRSPLDTS SVLYTAVQPN EGDNDYIIPL PDPKPEVADE

GPLEGSPSLA SSTLNEVNTS STISCDSPLE PQDEPEPEPQ

LELQVEPEPE LEQLPDSGCP APRAEAEDSF L
```

Using the enzymatic protocols described above, compounds of Formula I were shown to be inhibitors in assays measuring the kinase activity of uFMS kinase, uKIT kinase, or uPDGFRβ kinase, as indicated below in Table 1.

TABLE 1

Activity of Compounds of Formula I in Enyzmatic Assays of uFMS kinase, uKIT kinase, or uPDGFRβ kinase.

| Example | uFMS | uKIT | uPDGFRβ |
|---|---|---|---|
| 1 | ++++ | ++ | ++ |
| 2 | ++++ | ++ | ++ |
| 3 | ++++ | +++ | +++ |
| 4 | ++++ | +++ | + |
| 5 | +++ | ++ | + |
| 6 | ++++ | +++ | ++ |
| 7 | ++++ | ++ | + |
| 8 | ++ | + | + |
| 9 | +++ | ++ | + |
| 10 | +++ | + | + |
| 11 | +++ | + | + |
| 12 | +++ | ++ | + |
| 13 | +++ | ++ | + |
| 14 | ++++ | +++ | + |
| 15 | +++ | + | + |
| 16 | +++ | + | + |
| 17 | ++ | + | NT |
| 18 | +++ | ++ | + |
| 19 | +++ | + | + |
| 20 | ++++ | ++ | + |
| 21 | ++ | + | + |
| 22 | ++++ | +++ | + |
| 23 | +++ | + | + |
| 24 | ++ | + | + |
| 25 | ++++ | +++ | + |
| 26 | +++ | + | + |
| 27 | ++++ | ++ | + |
| 28 | ++++ | +++ | + |
| 29 | +++ | ++ | + |
| 30 | +++ | + | + |
| 31 | ++++ | +++ | ++ |
| 32 | +++ | +++ | ++ |
| 33 | +++ | ++ | ++ |
| 34 | ++++ | ++++ | +++ |
| 35 | ++ | ++ | + |
| 36 | ++++ | +++ | ++ |
| 37 | ++++ | ++ | ++ |
| 38 | ++++ | + | + |
| 39 | +++ | + | + |
| 40 | +++ | ++ | + |
| 41 | ++ | + | + |
| 42 | +++ | + | + |
| 43 | ++++ | +++ | ++ |
| 44 | ++ | ++ | ++ |
| 45 | ++ | + | + |
| 46 | +++ | ++ | + |
| 47 | +++ | + | + |

TABLE 1-continued

Activity of Compounds of Formula I in Enyzmatic Assays of uFMS kinase, uKIT kinase, or uPDGFRβ kinase.

| Example | uFMS | uKIT | uPDGFRβ |
|---------|------|------|---------|
| 48 | +++ | + | + |
| 49 | +++ | ++ | + |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM M-NFS-60 Cell Culture M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

M-NFS-60 Cell Proliferation Assay

A serial dilution of test compound was dispensed into a 384-well black clear bottom plate (Corning, Corning, N.Y.). Two thousand five hundred cells were added per well in 50 μL complete growth medium. Plates were incubated for 67 h at 37° C., 5% $CO_2$, and 95% humidity. At the end of the incubation period 10 μL of a 440 μM solution of resazurin (Sigma, St. Louis, Mo.) in PBS was added to each well and incubated for an additional 5 h at 37° C., 5% $CO_2$, and 95% humidity. Plates were read on a Synergy2 reader (Biotek, Winooski, Vt.) using an excitation of 540 nM and an emission of 600 nM. $IC_{50}$ values were calculated from a series of percent inhibition values determined at a range of inhibitor concentrations using software routines as implemented in the GraphPad Prism software package.

THP-1 Cell Culture

THP-1 cells (catalog #TIB-202) were obtained from the ATCC. Briefly, cells were grown in RPMI 1640 supplemented with 10% characterized fetal bovine serum, 1% sodium pyruvate, 1% Penicillin-Streptomycin-Glutamine (PSG) and 55 uM 2-mercaptoethanol (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

Phospho-FMS ELISA Assay

A serial dilution of test compound was diluted 1:100 in assay medium (RPMI 1640 supplemented with 10% characterized fetal bovine serum) in a 96 well black clear bottom plate (Corning, Corning, N.Y.). In a separate 96 well black clear bottom plate, one hundred and fifty thousand THP-1 cells were added per well in 100 μL in assay medium. Fifty microliters of diluted compound was then added to the cells. Plates were incubated for 4 hours at 37 degrees Celsius, 5% $CO_2$, 95% humidity. At the end of the incubation period, cells were stimulated with 50 μL of a 100 nM solution of recombinant human M-CSF (catalog #216-MC, R & D Systems, Minneapolis, Minn.) in assay medium and the plate was incubated for 5 minutes at 37 degrees Celsius, 5% $CO_2$, 95% humidity. Lysates were prepared and used to perform the phospho-FMS ELISA as described by the manufacturer (catalog #DYC3268, R & D Systems, Minneapolis, Minn.). GraphPad Prism was used to calculate $IC_{50}$ values obtained from data generated from the ELISA assay.

Osteoclast Tartrate-Resistant Acid Phosphatase Assay

A serial dilution of test compound was dispensed into a 384-well black clear bottom plate (Nalge Nunc International, Rochester, N.Y.). Compound was diluted by the addition of DMEM media supplemented with 10% characterized fetal bovine serum (Invitrogen, Carlsbad, Calif.). Diluted compound was transferred to a 384-well black clear bottom plate. Two-thousand five hundred osteoclast precursors (Lonza, Walkersville, Md.) were added per well in growth media containing Receptor Activator of Nuclear Factor Kappa-beta ligand (RANKL) and M-CSF (R&D Systems, Minneapolis, Minn.). Plates were incubated for 7-14 days at 37 degrees Celsius, 5% $CO_2$, and 95% humidity to allow differentiation of osteoclast precursors. At the end of the incubation period, 10 μL of supernatant from each well was transferred to a clear 384-well plate. Tartrate-resistant acid phosphatase activity in the supernatant samples was determined using an acid phosphatase assay kit (Sigma, St. Louis, Mo.). Absorbance was measured at 550 nm using a plate reader. Data was analyzed using Prism software (Graphpad, San Diego, Calif.) to calculate $IC_{50}$ values.

The compounds of Formula I were demonstrated to be functional inhibitors in one or more of the cellular assays described above, as indicated in Table 2.

TABLE 2

Inhibitory effects of compounds of Formula I versus M-NFS-60, THP-1 and Osteoclast Cells

| Example | M-NFS-60 cell proliferation | Osteoclast assay | pFMS inhibition in THP-1 cells |
|---------|------|------|------|
| 1 | +++ | +++ | +++ |
| 2 | +++ | +++ | ++++ |
| 3 | +++ | +++ | +++ |
| 4 | +++ | +++ | +++ |
| 5 | +++ | +++ | +++ |
| 6 | ++++ | +++ | ++++ |
| 7 | +++ | +++ | +++ |
| 8 | ++ | ++ | NT |
| 9 | +++ | +++ | +++ |
| 10 | +++ | +++ | +++ |
| 11 | ++ | ++ | NT |
| 12 | +++ | +++ | NT |
| 13 | ++ | ++ | ++ |
| 14 | +++ | ++++ | +++ |
| 15 | + | ++ | NT |
| 16 | ++ | +++ | ++ |
| 17 | + | + | NT |
| 18 | ++ | ++ | NT |
| 19 | ++ | ++ | NT |
| 20 | ++ | ++ | ++ |
| 21 | + | ++ | NT |
| 22 | ++++ | +++ | ++++ |
| 23 | ++ | +++ | NT |
| 24 | ++ | ++ | NT |
| 25 | +++ | +++ | +++ |
| 26 | + | ++ | NT |
| 27 | +++ | +++ | +++ |
| 28 | +++ | +++ | NT |
| 29 | ++ | ++ | NT |
| 30 | + | +++ | ++ |
| 31 | +++ | +++ | +++ |
| 32 | ++ | ++ | NT |
| 33 | ++ | ++ | +++ |
| 34 | ++++ | +++ | NT |
| 35 | + | ++ | NT |
| 36 | +++ | +++ | +++ |
| 37 | +++ | ++++ | ++++ |
| 38 | +++ | +++ | ++ |
| 39 | +++ | +++ | ++ |
| 40 | +++ | +++ | NT |
| 41 | + | ++ | NT |
| 42 | + | ++ | NT |
| 43 | ++ | +++ | ++ |

TABLE 2-continued

Inhibitory effects of compounds of Formula I versus
M-NFS-60, THP-1 and Osteoclast Cells

| Example | M-NFS-60 cell proliferation | Osteoclast assay | pFMS inhibition in THP-1 cells |
|---|---|---|---|
| 44 | ++ | ++ | NT |
| 45 | ++ | +++ | NT |
| 46 | ++ | +++ | ++ |
| 47 | ++ | +++ | +++ |
| 48 | +++ | +++ | +++ |
| 49 | +++ | +++ | +++ |

NT: Not Tested;
+: $IC_{50} > 1$ uM;
++: $0.1$ uM $< IC_{50} \le 1$ uM;
+++: $0.01$ uM $< IC_{50} \le 0.1$ uM;
++++: $IC_{50} \le 0.01$ uM;

MEASUREMENTS OF IN VIVO ACTIVITY

Analysis of cFOS mRNA Production in a c-FMS Mouse Spleen Pharmacodynamic Model

To examine the in vivo modulation of FMS activity by compounds of Formula I, spleen samples from female DBA/1 mice were collected and analyzed for M-CSF stimulated production of cFOS mRNA. Briefly, six to seven week old female Taconic DBA/1BO J Bom Tac mice were treated with a single oral dose (by gavage) of either vehicle or compound. Plasma and spleen samples were collected from four mice at each timepoint 2, 4, 6, 8, 12, 18, and 24 hours after dosing. Fifteen minutes prior to euthanasia, all mice were injected IV with 1 µg (100 µL fixed volume) of M-CSF. M-CSF, Recombinant Mouse Macrophage Colony Stimulating Factor (36.4 kDa homodimer, ≥98% purity) was obtained from Gibco. All procedures carried out in this experiment were conducted in compliance with all the laws, regulations and guidelines of the National Institutes of Health (NIH). cFOS mRNA levels in spleen extracts were determined using a quantitative reverse transcriptase PCR kit from Life Technologies. Plasma levels of FMS inhibitors were determined by mass spectrometer analysis. The degree of FMS inhibition was correlative to the amount of decrease observed in cFOS mRNA levels in the spleen samples of treated animals compared to vehicle.

In this model, Examples 7, 9, 25 and 48 afforded ≥70% inhibition of cFOS mRNA levels out to 8 h post 30 mg/kg dose.

PC-3 Peritibial Implant Model of Cancer Bone Metastasis

To evaluate in vivo anti-cancer activity of compounds of Formula I, the PC-3 M-luc peritibial injection model of bone invasiveness model is employed. Briefly, PC-3 M-luc cells are obtained from Xenogen Corporation (Caliper Life Sciences) and expanded using MEM media modified with L-Glutamine (Cell Gro® #10-045-CV) supplemented with 10% fetal bovine serum, 1% penicillin-streptomycin-glutamine, 1% non-essential amino acids, and 1% MEM vitamins in 5% $CO_2$ atmosphere at 37° C. Six to 7 week old male nude mice (Crl:NU-Foxnlnu) are obtained from Charles River Laboratories. Test mice are implanted peritibially on Day 0 with $1 \times 10^6$ cells/mouse (00.1 mL) using an insulin syringe with a fixed 28-gauge needle. The needle is inserted at the ankle between the tibia and fibula until the bevel of the needle reaches approximately half way between the knee and ankle Treatments begin on Day 0. Animals are dosed by oral gavage twice daily for the study duration. All procedures carried out in this experiment are conducted in compliance with all the laws, regulations and guidelines of the National Institutes of Health (NIH). When the primary tumor reaches approximately 800 mg in size, ex-vivo micro-CT is performed on the tumor bearing fixed hind limb samples using a GE RS 150 small animal micro-CT scanner using with the following settings:

X-ray tube voltage=70 kVp
X-ray tube current=25 mA
Exposure time=20 ms
Number of frames=500
Angle increment between frames=0.4o
Number of averages per frame=2
Acquisition method=Parker Images are then reconstructed at high resolution (100 microns;isotropic). Isosurface volume renderings are used to delineate lesions in the hind limbs. A constant threshold is used to produce consistent representation of the isosurface between different anatomical sites and samples. Lesions in the right hind limb are scored with values of 0, 1, 2, 3, or 4 based on a qualitative assessment of lesion size as defined by:

0: Normal Bone
1: Minimal lesions. Some roughening of the isosurface. Small areas of apparent bone resorption.
2: Mild. More numerous lesions. Significant roughening of the isosurface. Full thickness lesions apparent.
3: Moderate. Full thickness lesions larger and more numerous.
4: Marked. Many, large, full thickness lesions. Significant distortion of remaining structure. Marked bone loss.

U251 Intra-Cerebro-Ventricular Implant in Mice

To evaluate in vivo anti-cancer activity compounds of Formula I in combination with fractionated, localized head radiation, an orthotopic U251-luc (Luc) human glioma carcinoma model in female outbred nu/nu mice is employed. Briefly, U251 cells are obtained from the ATCC and altered to be luciferase expressing. They are grown in RPMI 1640 Media supplemented with 10% FBS and 1% PSG. The growth environment is maintained in an incubator with a 5% $CO_2$ atmosphere at 37° C. Female Harlan Nude mice (Hsd:Athymic-Nude-Fox1nu) 8-9 weeks old are used in this study. Test animals are implanted intracranially with U251-luc (Lucm-Cherry) cells. Briefly, animals are injected subcutaneously with 5 mg/kg carprofen and anesthetized using 2% isoflurane in air. The animals are then secured in a stereotaxic frame (ASlinstruments, Inc.) and a hole drilled 2 mm right lateral, 1 mm anterior to the coronal suture. The cell suspension (stored on wet ice) is mixed thoroughly and drawn up into a 50 µl syringe. The syringe needle is centered over the burr hole and lowered 3 mm into the brain and retracted 1 mm to form a "reservoir" for the deposition of the cell suspension. 10 µl of the cell suspension ($1 \times 10^6$ cells/mouse) is then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. All procedures carried out in this experiment are conducted in compliance with all the laws, regulations and guidelines of the National Institutes of Health (NIH). Treatment begins when the mean brain bioluminescence signal for all groups in the experiment is $\sim 1.3 \times 10^9$ photons/sec (typically 9 days post-implant). All mice receive 2Gy of radiation each day for five consecutive days from a RadSource RS-2000 irradiator. Additionally, mice receive test compound dosed by oral gavage or optionally with co-administered bevacizumab by tail vein injection. Bioluminescence images are acquired generally on days 8, 10, 14, 17, 21, 22, 24, 28 and 35 post-implant for tumor burden estimation. For each measurement, each mouse is injected subcutaneously with 150 mg/kg D-Luciferin (Promega) and imaged 10 minutes after the injection. Images are analyzed using Living Image (Xenogen, Alameda, Calif.) software. The BLI signal in the brain is calculated with a fixed area ROI to estimate the tumor burden. Average BLI signal for each group is compared to vehicle control to determine therapeutic benefit. Twenty-eight days after the first radiation treatment mice are euthanized, via over-exposure to carbon dioxide, for blood and brain collection. Whole blood is collected via terminal cardiac puncture and placed into EDTA Microtainer® tubes. Brains are excised and placed into 10% neutral buffered formalin.

GL261 Intracranial Implant Model

To evaluate the in vivo anti-cancer activity of compounds of Formula I, an intracranial implant of GL261-luc2 murine glioma is employed. Briefly GL261-luc2 cells are obtained from Caliper Life Sciences, Inc and expanded in Dulbecco's Modified Eagle Media (DMEM) which is supplemented with 10% FBS and 1% PSG. The growth environment is maintained in an incubator with a 5% $CO_2$ atmosphere at 37° C. Following expansion, cells are re-suspended using serum-free media to generate a concentration of $1 \times 10^8$ cells/mL. Six to seven week old female C57BL/6J-Tyrc-2J/J from Jackson Labs are implanted intracranially on Day 0 with GL261-luc2 cells. For aseptic surgical implantation, animals are injected subcutaneously with 5 mg/kg carprofen, anesthetized using 2% isoflurane in air. The animals are then secured in a stereotaxic frame (ASlinstruments, Inc.) and a hole is drilled 2 mm right lateral, 1 mm anterior to the coronal suture. The cell suspension (stored on wet ice) is mixed thoroughly and drawn up into a 50 µL syringe. The syringe needle is centered over the burr hole and lowered 3 mm into the brain and retracted 1 mm to form a "reservoir" for the deposition of the cell suspension. 10 µL of the cell suspension ($1 \times 10^6$ cells/mouse) is then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. The quantity of emitted light from the tumor after systemic injection of D-Luciferin is expected to correlate with tumor size. Each mouse is injected intraperitoneally (IP) with 150 mg/kg D-Luciferin and imaged in the prone position 10 minutes after the injection. Medium and small binning of the CCD chip is used, and the exposure time is adjusted (10 seconds to 1 minute) to obtain at least several hundred counts from the tumors and to avoid saturation of the CCD chip. Images are analyzed using Living Image (Xenogen, Alameda, Calif.) software. Each unique signal is circled manually and labeled by group and mouse number. Treatment begins by oral gavage of test compound when the mean brain bioluminescence signal for all groups in the experiment is $280 \times 10^6$ photons/sec. All procedures carried out in this experiment are conducted in compliance with all the laws, regulations and guidelines of the National Institutes of Health (NIH).

At the end of study all mice are euthanized via over-exposure to carbon dioxide for blood and brain collection. Whole blood is collected via terminal cardiac puncture and placed into EDTA Microtainer® tubes. Brains are excised and placed into 10% neutral buffered formalin.

MDA-MB-231 Xenograft Study

To evaluate the in vivo anti-cancer activity compounds of Formula I, a MDA-MB-231-luc-D3H2LN human breast carcinoma xenograft was employed. Briefly, MDA-MB-231-luc-D3H2LN cells were obtained from Xenogen and expanded in Minimal Essential Media (MEM) with EBSS which was modified with 1% L-glutamine and supplemented with 10% FBS, 1% PSG, 1% non-essential amino acids, and 1% sodium pyruvate. The growth environment was maintained in an incubator with a 5% $CO_2$ atmosphere at 37° C. Cells were harvested and re-suspended using 50% serum-free media and 50% Matrigel® to generate a stock concentration of $5 \times 10^6$ cells/mL.

Six to 7 week old female C.B-17/IcrHsd-PrkdcscidLystbg mice were injected with 200 µL of cell suspension subcutaneously, just below the right axilla. All procedures carried out in this experiment were conducted in compliance with all the laws, regulations and guidelines of the National Institutes of Health (NIH). Treatment began when the mean tumor burden is approximately 150 mg. All mice were dosed with test compound by oral gavage. Body weights and tumor measurements were recorded three times weekly. Tumor burden (mg) was estimated from caliper measurements by the formula for the volume of a prolate ellipsoid assuming unit density as: Tumor burden (mg)=$(L \times W2)/2$, where L and W are the respective orthogonal tumor length and width measurements (mm). The primary endpoints to evaluate efficacy were % T/C. % T/C is defined as the median tumor mass of a Treated Group divided by the median tumor mass of the Control Group×100. Ex vivo bioluminescence imaging was performed as animals exit the study, using an IVIS 50 optical imaging system (Xenogen, Alameda, Calif.). Animals were injected IP with 150 mg/kg D-Luciferin (Promega) and euthanized 10 minutes following the injection. The primary tumor was removed and snap frozen for future analysis and the mouse opened and imaged in the supine position. Large binning of the CCD chip was used, and the exposure time is adjusted (1 to 2 minutes) to obtain at least several hundred counts from the tumors and to avoid saturation of the CCD chip. Images were analyzed using Living Image (Xenogen, Alameda, Calif.) software. Each unique signal was circled manually and labeled by group and mouse number. Total BLI signal was correlative to tumor size and compared to vehicle control to determine treatment benefit.

Example 7 exhibited 39% tumor growth inhibition in this model when orally dosed at 15 mpk twice daily.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:
1. A compound of Formula I,

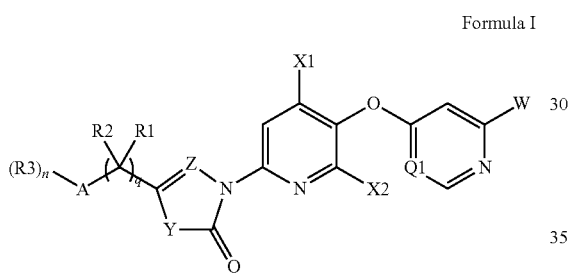

Formula I or a pharmaceutically acceptable salt, enantiomer, stereoisomer, or tautomer thereof,
wherein
A is selected from the group consisting of C1-C6 alkyl, branched C3-C8alkyl, fluoroC1-C6alkyl wherein the alkyl is fully or partially fluorinated, C3-C8carbocyclyl, phenyl, 4-8 membered heterocyclic ring and heteroaryl, wherein each A moiety may be further substituted with one, two, or three R3 moieties;
W is C5-C6heteroaryl, phenyl, —NHC(O)R6, —NHC(O)R7, —NHC(O)N(R8)R9 or —C(O)N(R8)R9, and wherein each C5-C6heteroaryl or phenyl is optionally substituted by one, two, or three R5 moieties;
Q1 is CH or N;
X1 and X2 are individually and independently hydrogen, or C1-C6 alkyl;
Y is NR4 or O;
Z is N or CR11;
each R1 and R2 is individually and independently hydrogen, C1-C6 alkyl, deutero-C1-C6 alkyl wherein the alkyl chain is partially or completely deuterated, fluoroC1-C6alkyl wherein the alkyl is fully or partially fluorinated, hydroxyl, C1-C6 alkoxy, fluoroC1-C6alkoxy wherein the alkyl group is fully or partially fluorinated, or halogen;
each R3 is individually and independently hydrogen, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;
R4 is hydrogen, C1-C6 alkyl, deutero-C1-C6 alkyl wherein the alkyl chain is partially or completely deuterated, or branched C3-C8 alkyl;
each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—OR8, —(CH$_2$)$_m$—NR8(R9), or —(CH$_2$)$_m$—R7, wherein each alkylene is optionally substituted with C1-C4 alkyl;
Each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkylene is optionally substituted with C1-C4 alkyl;
each R7 is independently and individually selected from the group consisting of

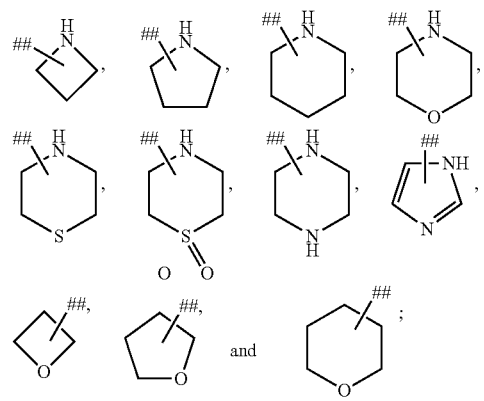

and wherein the symbol (##) is the point of attachment to respective W, R5 or R6 moieties containing a R7 moiety;
each R7 is optionally substituted with —(R10)$_p$;

each R8 and R9 is individually and independently hydrogen, C1-C6 alkyl, fluoro-C1-C6 alkyl wherein the alkyl chain is partially or completely fluorinated, or branched C3-C8 alkyl;

each R10 is individually and independently C1-C6 alkyl, —(CH$_2$)$_m$—CN, —(CH$_2$)$_m$—OR3, —(CH$_2$)$_m$—NR8(R9), or —(CH$_2$)$_m$—C(O)—R6, wherein each alkyl or alkylene is optionally substituted with one or two C1-C6 alkyl;

wherein each alkylene is optionally substituted with C1-C4 alkyl;

R11 is hydrogen, C1-C6 alkyl, deutero-C1-C6 alkyl wherein the alkyl chain is partially or completely deuterated, or branched C3-C8 alkyl;

each m is individually and independently 0, 1, 2, or 3;
each n is individually and independently 0, 1, 2, or 3;
each p is 0, 1, 2, or 3; and
each q is 0, 1, or 2.

2. The compound of claim 1, wherein W is selected from the group consisting of pyrazolyl, phenyl, imidazolyl, isoxazolyl, oxazolyl, thiazolyl, triazolyl, pyridinyl, —NHC(O)R6, —NHC(O)R7, —NHC(O)N(R8)R9, and —C(O)N(R8)R9.

3. The compound of claim 2, wherein the compound is a compound of Formula Ia,

Formula Ia

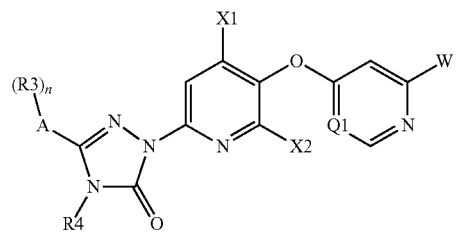

or a pharmaceutically acceptable salt, enantiomer, stereoisomer, or tautomer thereof.

4. The compound of claim 3, wherein A is C1-C6 alkyl, branched C3-C8alkyl, C3-C8carbocyclyl, phenyl or a 4-8 membered heterocyclic ring and q is 0 or 1.

5. The compound of claim 4, wherein W is pyrazolyl or pyridinyl, optionally substituted with —(R5)$_p$.

6. The compound of claim 5 wherein Y is NR4 and R4 is hydrogen.

7. The compound of claim 2, wherein the compound is a compound of Formula Ib,

Formula Ib

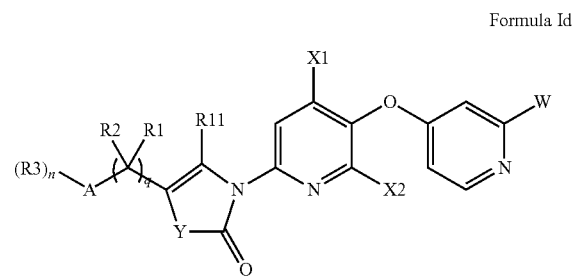

or a pharmaceutically acceptable salt, enantiomer, stereoisomer, or tautomer thereof,
wherein the A moiety is selected from C1-C6 alkyl, branched C3-C8alkyl, C3-C8carbocyclyl, phenyl or a 4-8 membered heterocyclic ring.

8. The compound of claim 7, wherein W is pyrazolyl or pyridinyl, optionally substituted with —(R5)$_p$.

9. The compound of claim 8, wherein R4 is hydrogen.

10. The compound of claim 1, wherein the compound is a compound of Formula Ic,

Formula Ic

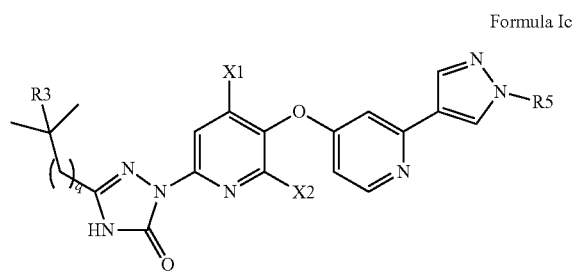

or a pharmaceutically acceptable salt, enantiomer, stereoisomer, or tautomer thereof,
wherein q is 0 or 1.

11. The compound of claim 2, wherein the compound is a compound of Formula Id,

Formula Id

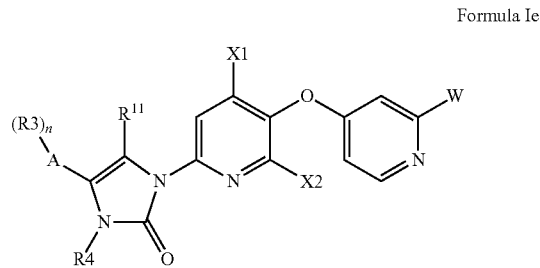

or a pharmaceutically acceptable salt, enantiomer, stereoisomer, or tautomer thereof.

12. The compound of claim 2, wherein the compound is a compound of Formula Ie,

Formula Ie or a pharmaceutically acceptable salt, enantiomer, stereoisomer, or tautomer thereof,
wherein the A moiety is selected from C1-C6 alkyl, branched C3-C8alkyl, C3-C8carbocyclyl, phenyl or a 4-8 membered heterocyclic ring.

13. The compound of claim 12, wherein W is pyrazolyl, optionally substituted with —(R5)$_p$.

14. The compound of claim 13, wherein R4 is hydrogen.

15. The compound of claim 1, wherein the compound is a compound of Formula If,

Formula If

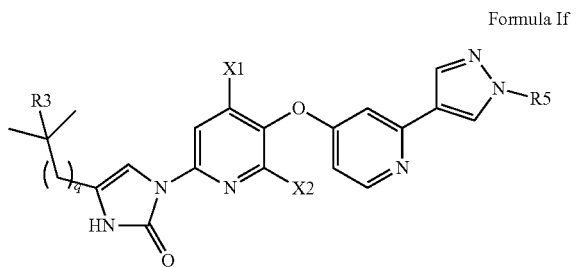

or a pharmaceutically acceptable salt, stereoisomer, or tautomer thereof,
wherein q is 0 or 1.

16. The compound of claim 2, wherein the compound is a compound of Formula Ig,

Formula Ig

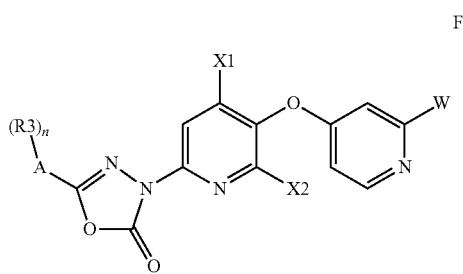

or a pharmaceutically acceptable salt, enantiomer, stereoisomer, or tautomer thereof,
wherein the A moiety is selected from C1-C6 alkyl, branched C3-C8alkyl, C3-C8carbocyclyl, phenyl or a 4-8 membered heterocyclic ring.

17. The compound of claim 16, wherein W is pyrazolyl or pyridinyl, optionally substituted with —(R5)$_p$.

18. The compound of claim 1, wherein the compound is a compound of Formula Ih,

Formula Ih

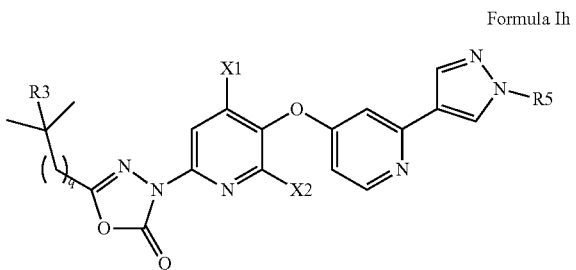

or a pharmaceutically acceptable salt, enantiomer, stereoisomer, or tautomer thereof.

19. The compound of claim 1 is selected from the group consisting of 3-(4-fluorobenzyl)-1-(6-methyl-5-((2-(1-methyl-1H-pyrazol-4-yl)pyridin-4-yl)oxy)pyridin-2-yl)-1H-1,2,4-triazol-5(4H)-one, 3-benzyl-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorobenzyl)-1-(5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-methyl-1H-pyrazol-4-yl)pyridin-4-yl)oxy)pyridin-2-yl)-1H-1,2,4-triazol-5(4H)-one, 3-isopropyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclohexyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-ethyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2'-methyl-[2,4'-bipyridin]-4-yl)oxy)pyridin-2-yl)-1H-1,2,4-triazol-5(4H)-one, 3-(tert-butyl)-1-(6-methyl-5-((6'-methyl-[2,3'-bipyridin]-4-yl)oxy)pyridin-2-yl)-1H-1,2,4-triazol-5(4H)-one, N-(4-((6-(3-(tert-butyl)-5-oxo-4,5-dihydro-1H-1,2,4-triazol-1-yl)-2-methylpyridin-3-yl)oxy)pyridin-2-yl)acetamide, 3-(tert-butyl)-1-(6-methyl-54(2-(2-methylthiazol-5-yl)pyridin-4-yl)oxy)pyridin-2-yl)-1H-1,2,4-triazol-5(4H)-one, 3-(tert-butyl)-4-methyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-(2-(4-(1-methylpiperidin-4-yl)phenyl)pyridin-4-yl)oxy)pyridin-2-yl)-1H-1,2,4-triazol-5(4H)-one, 3-(2-methoxyethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(2-methoxypropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(methoxymethyl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-(2-hydroxyethyl)-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(4-methyl-1H-imidazol-1-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(tetrahydro-2H-pyran-4-yl)-1H-1,2,4-triazol-5(4H)-one, N-(4-((6-(3-(tert-butyl)-5-oxo-4,5-dihydro-1H-1,2,4-triazol-1-yl)-2-methylpyridin-3-yl)oxy)pyridin-2-yl)-1-methylpiperidine-4-carboxamide, 3-isobutyl-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((2-(1-methyl-1H-imidazol-4-yl)pyridin-4-yl)oxy)pyridin-2-yl)-1H-1,2,4-triazol-5(4H)-one, 1-(5-((2-(1H-pyrazol-4-yl)pyridin-4-yl)oxy)-6-methylpyridin-2-yl)-3-(tert-butyl)-1H-1,2,4-triazol-5(4H)-one, 1-(6-methyl-5-((2-(1-methyl-1H-pyrazol-4-yl)pyridin-4-yl)oxy)pyridin-2-yl)-3-(tert-pentyl)-1H-1,2,4-triazol-5(4H)-one, 4-((6-(3-(tert-butyl)-5-oxo-4,5-dihydro-1H-1,2,4-triazol-1-yl)pyridin-3-yl)oxy)-N-methylpicolinamide, 1-(6-methyl-5-((2-(1-methyl-1H-pyrazol-4-yl)pyridin-4-yl)oxy)pyridin-2-yl)-3-(1-methylcyclopropyl)-1H-1,2,4-triazol-5(4H)-one, 3-(4-fluorophenyl)-1-(6-methyl-5-((2-(1-methyl-1H-pyrazol-4-yl)pyridin-4-yl)oxy)pyridin-2-yl)-1H-1,2,4-triazol-5(4H)-one, 3-(4-fluorophenyl)-1-(6-methyl-5-((2-(4-methyl-1H-imidazol-1-yl)pyridin-4-yl)oxy)pyridin-2-yl)-1H-1,2,4-triazol-5(4H)-one, 3-(4-((6-(3-(tert-butyl)-5-oxo-4,5-dihydro-1H-1,2,4-triazol-1-yl)-2-methylpyridin-3-yl)oxy)pyridin-2-yl)-1,1-dimethylurea, 3-(tert-butyl)-1-(4-methyl-5-((2-(1-methyl-1H-pyrazol-4-yl)pyridin-4-yl)oxy)pyridin-2-yl)-1H-1,2,4-triazol-5(4H)-one, N-(4-((6-(3-(4-fluorophenyl)-5-oxo-4,5-dihydro-1H-1,2,4-triazol-1-yl)-2-methylpyridin-3-yl)oxy)pyridin-2-yl)cyclopropanecarboxamide, 3-(tert-butyl)-1-(4,6-dimethyl-5-((2-(1-methyl-1H-pyrazol-4-yl)pyridin-4-yl)oxy)pyridin-2-yl)-1H-1,2,4-triazol-5(4H)-one, 3-cyclopentyl-1-(6-methyl-5-((2-(1-methyl-1H-pyrazol-4-yl)pyridin-4-yl)oxy)pyridin-2-yl)-1H-1,2,4-triazol-5(4H)-one, 3-cyclopropyl-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-neopentyl-1H-1,2,4-triazol-5(4H)-one, 3-cyclobutyl- 1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(5-((2-(1-ethyl-1H-pyrazol-4-yl)pyridin-4-yl)oxy)-6-methylpyridin-2-yl)-1H-1,2,4-triazol-5(4H)-one, 3-(tert-butyl)-1-(6-methyl-5-((2-(oxazol-5-yl)pyridin-4-yl)oxy)pyridin-2-yl)-1H-1,2,4-triazol-5(4H)-one, 3-(tert-butyl)-1-(6-methyl-5-(((6'-(4-methylpiperazin-1-yl)-[2,3'-bipyridin]-4-yl)oxy)pyridin-2-yl)-1H-1,2,4-triazol-5(4H)-one, 3-(tert-butyl)-1-(6-methyl-5-((2'-(4-methylpiperazin-1-yl)-[2,4'-bipyridin]-4-yl)oxy)pyridin-2-yl)-1H-1,2,4-triazol-5(4H)-one, 3-(1-hydroxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 1-(6-methyl-5-((2-(1-methyl-1H-pyrazol-4-yl)pyridin-4-yl)oxy)pyridin-2-yl)-3-(1-(trifluoromethyl)cyclobutyl)-1H-1,2,4-triazol-5(4H)-one, N-(4-((6-(3-(2-methoxypropan-2-yl)-5-oxo-4,5-dihydro-1H-1,2,4-triazol-1-yl)-4-methylpyridin-3-yl)oxy)pyridin-2-yl)acetamide, N-(4-((6-(3-(tert-butyl)-5-oxo-4,5-dihydro-1H-1,2,4-triazol-1-yl)-2-methylpyridin-3-yl)oxy)pyridin-2-yl)cyclopropanecarboxamide, 3-(1-methoxy-2-methylpropan-2-yl)-1-(6-methyl-5-((2-(1-methyl-1H-pyrazol-4-yl)pyridin-4-yl)oxy)pyridin-2-yl)-1H-1,2,4-triazol-5(4H)-one, 3-(tert-butyl)-1-(6-methyl-5-((6-(1-methyl-1H-pyrazol-4-yl)pyrimidin-4-yl)oxy)pyridin-2-yl)-1H-1,2,4-triazol-5(4H)-one, 4-(tert-butyl)-1-(6-methyl-5-((2-(1-methyl-1H-pyrazol-4-yl)pyridin-4-yl)oxy)pyridin-2-yl)-1H-imidazol-2(3H)-one, and 5-(tert-butyl)-3-(6-methyl-5-((2-(1-methyl-1H-pyrazol-4-yl)pyridin-4-yl)oxy)pyridin-2-yl)-1,3,4-oxadiazol-2(3H)-one.

20. A pharmaceutical composition, comprising a compound of claim 19 and a pharmaceutically acceptable carrier.

21. The compound 3-(tert-butyl)-1-(6-methyl-5-((2-(1-methyl-1H-pyrazol-4-yl)pyridin-4-yl)oxy)pyridin-2-yl)-1H-1,2,4-triazol-5(4H)-one.

22. A pharmaceutical composition, comprising a compound of claim 21 and a pharmaceutically acceptable carrier.

23. The compound 3-isopropyl-1-(6-methyl-5-((2-(1-methyl-1H-pyrazol-4-yl)pyridin-4-yl)oxy)pyridin-2-yl)-1H-1,2,4-triazol-5(4H)-one.

24. A pharmaceutical composition, comprising a compound of claim 23 and a pharmaceutically acceptable carrier.

25. The compound 1-(6-methyl-5-((2-(1-methyl-1H-pyrazol-4-yl)pyridin-4-yl)oxy)pyridin-2-yl)-3-(tert-pentyl)-1H-1,2,4-triazol-5(4H)-one.

26. A pharmaceutical composition, comprising a compound of claim 25 and a pharmaceutically acceptable carrier.

27. The compound.

28. A pharmaceutical composition, comprising a compound of claim 27 and a pharmaceutically acceptable carrier.

29. The compound 4-(tert-butyl)-1-(6-methyl-5-((2-(1-methyl-1H-pyrazol-4-yl)pyridin-4-yl)oxy)pyridin-2-yl)-1H-imidazol-2(3H)-one.

30. A pharmaceutical composition, comprising a compound of claim 29 and a pharmaceutically acceptable carrier.

31. A pharmaceutical composition, comprising a compound of claim 1 and a pharmaceutically acceptable carrier.

32. The composition of claim 31 further comprising an additive selected from adjuvants, excipients, diluents, or stabilizers.

33. A method of treating gastrointestinal stromal tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, cancers that are metastatic to bone, papillary thyroid carcinoma, non-small cell lung cancer, colonic cancers, rheumatoid arthritis, osteoarthritis, autoimmune nephritis, lupus, Crohn's disease, asthma, chronic obstructive pulmonary disease, osteoporosis, mastocytosis, and mast cell leukemia, the method comprising administering to a human patient in need thereof an effective amount of a compound of claim 1, or a pharmaceutically acceptable salt, enantiomer, stereoisomer, or tautomer thereof.

34. A method of treating glioblastomas, breast cancers, pancreatic cancers, or cancers that are metastatic to bone, the method comprising administering to a human patient in need thereof an effective amount of a compound of claim 1, or a pharmaceutically acceptable salt, enantiomer, stereoisomer, or tautomer thereof.

35. The method of claim 33, wherein the compound is administered orally, parenterally, by inhalation, or subcutaneously.

36. The method of claim 34, wherein the compound is administered orally, parenterally, by inhalation, or subcutaneously.

* * * * *

SEQUENCE LISTING

<160> NUMBER OF SEQ ID NOS: 3

<210> SEQ ID NO 1
<211> LENGTH: 435
<212> TYPE: PRT
<213> ORGANISM: Homo sapiens

<400> SEQUENCE: 1

Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
        35                  40                  45

Lys Thr Leu Gly Ala Gly Ala Phe Gly Lys Val Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
                85                  90                  95

Leu Lys Ile Met Ser His Leu Gly Gln His Glu Asn Ile Val Asn Leu
                100                 105                 110

Leu Gly Ala Cys Thr His Gly Gly Pro Val Leu Val Ile Thr Glu Tyr
            115                 120                 125

Cys Cys Tyr Gly Asp Leu Leu Asn Phe Leu Arg Arg Lys Ala Glu Ala
130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
            195                 200                 205

Asp Gly Arg Pro Leu Glu Leu Arg Asp Leu Leu His Phe Ser Ser Gln
        210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
        275                 280                 285

Ser Ile Phe Asp Cys Val Tyr Thr Val Gln Ser Asp Val Trp Ser Tyr
    290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
            355                 360                 365

Ile Cys Ser Phe Leu Gln Glu Gln Ala Gln Glu Asp Arg Arg Glu Arg
        370                 375                 380

Asp Tyr Thr Asn Leu Pro Ser Ser Ser Arg Ser Gly Gly Ser Gly Ser
385                 390                 395                 400

Ser Ser Ser Glu Leu Glu Glu Glu Ser Ser Ser Glu His Leu Thr Cys

```
                    405                 410                 415
Cys Glu Gln Gly Asp Ile Ala Gln Pro Leu Leu Gln Pro Asn Asn Tyr
            420                 425                 430

Gln Phe Cys
        435

<210> SEQ ID NO 2
<211> LENGTH: 676
<212> TYPE: PRT
<213> ORGANISM: Artificial Sequence
<220> FEATURE:
<223> OTHER INFORMATION: uKit with N-terminal GST fusion

<400> SEQUENCE: 2

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
210                 215                 220

Tyr Lys Lys Ala Gly Ser Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
        275                 280                 285

Leu Ser Phe Gly Lys Thr Leu Gly Ala Gly Ala Phe Gly Lys Val Val
290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
```

```
                        325                 330                 335
Leu Met Ser Glu Leu Lys Val Leu Ser Tyr Leu Gly Asn His Met Asn
                340                 345                 350

Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
        370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430

Pro Thr Lys Ala Asp Lys Arg Arg Ser Val Arg Ile Gly Ser Tyr Ile
        435                 440                 445

Glu Arg Asp Val Thr Pro Ala Ile Met Glu Asp Asp Glu Leu Ala Leu
450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Asp Val
        675

<210> SEQ ID NO 3
<211> LENGTH: 550
<212> TYPE: PRT
<213> ORGANISM: Homo sapiens

<400> SEQUENCE: 3

Gln Lys Lys Pro Arg Tyr Glu Ile Arg Trp Lys Val Ile Glu Ser Val
1               5                   10                  15
```

-continued

```
Ser Ser Asp Gly His Glu Tyr Ile Tyr Val Asp Pro Met Gln Leu Pro
            20                  25                  30

Tyr Asp Ser Thr Trp Glu Leu Pro Arg Asp Gln Leu Val Leu Gly Arg
        35                  40                  45

Thr Leu Gly Ser Gly Ala Phe Gly Gln Val Val Glu Ala Thr Ala His
    50                  55                  60

Gly Leu Ser His Ser Gln Ala Thr Met Lys Val Ala Val Lys Met Leu
65                  70                  75                  80

Lys Ser Thr Ala Arg Ser Ser Glu Lys Gln Ala Leu Met Ser Glu Leu
                85                  90                  95

Lys Ile Met Ser His Leu Gly Pro His Leu Asn Val Val Asn Leu Leu
            100                 105                 110

Gly Ala Cys Thr Lys Gly Gly Pro Ile Tyr Ile Ile Thr Glu Tyr Cys
        115                 120                 125

Arg Tyr Gly Asp Leu Val Asp Tyr Leu His Arg Asn Lys His Thr Phe
    130                 135                 140

Leu Gln His His Ser Asp Lys Arg Arg Pro Pro Ser Ala Glu Leu Tyr
145                 150                 155                 160

Ser Asn Ala Leu Pro Val Gly Leu Pro Leu Pro Ser His Val Ser Leu
                165                 170                 175

Thr Gly Glu Ser Asp Gly Gly Tyr Met Asp Met Ser Lys Asp Glu Ser
            180                 185                 190

Val Asp Tyr Val Pro Met Leu Asp Met Lys Gly Asp Val Lys Tyr Ala
    195                 200                 205

Asp Ile Glu Ser Ser Asn Tyr Met Ala Pro Tyr Asp Asn Tyr Val Pro
210                 215                 220

Ser Ala Pro Glu Arg Thr Cys Arg Ala Thr Leu Ile Asn Glu Ser Pro
225                 230                 235                 240

Val Leu Ser Tyr Met Asp Leu Val Gly Phe Ser Tyr Gln Val Ala Asn
                245                 250                 255

Gly Met Glu Phe Leu Ala Ser Lys Asn Cys Val His Arg Asp Leu Ala
            260                 265                 270

Ala Arg Asn Val Leu Ile Cys Glu Gly Lys Leu Val Lys Ile Cys Asp
        275                 280                 285

Phe Gly Leu Ala Arg Asp Ile Met Arg Asp Ser Asn Tyr Ile Ser Lys
    290                 295                 300

Gly Ser Thr Phe Leu Pro Leu Lys Trp Met Ala Pro Glu Ser Ile Phe
305                 310                 315                 320

Asn Ser Leu Tyr Thr Thr Leu Ser Asp Val Trp Ser Phe Gly Ile Leu
                325                 330                 335

Leu Trp Glu Ile Phe Thr Leu Gly Gly Thr Pro Tyr Pro Glu Leu Pro
            340                 345                 350

Met Asn Glu Gln Phe Tyr Asn Ala Ile Lys Arg Gly Tyr Arg Met Ala
        355                 360                 365

Gln Pro Ala His Ala Ser Asp Glu Ile Tyr Glu Ile Met Gln Lys Cys
    370                 375                 380

Trp Glu Glu Lys Phe Glu Ile Arg Pro Pro Phe Ser Gln Leu Val Leu
385                 390                 395                 400

Leu Leu Glu Arg Leu Leu Gly Glu Gly Tyr Lys Lys Lys Tyr Gln Gln
                405                 410                 415

Val Asp Glu Glu Phe Leu Arg Ser Asp His Pro Ala Ile Leu Arg Ser
            420                 425                 430

Gln Ala Arg Leu Pro Gly Phe His Gly Leu Arg Ser Pro Leu Asp Thr
```

-continued

```
            435                 440                 445
Ser Ser Val Leu Tyr Thr Ala Val Gln Pro Asn Glu Gly Asp Asn Asp
    450                 455                 460

Tyr Ile Ile Pro Leu Pro Asp Pro Lys Pro Glu Val Ala Asp Glu Gly
465                 470                 475                 480

Pro Leu Glu Gly Ser Pro Ser Leu Ala Ser Ser Thr Leu Asn Glu Val
                485                 490                 495

Asn Thr Ser Ser Thr Ile Ser Cys Asp Ser Pro Leu Glu Pro Gln Asp
            500                 505                 510

Glu Pro Glu Pro Glu Pro Gln Leu Glu Leu Gln Val Glu Pro Glu Pro
            515                 520                 525

Glu Leu Glu Gln Leu Pro Asp Ser Gly Cys Pro Ala Pro Arg Ala Glu
            530                 535                 540

Ala Glu Asp Ser Phe Leu
545                 550
```